(12) United States Patent
Jerecic et al.

(10) Patent No.: US 9,217,024 B2
(45) Date of Patent: Dec. 22, 2015

(54) ADDL RECEPTOR POLYPEPTIDES, POLYNUCLEOTIDES AND HOST CELLS FOR RECOMBINANT PRODUCTION

(75) Inventors: Jasna Jerecic, San Francisco, CA (US); Grant A. Krafft, Glenview, IL (US)

(73) Assignee: Acumen Pharmaceuticals, Inc., Livermore, CA (US)

( * ) Notice: Subject to any disclaimer, the term of this patent is extended or adjusted under 35 U.S.C. 154(b) by 1334 days.

(21) Appl. No.: 12/745,887

(22) PCT Filed: Dec. 17, 2008

(86) PCT No.: PCT/US2008/087196
§ 371 (c)(1), (2), (4) Date: Aug. 24, 2010

(87) PCT Pub. No.: WO2009/079566
PCT Pub. Date: Jun. 25, 2009

(65) Prior Publication Data
US 2010/0303897 A1 Dec. 2, 2010

Related U.S. Application Data

(60) Provisional application No. 61/014,742, filed on Dec. 18, 2007, provisional application No. 61/014,739, filed on Dec. 18, 2007, provisional application No. 61/014,729, filed on Dec. 18, 2007.

(51) Int. Cl.
*A61P 25/28* (2006.01)
*A61P 25/00* (2006.01)
*A61K 39/395* (2006.01)
*C07K 14/705* (2006.01)

(52) U.S. Cl.
CPC .................................. *C07K 14/705* (2013.01)

(58) Field of Classification Search
None
See application file for complete search history.

(56) References Cited

U.S. PATENT DOCUMENTS

| | | | |
|---|---|---|---|
| 3,740,421 A | 6/1973 | Kramaric |
| 4,203,670 A | 5/1980 | Bromberg |
| 4,420,568 A | 12/1983 | Wang |
| 4,429,230 A | 1/1984 | Honkawa |

(Continued)

FOREIGN PATENT DOCUMENTS

| | | |
|---|---|---|
| EP | 0998495 | 12/2006 |
| EP | 1808444 | 7/2007 |

(Continued)

OTHER PUBLICATIONS

Renden et al., Glutamate Transporter Studies Reveal the Pruning of Metabotropic Glutamate Receptors and Absence of AMPA Receptor Desensitization at Mature Calyx of Held Synapses. The Journal of Neuroscience, Sep. 14, 2005 • 25(37):8482-8497.*

Acumen Pharmaceuticals, Developing Disease-Modifying Drugs that Block and Reverse Memory Loss in Alzheimer's Disease, Science Update SFN Reception, Atlanta, GA—Presentation (2006).

Acumen Pharmaceuticals, New Alzheimer's Disease Therapeutics: Preventing ADDL Compromise of Synaptic Signaling, Neurodegenerative Diseases: Biology and Therapeutics: Cold Spring Harbor, New York, Presentation (2006).

(Continued)

*Primary Examiner* — Gregory S Emch
*Assistant Examiner* — Aurora M Fontainhas
(74) *Attorney, Agent, or Firm* — Foley & Lardner LLP

(57) ABSTRACT

This invention provides a novel receptor expressed on neuronal cells in a developmentally-specific manner. Accordingly, this invention provides the amino acid sequences of selected portions of the receptor and polynucleotides encoding these portions as well as antibodies that bind to the polypeptide portions of the receptor. Compositions and methods for using the compositions are also provided.

27 Claims, 10 Drawing Sheets

(56) References Cited

U.S. PATENT DOCUMENTS

| | | | |
|---|---|---|---|
| 4,476,229 A | 10/1984 | Fino | |
| 4,510,251 A | 4/1985 | Kirkemo | |
| 4,585,862 A | 4/1986 | Wang | |
| 4,614,823 A | 9/1986 | Kirkemo | |
| 4,668,640 A | 5/1987 | Wang | |
| 4,681,859 A | 7/1987 | Kramer | |
| 4,751,190 A | 6/1988 | Chiapetta | |
| 4,863,876 A | 9/1989 | Hevey | |
| 4,952,691 A | 8/1990 | Wang | |
| 5,066,426 A | 11/1991 | Wang | |
| 5,070,025 A | 12/1991 | Klein | |
| 5,206,179 A | 4/1993 | Ramsey | |
| 5,229,490 A | 7/1993 | Tam | |
| 5,315,015 A | 5/1994 | Hui | |
| 5,391,740 A | 2/1995 | Wang | |
| 5,407,834 A | 4/1995 | Dubler | |
| 5,427,960 A | 6/1995 | Wang | |
| 5,445,935 A | 8/1995 | Royer | |
| 5,589,568 A | 12/1996 | Higashijima | |
| 5,756,292 A | 5/1998 | Royer | |
| 5,804,395 A | 9/1998 | Schade | |
| 5,914,245 A | 6/1999 | Bylina | |
| 5,976,820 A | 11/1999 | Jolley | |
| 5,981,200 A | 11/1999 | Tsien | |
| 6,066,505 A | 5/2000 | Cheng | |
| 6,077,675 A | 6/2000 | Stormann | |
| 6,171,807 B1 | 1/2001 | Novitsky | |
| 6,197,928 B1 | 3/2001 | Tsien | |
| 6,207,397 B1 | 3/2001 | Lynch | |
| 6,218,506 B1 | 4/2001 | Krafft | |
| 6,280,981 B1 | 8/2001 | Dykens | |
| 6,284,544 B1 | 9/2001 | Thompson | |
| 6,291,201 B1 | 9/2001 | Garman | |
| 6,294,330 B1 | 9/2001 | Michnick | |
| 6,323,039 B1 | 11/2001 | Dykens | |
| 6,326,142 B1 | 12/2001 | Royer | |
| 6,331,392 B1 | 12/2001 | Laing | |
| 6,348,322 B1 | 2/2002 | Strittmatter | |
| 6,376,257 B1 | 4/2002 | Persechini | |
| 6,432,632 B2 | 8/2002 | Nakayama | |
| 6,448,018 B1 | 9/2002 | Nakayama | |
| 6,456,734 B1 | 9/2002 | Youvan | |
| 6,472,156 B1 | 10/2002 | Wittwer | |
| 6,495,664 B1 | 12/2002 | Cubitt | |
| 6,511,815 B1 | 1/2003 | Burke | |
| 6,515,113 B2 | 2/2003 | Raymond | |
| 6,555,326 B1 | 4/2003 | Lustig | |
| 6,569,628 B2 | 5/2003 | Laing | |
| 6,596,546 B1 | 7/2003 | Jolley | |
| 6,600,017 B1 | 7/2003 | Glabe | |
| 6,623,926 B1 | 9/2003 | Lohse | |
| 6,630,295 B2 | 10/2003 | Mayer | |
| 6,639,078 B1 | 10/2003 | Haffner | |
| 6,642,001 B1 | 11/2003 | Bolk | |
| 6,661,909 B2 | 12/2003 | Youvan | |
| 6,689,574 B1 | 2/2004 | Cummings | |
| 6,713,276 B2 | 3/2004 | Cordell | |
| 6,762,280 B2 | 7/2004 | Schmidt | |
| 6,770,448 B2 | 8/2004 | Glabe | |
| 6,794,158 B2 | 9/2004 | Ingraham | |
| 6,803,188 B1 | 10/2004 | Tsien | |
| 6,824,990 B1 | 11/2004 | Blumer | |
| 6,828,106 B2 | 12/2004 | Colyer | |
| 6,846,813 B2 | 1/2005 | Beck | |
| 6,864,103 B2 | 3/2005 | Raymond | |
| 6,864,290 B2 | 3/2005 | Schostarez | |
| 6,906,104 B2 | 6/2005 | Schostarez | |
| 6,908,769 B2 | 6/2005 | Belik | |
| 6,927,236 B2 | 8/2005 | Vertesy | |
| 6,927,401 B1 | 8/2005 | Palo | |
| 6,949,575 B2 | 9/2005 | Barta | |
| 7,179,892 B2 | 2/2007 | Basi | |
| 7,189,819 B2 | 3/2007 | Basi | |
| 7,256,273 B2 | 8/2007 | Basi | |
| 2003/0068316 A1 | 4/2003 | Klein | |
| 2005/0053575 A1 | 3/2005 | Solomon | |
| 2005/0089571 A1 | 4/2005 | Beckert | |
| 2005/0233321 A1* | 10/2005 | Hess et al. | 435/6 |
| 2006/0166275 A1 | 7/2006 | Krafft | |
| 2006/0178302 A1 | 8/2006 | Krafft | |
| 2006/0228349 A1 | 10/2006 | Acton | |
| 2007/0048312 A1 | 3/2007 | Klein | |
| 2007/0081998 A1 | 4/2007 | Kinney | |
| 2007/0098721 A1 | 5/2007 | Hillen | |
| 2007/0218499 A1 | 9/2007 | Lambert | |
| 2007/0237740 A1 | 10/2007 | Reddington | |
| 2008/0306074 A1 | 12/2008 | Lacor | |
| 2009/0018084 A1 | 1/2009 | Krafft | |
| 2009/0018218 A1 | 1/2009 | Krafft | |
| 2011/0098309 A1 | 4/2011 | Look | |

FOREIGN PATENT DOCUMENTS

| | | |
|---|---|---|
| EP | 1571158 | 10/2009 |
| WO | WO 96/29404 | 9/1996 |
| WO | WO 98/33815 | 8/1998 |
| WO | WO 01/10900 | 2/2001 |
| WO | WO 01/55093 | 8/2001 |
| WO | WO 02/32896 | 4/2002 |
| WO | WO 03/080032 | 10/2003 |
| WO | WO 03/104437 | 12/2003 |
| WO | WO 2004/031400 | 4/2004 |
| WO | WO 2005/034940 | 4/2005 |
| WO | WO 2005/037257 | 4/2005 |
| WO | WO 2005/110056 | 11/2005 |
| WO | WO 2005/116640 | 12/2005 |
| WO | WO 2006/014478 | 2/2006 |
| WO | WO 2006/055178 | 5/2006 |
| WO | WO 2007/050359 | 5/2007 |
| WO | WO 2007/088400 | 8/2007 |
| WO | WO 2007/134449 | 11/2007 |
| WO | WO 2008/076262 | 6/2008 |
| WO | WO 2009/008890 | 1/2009 |
| WO | WO 2009/008891 | 1/2009 |
| WO | WO 2009/009768 | 1/2009 |
| WO | WO 2009/079566 | 6/2009 |

OTHER PUBLICATIONS

Ayala et al., Group III mGluR of Synaptic Transmission at the SC-CA1 Synapse in Developmentaly Regulated, Neuropharmacology, 2008, 54(5):804-814.

Berg et al., Rapid Impact of R-Amyloid on Paxillin in a Neural Cell Line, J. Neurosci. Res., 1997 50:979-989.

Blennow et. al., Alzheimer's Disease, Seminar, Clinical Neurochemistry Laboratory, Dept. of Neuroscience and Physiology, 2006, vol. 368, pp. 387-403.

Catalano et al., The Role of Amyloid-Beta Derived Diffusible Ligands (ADDLs) in Alzheimer's Disease, Current Topics in Medicinal Chemistry, 2006, Bentham Science Publishers, Hilversum, NL, vol. 6, pp. 597-608.

Chang et al., Femtomole Immunodetection of Synthetic and Endogenous Amyloid-β Oligomers and Its Application to Alzheimer's Disease Drug Candidate Screening, J. Mol. Neurosci., 2003, 20:305-313.

Cleary et al., Natural Oligomers of the Amyloid-β Protein Specifically Disrupt Cognitive Function, Nat. Neurosci., 2005, 8:79-84.

De Felice et al., Alzheimer's Disease-type Neuronal Tau Hyperphosphorylation Induced by Aβ Oligomers, Neurobiol Aging, 2008, 29(9):1334-1347.

De Felice et al., Inhibition of Alzheimer's Disease β-amyloid Aggregation, Neurotoxicity, and In Vivo Deposition by Nitrophenols: Implications for Alzheimer's Therapy, FASEB J. Published online Mar. 20, 2001.

De Felice et al., Targeting the Neurotoxic Species in Alzheimer's Disease: Inhibitors of Aβ Oligomerization FASEB J., 2004, vol. 18, pp. 1366-1372.

Dodart et al., Immunization Reverses Memory Deficits Without Reducing Brain Aβ Burden in Alzheimer's Disease Model, Nat. Neurosci., 2002, 5:452-457.

(56) References Cited

OTHER PUBLICATIONS

Doggrell, A Small-molecule Lead Compound for the Treatment of Alzheimer's Disease, Expert Opinion, Investig. Drugs, 2005, vol. 14, No. 2, pp. 199-201.
Ferraguti et al., Metabotropic Glutamate Receptor 8—Expressing Nerve Terminals Target Subsets of GABAergic Neurons in the Hippocampus, J. Neuroscience, 2005, 25(45):10520-10536.
Fulop et al., β-Amyloid pentapeptide RIIGLa Inhibits Aβ1-42 Aggregation and Toxicity, Biochem. Biophys. Res. Commun., 2004, vol. 324, pp. 64-69.
Gervais, GAG Memetics: Potential to Modify Underlying Disease Process in AD, Neurobiol. Aging, 2004, vol. 25, pp. S11-S12.
Gong et al., Alzheimer's Disease-affected Brain: Presence of Oligomeric Aβ Ligands (ADDLs) Suggests a Molecular Basis for Reversible Memory Loss, Proc. Natl. Acad. Sci., 2003, 100:10417-10422.
Goure et al., Development of Novel, ADDL-targeting, Disease Modifying Therapeutics for the Treatment Alzheimer's Disease, 8th International AD-PD Conference Mar. 14-18, 2007—Abstract (2007).
Goure et al., Development of Novel, ADDL-targeting, Disease Modifying Therapeutics for the Treatment Alzheimer's Disease, 8th International AD-PD Conference Mar. 14-18, 2007—Poster (2007).
Goure et al., Preclinical Development of Disease Modifying Therapeutics for the Treatment Alzheimer's Disease, Alzheimer's Disease International Conference—Jun. 9-12, 2007—Abstract (2007).
Guzowski et al., Inhibition of Activity-dependent Arc Protein Expression in the Rat Hippocampus Impairs the Maintenance of Long-term Potentiation and the Consolidation of Long-term Memory, J. Neurosci., 2000, 20(11):3993-4001.
Hardy et al., The Amyloid Hypothesis of Alzheimer's Disease: Progress and Problems on the Road to Therapeutics, Science, 2002, 297:353-356.
Kayed et al., Common Structure of Soluble Amyloid Oligomers Implies Common Mechanism of Pathogenesis, Science, 2003, 300:486-489.
Kim et al., Selective Neuronal Degeneration Induced by Soluble Oligomeric Amyloid Beta Protein, FASEB J., 2003, 17:118-120.
Klein et al., Targeting Small Aβ Oligomers: The Solution to an Alzheimer's Disease Conundrum, Trends Neuroscis., 2001, 24:219-224.
Kotilinek et al., Reversible Memory Loss in a Mouse Transgenic Model of Alzheimer's Disease, J. Neurosci., 2002, 22:6331-6335.
Krafft et al., Discovery of ADDL-Targeting Small Molecule Drugs for Alzheimer's Disease, ICAD Jul. 15-20, 2006 Poster (2006).
Krafft, Alzheimer's Disease: From Molecular Mechanisms to Drug Discover, Apr. 18, 2007, Punta Cana, Dominican Republic—Presentation (2007).
Lacor et al., Synaptic Targeting by Alzheimer's-related Amyloid β Oligomers, J. Neurosci., 2004, 24(45):10191-10200.
Lambert et al., Diffusible, Nonfibrillar Ligands Derived from Aβ$_{1-42}$ Are Potent Central Nervous System Neurotoxins, Proc. Natl. Acad. Sci. USA, 1998, 95:6448-6453.
Lambert et al., Monoclonal Antibodies that Target Pathological Assemblies of Aβ, J. Neurochem., 2007, 100(1):23-35.
Lambert et al., Vaccination with Soluble Aβ Oligomers Generates Toxicity-neutralizing Antibodies, J. Neurochem., 2001, 79:595-605.
Lecanu et al., Identification of Naturally Occurring Spirostenols Preventing β-amyloid-induced Neurotoxicity, Steroids, 2004, vol. 69, pp. 1-16.
Lesne et al., A Specific Amyloid-β Protein Assembly in the Brain Impairs Memory, Nature, 2006, 440:352-357.
Liu et al., Trehalose Differentially Inhibits Aggregation and Neurotoxicity of beta-amyloid 40 and 42, Neurobiol. Disease, 2005, vol. 20, pp. 74-81.
Look et al., Discovery of ADDL-targeting Small Molecule Drugs for Alzheimer's Disease, Current Alzheimer Research, 2007, vol. 4, No. 5, pp. 562-567.
Maezawa et al., A Novel Tricyclic pyrone Compound Ameliorates Cell Death Associated with Intracellular Amyloid-β oligomeric Complexes, J. Neurochem., 2006, vol. 98, pp. 57-67.

Matsubara et al., Soluble Aβ Homeostasis in AD and DS: Impairment of Anti-amyloidogenic Protection by Lipoproteins, Neurobiol. Aging, 2004, 25:833-841.
McLaurin et al., Cyclohexanehexol Inhibitors of Aβ Aggregation Prevent and Reverse Alzheimer Phenotype in a Mouse Model, Nature Med., 2006, vol. 12, pp. 801-808.
Necula et al., Small Molecule Inhibitors of Aggregation Indicate that Amyloid β Oligomerization and Fibrillization Pathways are Independent and Distinct, J. Biol. Chem., 2007, vol. 282, No. 14, pp. 10311-10324.
Pray et al., A Homogenous Fluorescence Assay of ADDL Assembly and Anti-ADDL Antibody Properties, Neuroscience 36th Annual meeting Oct. 14-18, 2006 Atlanta, GA—Abstract (2006).
Pray et al., A Homogenous Fluorescence Assay of ADDL Assembly, Neuroscience 36th Annual meeting Oct. 14-18, 2006 Atlanta, GA—Presentation (2006).
Ritchie et al., Metal-protein Attenuation with Iodochlorhydroxyquin (Clioquinol) Targeting a Beta Amyloid Deposition and Toxicity in Alzheimer Disease, Arch. Neurol., 2003, vol. 60, pp. 1685-1691.
Roche et al., Development of Virtual Screening Method for Identification of "Frequent Hitters" in Compound Libraries, J. Med. Chem., 2002, vol. 45, pp. 137-142.
Roher et al, β-Amyloid-(1-42) is a Major Component of Cerebrovascular Amyloid Deposits: Implications for the Pathology of Alzheimer Disease, Proceedings of the National Academy of Science, 1993, Washington, D.C., vol. 90, pp. 10836-10840.
Roher et al., Morphology and Toxicity of Aβ-(1-42) Dimer Derived from Neuritic and Vascular Amyloid Deposits of Alzheimer's Disease, Journal of Biological Chemistry, 1996, American Society of Biochemical Biologists, Birmingham, U.S., vol. 271, No. 34, pp. 20631-20635.
Selkoe, Alzheimer's Disease in a Synaptic Failure, Science, 2002, 298:789-791.
Shanker et al., Natural Oligomers of the Alzheimer Amyloid-β Protein Induce Reversible Synpase Loss by Modulating an NMDA-Type Glutamate Receptor-Dependent Signaling Pathway, Neurosci., 2007, 27(11):2866-2875.
Steward et al., Synaptic Activation Causes the mRNA for the IEG Arc to Localize Selectively Near Activated Postsynaptic Sites on Dendrites, Neuron, 1998, 21:741-751.
Walsh et al., Naturally Selected Oligomers of Amyloid β Protein Potently Inhibit Hippocampal Long-term Potentiation in Vivo, Nature, 2002, 416:535-539.
Wang et al., Soluble Oligomers of β-amyloid (1-42) Inhibit Long-term Potentiation but not Long-term Depression in Rat Dentate Gyrus, Brain Research, 2002, vol. 924, pp. 133-140.
Yang et al., Curcumin Inhibits Formation of Amyloid β Oligomers and Fibrils, Binds Plaques, and Reduces Amyloid in Vivo, J. Biol. Chem., 2005, vol. 280, No. 7, pp. 5892-5901.
Yao et al., The Ginkgo Biloba Extract EGb 761 Rescues the PC12 Neuronal Cells from β-amyloid-Induced Cell Death by Inhibiting the Formation of β-amyloid-derived Diffusible Neurotoxic Ligands, Brain Res., 2001, vol. 889, pp. 181-190.
Yu et al., Per-6-Substituted β-cyclodextrin Libraries Inhibit Formation of β-Amyloid-Peptide (Aβ)-Derived, Soluble Oligomers, J. Mol. Neurosci., 2002, vol. 19, pp. 51-55.
Zhang et al., Deafferentation Leads to a Down-regulation of Nitric Oxide Synthase in the Rat Visual System, Neurosci. Letters, 1996, 211, pp. 61-64.
Zhao et al., Amyloid Beta Oligomers Induce Impairment of Neuronal Insulin Receptors, FASEB J., 2008, vol. 22, pp. 246-260.
Author Unknown, Stem Cell Information: The National Institutes of Health Resource for Stem Cell Research, Appendix E: Stem Cell Markers, Published online Nov. 26, 2007, http://stemcells.nih.gov/info/scireport/appendixE.asp.
Canadian Office Action for Canadian Application No. 2,707,309 dated Feb. 18, 2015.
Hida et al., "Directed evolution for drug and nucleic acid delivery", Advanced Drug Delivery Reviews, 59 (2007) pp. 1562-1578.

* cited by examiner

FIG. 2

```
AVIMFANEDDIR          (1)  ------------------------------------AVIMFANEDDIR--                    SEQ ID NO. 2
       Rat mGluR8    (243) GGVCIAQSQKIPREPRPG----EFEKIIKRLLETPNARAVIMFANEDDIRRI                   SEQ ID NO. 33
Predicted XP377945    (2)  DGVCIAQSQKIPREPRPG----EFEKIIKCLLETPNARAVIMFANEDDIRRI                   SEQ ID NO. 34
       Rat mGluR6    (235) GGVCIAQSIKIPREPKPG----EFHKVIRRLMETPNARGIIIFANEDDIRRV                   SEQ ID NO. 35
       Rat mGluR7    (246) GGLCIAQSVRIPQERKDRTIDFDRIIKQLLDTPNSRAVVIFANDEDIKQI                     SEQ ID NO. 36
       Rat mGluR4    (246) GGVCIAQSVKIFREPKTG---EFDKIIKRLLETSNARGIIIIFANEDDIRRV                   SEQ ID NO. 37
                                                                                   350

ASIDGFDQYFR           (1)  ---------------------------------------------ASIDG                    SEQ ID NO. 4
ASIDGFDQYFRSQTLANNR   (1)  ---------------------------------------------ASIDG                    SEQ ID NO. 3
       Rat mGluR8    (291) LEAAKKLNQSGHFLRIGSDSWGSKIAPVYQQEEIAEGAVTILPRRASIDG                     SEQ ID NO. 33
Predicted XP_377945   (50) LEAAKKLNQSGHFLRIGSDSWGSKIAPVYQQEEIAEGAVTILPRRASIDG                     SEQ ID NO. 34
       Rat mGluR6    (283) LEATRQANLTGHFLWVGSDSWGSKISPILNLEEEAVGAITTLPRRASIDG                     SEQ ID NO. 35
       Rat mGluR7    (296) LAAAKRADQVGHFLWGSDSWGSKINPLHQHEDIAEGAITTQPKRATVEG                      SEQ ID NO. 36
       Rat mGluR4    (294) LEAARRANCTGHFFWMGSDSWGSKSAPVLRLEEVAEGAVTILPKRMSVRG                     SEQ ID NO. 37
                      351                                                         400

ASIDGFDQYFR           (6)  FDQYFR--------------------------------------------                     SEQ ID NO. 4
ASIDGFDQYFRSQTLANNR   (6)  FDQYFRSQTLANNR------------------------------------                     SEQ ID NO. 3
       Rat mGluR8    (341) FDRYFRSRTLANMRRNVWFAEFWEENFGCKL-GSHGKRNSHIKCTGLER                      SEQ ID NO. 33
Predicted XP_377945  (100) FDQYFRSQTLANNRNVWFAEFWEENFGCKL-GSHGKRNSHIKCTENVP                       SEQ ID NO. 34
CTENVP                (1)  -----------------------------------------CTENVP                       SEQ ID NO. 5
       Rat mGluR6    (333) FDQYFMTRSLENNRRNIWFAEFWEENFNCKLTSSGGQSDDSTRKCTGEER                     SEQ ID NO. 35
       Rat mGluR7    (346) FDAYFTSRTLENNRRNVWFAEYWEENFNCKLTISGSKKEDTDRKCTRQER                     SEQ ID NO. 36
       Rat mGluR4    (344) FDRYPSSRTLDNNRRNIWFAEFWEDNFHCKLSRHALKKGSHIRKCTNRER                     SEQ ID NO. 37
                      401                                                         450

Rat mGluR8    (390) IARDSSYEQEGKVQFVIDAVYSMAYALHNMHKERCPGYIGLCPRMVTIDG                     SEQ ID NO. 33
Predicted XP_377945  (149) VTDFFVGPVCIIPKTDTKPRSSVWDERGHDSHIPLEDCRFD                              SEQ ID NO. 34
VTDFFVGPVCIIPK        (7)  VTDFFVGPVCIIPK------------------------------------                     SEQ ID NO. 5
SSVWDERHDSHIPLEDCR    (1)  --------------SSVWDERHDSHIPLEDCR------------------                     SEQ ID NO. 6
HDSHIPLEDCR           (1)  ----------------------HDSHIPLEDCR-----------------                     SEQ ID NO. 7
       Rat mGluR6    (383) IGQDSAYEQEGKVQFVIDAVYAIAHALSMMQAILCPGHTGLCPAMEPTDG                     SEQ ID NO. 35
       Rat mGluR7    (396) IGKDSNYEQEGKVQFVIDAVYAMAHALTHNRKDLCADYRGVCPEMEQAGG                     SEQ ID NO. 36
       Rat mGluR4    (394) IGQDSAYEQEGKVQFVIDAVYAMGHAIYAMHRICPGRVGLCPRMDPVDG                      SEQ ID NO. 37
                      451                                                         500
```

FIG. 3

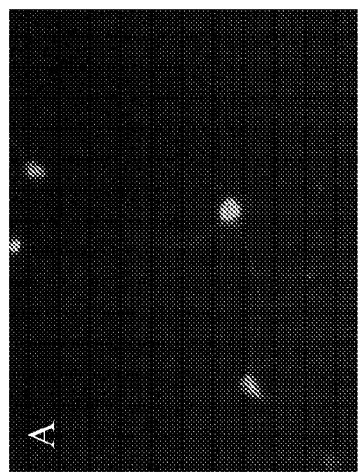
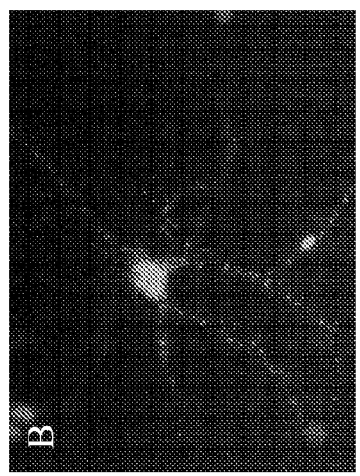
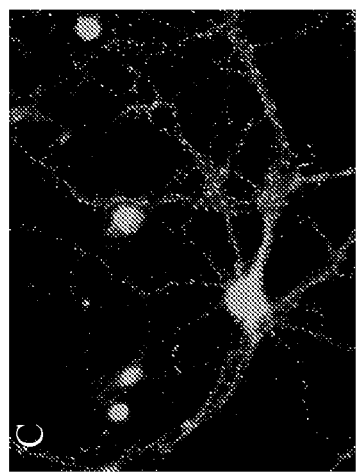
FIG. 4

ADDL RECEPTOR POLYPEPTIDES, POLYNUCLEOTIDES AND HOST CELLS FOR RECOMBINANT PRODUCTION

CROSS-REFERENCE TO RELATED APPLICATIONS

This application is a National Phase application under 35 U.S.C. §371 of PCT Application PCT/US2008/087196, filed Dec. 17, 2008, which claims benefit from U.S. Provisional Application No. 61/014,729, filed Dec. 18, 2007, U.S. Provisional Application No. 61/014,739, filed Dec. 18, 2007 and U.S. Provisional Application No. 61/014,742, filed Dec. 18, 2007, which are hereby incorporated by reference in their entirety.

SEQUENCE LISTING

The instant application contains a Sequence Listing which has been filed electronically in ASCII format and is hereby incorporated by reference in its entirety. Said ASCII copy, created on Dec. 12, 2014, is named 089265-1801_SL.txt and is 41,381 bytes in size.

BACKGROUND OF THE INVENTION

1. Field of the Invention

This invention relates to the isolation and modulation of a receptor molecule, which binds ADDLs and mediates the memory compromising effects of ADDLs.

2. State of the Art

Alzheimer's disease (AD) is a fatal progressive dementia that has no cure at present. Although the molecular basis of the disease is not established, the present theory implicates neurotoxins derived from amyloid beta (Aβ) peptides and in particular the 42-amino acid amyloid beta peptide ($A\beta_{1-42}$). Aβ is an amphipathic peptide, the abundance of which is increased by gene mutations and risk factors linked to AD. Fibrils formed from Aβ constitute the cores of amyloid senile plaques, which have been purified from the brains of AD patients. Analogous fibrils generated in vitro are lethal to cultured neurons, albeit at high, non-physiologically relevant concentrations. Nevertheless, these findings provided the central rationale for the original "amyloid cascade hypothesis", which invoked Aβ fibril deposition and consequent neuronal death as the cause of AD memory loss (Hardy and Higgins (1992) Science 256:184-185).

Although experimental support of a causative role for $A\beta_{1-42}$ in AD is strong, a number of key observations are simply not consistent with the original amyloid cascade hypothesis. One such observation is the remarkable selectivity of neuron degeneration, which is prevalent among neurons in the entorhinal cortex and CA1 hippocampal region, slight in the hippocampal CA3 region, and virtually non-existent the cerebellum. Unfortunately, the location of Aβ plaques does not correspond to these affected regions, and the overall plaque burden does not correlate with the extent of cognitive decline. (Katzman (1988) Ann. Neurol. 23(2):138-144).

Other inconsistencies emerged from studies involving Aβ overproducing transgenic AD mouse models. For example, when Aβ-targeting monoclonal antibodies were injected peripherally, two surprising results were obtained: (1) the vaccinated mice showed rapid reversal of memory loss, with recovery evident within the first 24 hours; and (2) the cognitive benefits of vaccination accrued despite no change in senile plaque Aβ levels (Dodart et al. (2002) Nat. Neurosci 5:452-457; Kotilinek et al. (2002) J. Neurosci. 22:6331-6335). Such findings are not consistent with a mechanism for memory loss dependent on neuron death caused by amyloid fibrils.

Within the past few years, the original amyloid cascade hypothesis has been revised and updated to accommodate the role of Aβ assemblies other than fibrils. In particular, soluble, non-fibrillar oligomers of $A\beta_{1-42}$ known as amyloid β-derived diffusible ligands (ADDLs) are highly potent neurotoxins, which assemble from low $A\beta_{1-42}$ concentrations (Lambert et al. (1998) Proc. Natl. Acad. Sci. USA 95:6448-6453). ADDLs are the missing links in the original amyloid cascade hypothesis, and they are capable of rapid inhibition of long term potentiation (Lambert et al. (1998) Proc. Natl. Acad. Sci. USA 95:6448-6453; Walsh et al. (2002) Nature 416: 535-539; Wang et al. (2002) Brain Res. 924:133-140), a classic experimental paradigm for memory and synaptic plasticity. In the updated Aβ cascade hypothesis, elevated $A\beta_{1-42}$ monomer incorporates either into fibrils and plaques or assembles into ADDLs, wherein these two processes are separate and distinct, as illustrated below:

amyloid senile plaque⇆Monomeric $AB_{1-42}$⇆ADDLs

The memory loss that occurs in AD stems from ADDL-induced synapse failure prior to neuron death, and not from fibrils, which contribute primarily to inflammatory and oxidative AD pathology (Hardy and Selkoe (2002) Science 297: 353-356).

ADDLs have been shown to be prevalent in AD brain tissue, with levels more than 70-fold higher than levels in age matched control tissue (Kayed et al. (2003) Science 300:486-489; Gong et al. (2003) Proc. Natl. Acad. Sci. USA 100: 10417-10422). ADDLs also are prevalent in AD transgenic mice models (Kotilinek et al. (2002) J. Neurosci. 22:6331-6335; Chang et al. (2003) J. Mol. Neurosci. 20:305-313). Further experiments have shown important neurological properties of ADDLs. ADDLs exhibit selective toxicity to hippocampal CA1 neurons compared with CA3 neurons, and the complete absence of toxicity towards cerebellar neurons (Kim et al. (2003) FASEB J. 17:118-120). Ventricular injection of $A\beta_{1-42}$ oligomers into wild-type rats results in rapid behavioral compromise, with complete recovery occurring within 24 hours (Cleary et al. (2005) Nat. Neurosci. 8:79-84). These deficits have been attributed to higher order oligomers, specifically dodecamers (12-mers) (Lesne et al. (2006) Nature 440:352-357). ADDLs bind to neurons with high specificity, and they localize to post-synaptic receptors that are present only on a subset of hippocampal neurons (Lacor et al. (2004) J. Neurosci. 24:10191-10200). This binding triggers the rapid and persistent up-regulation of the immediate early gene product arc, translation of which is activity dependent at polyribosomes localized to subsets of dendritic spines (Steward et al. (1998) Neuron 21:741-751; Guzowski et al. (2000) J. Neurosci. 20:3993-4001). More recently, ADDLs have been implicated as upstream activators of tau phosphorylation and have been shown to interfere with animal behavior at femtomolar levels (Matsubara et al. (2004) Neurobiol. Aging 25:833-841).

The reversibility of memory loss in mouse models, coupled with the neurological properties of ADDLs and their presence in the AD brain, provides strong support for the ADDL hypothesis that AD is a disease of ADDL-induced synaptic failure rather than cell death (Lambert et al. (1998) Proc. Natl. Acad. Sci. USA 95:6448-6453; Klein et al. (2001) Trends Neurosci. 24:219-220; Selkoe (2002) Science 298:789-791). The ADDL hypothesis also nicely explains the selectivity of neuronal susceptibility in AD, by invoking a specific ADDL receptor expressed on subsets of neurons in affected regions of the brain.

Prior to the work associated with the invention disclosed herein, there has not been definitive identification of a neuronal receptor that specifically binds ADDLs and mediates the memory compromising effects of ADDLs. The invention described here is highly significant from the standpoint of therapeutic intervention, because definitive identification of the ADDL receptor will enable the discovery of new composition and methods to inhibit, regulate, and/or modulate ADDL binding to neuronal cells, thereby obviating ADDL-triggered memory compromise and neurodegeneration in AD, MCI, Down's syndrome and other ADDL-related diseases. This invention satisfies this important need and provides related advantages as well.

SUMMARY OF THE INVENTION

Applicants have identified a novel receptor that is expressed on neuronal cells in a developmentally-specific manner. Accordingly, this invention provides the amino acid sequences of selected portions of the receptor and polynucleotides encoding these portions as well as antibodies that bind to the polypeptide portions of the receptor. The specific polypeptides are identified in Table 1 along with their respective sequence listing identifier numbers (SEQ ID). Equivalent polypeptides having a predetermined sequence homology or identity to the specific sequence identified below are further provided herein.

TABLE 1

| SEQ ID NO. | AMINO ACID SEQUENCE |
|---|---|
| 1 | ARAVIMFANEDDIRRILEAAKKLNQSGHFLWIGSDSWGSKIAPVYQQEEIAEGAVTILPKRASIDGFDQYFRSQTLANNRRNVWFAEFWEENFGCKLGSHGKRNSHIKKCTENVPVTDFFVGPVCIIPKTDTKPRSSVWDERHDSHIPLEDCRF |
| 2 | AVIMFANEDDIR |
| 3 | ASIDGFDQYFRSQTLANNR |
| 4 | ASIDGFDQYFR |
| 5 | CTENVPVTDFFVGPVCIIPK |

TABLE 1-continued

| SEQ ID NO. | AMINO ACID SEQUENCE |
|---|---|
| 6 | SSVWDERHDSHIPLEDCR |
| 7 | HDSHIPLEDCR |
| 8 | ASIDGFDQYFRSQTLANNRRNVWFAEFWEENFGCKLGSHGKRNSHIKKCTENVPVTDFFVGPVCIIPKTDTKPRSSVWDERHDSHIPLEDCR |

This invention also provides compositions comprising the isolated polypeptides. The compositions can be used diagnostically or therapeutically to inhibit ligand binding to and/or activation of the native receptor. In one aspect, the polypeptides of this invention are bound to a detectable label. Antibodies that bind to these polypeptides are further provided by this invention. The polypeptides and polypeptide compositions also are useful to raise antibodies that in turn have diagnostic and therapeutic utility. The antibodies are provided alone or in combination with a carrier such as a pharmaceutically acceptable carrier for therapeutic or diagnostic application. Portions of these antibodies are also provided that include, but are not limited to, an intact antibody molecule, a single chain variable region (ScFv), a monoclonal antibody, a polyclonal antibody, a chimeric antibody, a humanized antibody, a veneered antibody or a human antibody. Methods to raise antibodies are also provided herein. The antibodies can be generated in any appropriate in vitro or in vivo system, e.g., in cell culture, in phage, or in various animals, including but not limited to cows, rabbits, goats, mice, rats, hamsters, guinea pigs, sheep, dogs, cats, monkeys, chimpanzees, apes, etc., using techniques known in the art such as Multiple Antigenic Peptides, described herein.

Also provided are isolated polynucleotides that encode the polypeptides shown in Table 1, alone or in combination with a carrier for delivery or expression of the polynucleotides. The polynucleotides can be optionally bound to a detectable label. Examples of such polynucleotides are shown in Table 2. As known to those skilled in the art, the degeneracy of the genetic code provides several polynucleotide sequences that encode the same polypeptide. In one aspect, the polynucleotide is inserted into and contained within a host cell. In a further aspect, the polynucleotide is modified and/or amplified. In yet a further aspect, the polynucleotides are isolated from the host cells.

TABLE 2

| SEQ ID NO. | EXEMPLAR OF NUCLEOTIDE SEQUENCE |
|---|---|
| 9 | gctcgagcagtgattatgtttgccaatgaggatgacatcaggaggatattggaagcagcaaaaaaactaaaccaaagtggccatttctctggattggctcagatagttggggatccaaaatagcacctgtctatcagcaagaggagattgcagaagggctgtgacaattttgcccaaacgagcatcaattgatggatttgatcaatactttagaagccaaactcttgccaataatcgaagaaatgtgtggtttgcagaattttgggaggagaattttggctgcaagttaggatcacatgggaaaggaacagtcatataaagaaatgcacagaaaatgtccctgtgactgatttctttgtgggaccagtctgcatcattcctaagactgacacaaagccccgctcgagcgtgtgggatgaacggcatgactcacacattcccctggaggactgcaggttt |
| 10 | gcnmgngcngtnathatgttygcnaaygargaygayathmgnmgnathytngargcngcnaaraarytnaaycarwsnggncayttyytntggathggnwsngaywsntggggnwsnaarathgcnccngtntaycarcargargarathgcngarggngcngtnacnathytnccnaarmgngcnwsnathgaygnttygaycartayttymgnwsncaracnytngcnaayaaymgnmgnaaygtntggttygcngarttytgggargaraayttyggntgyaarytnggnwsncayggnaarmgnaaywsncayathaaraartgyacngaraaygtncngtnacngayttyttygtnggncngtntgyathathccnaaracngayacnaarccnmgnwsnwsngtntgggaygarmgncaygaywsncayathccnytngargaytgymgntty |

TABLE 2-continued

| SEQ ID NO. | EXEMPLAR OF NUCLEOTIDE SEQUENCE |
|---|---|
| 11 | gcagtgattatgtttgccaatgaggatgacatcagg |
| 12 | gcngtnathatgttygcnaaygargaygayathmgn |
| 13 | gcatcaattgatggatttgatcaatactttagaagccaaactcttgccaataatcga |
| 14 | gcnwsnathgayggnttygaycartayttymgnwsncaracnytngcnaayaaymgn |
| 15 | gcatcaattgatggatttgatcaatactttaga |
| 16 | gcnwsnathgayggnttygaycartayttymgn |
| 17 | tgcacagaaaatgtccctgtgactgatttctttgtgggaccagtctgcatcattcctaag |
| 18 | tgyacngaraaygtnccngtnacngayttyttygtnggnccngtntgyathathccnaar |
| 19 | tcgagcgtgtgggatgaacggcatgactcacacattccctggaggactgcagg |
| 20 | wsnwsngtntgggaygarmgncaygaywsncayathccnytngargaytgymgn |
| 21 | catgactcacacattccctggaggactgcagg |
| 22 | caygaywsncayathccnytngargaytgymgn |
| 23 | gcatcaattgatggatttgatcaatactttagaagccaaactcttgccaataatcgaagaaatgtgtggtttgcagaattttgggaggagaattttggctgcaagttaggatcacatgggaaaaggaacagtcatataaagaaatgcacagaaaatgtccctgtgactgatttctttgtgggaccagtctgcatcattcctaagactgacacaaagcccgctcgagcgtgtgggatgaacggcatgactcacacattccctggaggactgcagg |
| 24 | gcnwsnathgayggnttygaycartayttymgnwsncaracnytngcnaayaaymgnmgnaaygtntggttygcngarttyttgggargaraayttyggntgyaarytnggnwsncayggnaarmgnaaywsncayathaaraartgyacngaraaygtnccngtnacngayttyttygtnggnccngtntgyathathccnaaracngayacnaarccnmgnwsnwsngtntgggaygarmgncaygaywsncayathccnytngargaytgymgn |

The nucleotide symbols of Table 2 indicate the following: a=Adenine; c=Cytosine; g=Guanine; t=Thymine; u=Uracil; r=Guanine/Adenine; y=Cytosine/Thymine; k=Guanine/Thymine; m=Adenine/Cytosine; s=Guanine/Cytosine; w=Adenine/Thymine; b=Guanine/Thymine/Cytosine; d=Guanine/Adinine/Thymine; h=Adenine/Cytosine/Thymine; v=Guanine/Cytosine/Adenine; n=Adenine/Guanine/Cytosine/Thymine.

This invention also provides compositions containing a polypeptide, a polynucleotide an antibody, an antibody fragment or derivative, in combination with a carrier such as a pharmaceutically acceptable carrier. The compositions can be used in methods to diagnose, monitor and/or treat disorders associated with neurodegenerative disorders such as Alzheimer's disease, Down's Syndrome, mild cognitive impairment, stroke, focal ischemia associated dementia, and neuronal degeneration. Thus, in one aspect, this invention provides methods to bind a neuronal receptor by administering an effective amount of an antibody, antibody portion or derivative thereof, of this invention. These can optionally be bound to a detectable label.

Yet another aspect of the invention is a method to identify a binding ligand involved in neuronal degeneration. A test compound or agent such as an antibody or antibody derivative is contacted with a polypeptide or antibody or fragment thereof under conditions that favor the formation of binding to the polypeptide, antibody or fragment thereof. Ligand binding, if it occurred, is then detected. A test compound or agent which binds to the protein is identified as a therapeutic or diagnostic agent.

Applicants also provide methods and kits for determining whether a patient will be suitably treated by one or more of the therapies described herein. The method requires identifying and/or determining if a polypeptide or polynucleotide of this invention is present in a patient sample. If present, that patient is a candidate for use of the therapeutic compositions described herein. Additionally, kits for performance of the assays are provided. These kits contain at least one composition of this invention and instructions for use.

The polynucleotides, polypeptides, antibodies and compositions of the present invention can be used in the manufacture of medicaments for the treatment of humans and other animals by administration in accordance with conventional procedures, such as an active ingredient in pharmaceutical compositions.

Applicants have identified a novel receptor that is expressed on neuronal cells in a developmentally-specific manner. Accordingly, this invention provides antibodies that bind to polypeptides comprising one or more of the sequences identified in Table 1, or equivalent polypeptides having a predetermined sequence homology or identity to the specific sequences identified in Table 1 as provided herein.

Portions of these antibodies are also provided that include, but are not limited to, an intact antibody molecule, a single chain variable region (ScFv), a monoclonal antibody, a polyclonal antibody, a chimeric antibody, a humanized antibody, a veneered antibody or a human antibody. Also provided are antibody-peptide complexes comprising an antibody described herein and a polypeptide that specifically binds to the antibody. Methods to raise antibodies are also provided herein. The antibodies can be generated in any appropriate in vitro or in vivo system, e.g., in cell culture, in phage, or in various animals, including but not limited to cows, rabbits, goats, mice, rats, hamsters, guinea pigs, sheep, dogs, cats, monkeys, chimpanzees, apes, etc, using techniques known in the art such as Multiple Antigenic Peptides, described herein.

Also provided are hybridoma cells and methods of generating the same, which produce the antibodies of the invention.

Also provided are isolated polynucleotides that encode the polypeptides shown in Table 1, alone or in combination with a carrier for delivery or expression of the polynucleotides. The polynucleotides can be optionally bound to a detectable label. Examples of such polynucleotides are shown in Table 2. As known to those skilled in the art, the degeneracy of the genetic code provides several polynucleotide sequences that encode the same polypeptide. In one aspect, the polynucleotide is inserted into and contained within a host cell. In a further aspect, the polynucleotide is modified and/or amplified. In yet a further aspect, the polynucleotides are from the host cells.

The compositions can be used in methods to diagnose, monitor and/or treat disorders associated with neurodegenerative disorders such as Alzheimer's disease, Down's Syndrome, mild cognitive impairment, stroke, focal ischemia associated dementia, and neuronal degeneration. Thus, in one aspect, this invention provides methods to bind a neuronal receptor by administering an effective amount of an antibody, antibody portion or derivative thereof, of this invention. These can optionally be bound to a detectable label.

Yet another aspect of the invention is a method to identify a binding ligand involved in neuronal degeneration. A test compound or agent such as an antibody or antibody derivative is contacted with a polypeptide or antibody or fragment thereof under conditions that favor the formation of binding to the polypeptide, antibody or fragment thereof. Ligand binding, if it occurred, is then detected. A test compound or agent which binds to the protein is identified as a therapeutic or diagnostic agent.

Applicants also provide methods and kits for determining whether a patient will be suitably treated by one or more of the therapies described herein. The method requires identifying and/or determining if a polypeptide or polynucleotide of this invention is present in a patient sample. If present, that patient is a candidate for use of the therapeutic compositions described herein. Additionally, kits for performance of the assays are provided. These kits contain at least one composition of this invention and instructions for use.

The antibodies and compositions of the present invention can be used in the manufacture of medicaments for the treatment of humans and other animals by administration in accordance with conventional procedures, such as an active ingredient in pharmaceutical compositions.

Applicants have identified a novel receptor that is expressed on neuronal cells in a developmentally-specific manner. Accordingly, this invention provides antibodies that bind to polypeptides comprising one or more of the sequences identified in Table 1, or equivalent polypeptides having a predetermined sequence homology or identity to the specific sequences identified in Table 1 as provided herein.

These polypeptides and compositions thereof are useful to raise antibodies that in turn have diagnostic and therapeutic utility. The antibodies are provided alone or in combination with a carrier such as a pharmaceutically acceptable carrier for therapeutic or diagnostic application. Portions of these antibodies are also provided that include, but are not limited to, an intact antibody molecule, a single chain variable region (ScFv), a monoclonal antibody, a polyclonal antibody, a chimeric antibody, a humanized antibody, a veneered antibody or a human antibody. Also provided are antibody-peptide complexes comprising an antibody described herein and a polypeptide that specifically binds to the antibody. Methods to raise antibodies are also provided herein. The antibodies can be generated in any appropriate in vitro or in vivo system, e.g., in cell culture, in phage, or in various animals, including but not limited to cows, rabbits, goats, mice, rats, hamsters, guinea pigs, sheep, dogs, cats, monkeys, chimpanzees, apes, etc, using techniques known in the art such as Multiple Antigenic Peptides, described herein.

Also provided are hybridoma cells and methods of generating the same, which produce the antibodies of the invention.

Also provided are isolated polynucleotides that encode the polypeptides shown in Table 1, alone or in combination with a carrier for delivery or expression of the polynucleotides. The polynucleotides can be optionally bound to a detectable label. Examples of such polynucleotides are shown in Table 2. As known to those skilled in the art, the degeneracy of the genetic code provides several polynucleotide sequences that encode the same polypeptide. In one aspect, the polynucleotide is inserted into and contained within a host cell. In a further aspect, the polynucleotide is modified and/or amplified. In yet a further aspect, the polynucleotides are from the host cells.

The compositions can be used in methods to diagnose, monitor and/or treat disorders associated with neurodegenerative disorders such as Alzheimer's disease, Down's Syndrome, mild cognitive impairment, stroke, focal ischemia associated dementia, and neuronal degeneration. Thus, in one aspect, this invention provides methods to bind a neuronal receptor by administering an effective amount of an antibody, antibody portion or derivative thereof, of this invention. These can optionally be bound to a detectable label.

Yet another aspect of the invention is a method to identify a binding ligand involved in neuronal degeneration. A test compound or agent such as an antibody or antibody derivative is contacted with a polypeptide or antibody or fragment thereof under conditions that favor the formation of binding to the polypeptide, antibody or fragment thereof. Ligand binding, if it occurred, is then detected. A test compound or agent which binds to the protein is identified as a therapeutic or diagnostic agent.

Applicants also provide methods and kits for determining whether a patient will be suitably treated by one or more of the therapies described herein. The method requires identifying and/or determining if a polypeptide or polynucleotide of this invention is present in a patient sample. If present, that patient is a candidate for use of the therapeutic compositions described herein. Additionally, kits for performance of the assays are provided. These kits contain at least one composition of this invention and instructions for use.

The antibodies and compositions of the present invention can be used in the manufacture of medicaments for the treatment of humans and other animals by administration in accordance with conventional procedures, such as an active ingredient in pharmaceutical compositions.

BRIEF DESCRIPTION OF THE FIGURES

FIG. 2 shows the identified ADDL binding epitopes sequence alignment with rat and human homologues. Blocks of similar residues are highlighted with gray bars. The Genbank accession numbers indicate the following: NP_071538—the glutamate receptor metabotropic 8 from *Rattus Norvegicus*; EDM15189—glutamate receptor metabotropic 8, isoform CRA_a from *Rattus Norvegicus*; EAW83623—glutamate receptor metabotropic 8, isoform CRA_c from *Homo sapiens*; EAL24322—glutamate receptor metabotropic 8, from *Homo sapiens*; XP_377945—PREDICTED similar to glutamate receptor metabotropic 8, from *Homo sapiens*; XP_940616—PREDICTED similar to glutamate receptor metabotropic 8, from *Homo sapiens*; sequences from Table 4.

FIG. 3 shows a sequence alignment of identified peptides with the extracellular fragments of rat metabotropic glutamate receptors (mGluR4, mGluR6, mGluR7, and mGluR8) and the predicted genomic sequence XP_377945. Respective amino acid positions within the full length sequence are shown within parenthesis. Trypsin cleavage sites (R and K) are boxed in solid black lines. Conserved amino acid residues within the peptide fragments of CTENVPVTDFFVGPVCIIPK (SEQ ID NO. 5) and SSVWDERHDSHIPLEDCR (SEQ ID NO. 6) are boxed in dotted lines.

FIG. 4, panels A to C, show ADDL binding to primary E18 rat embryonic hippocampus cells. ADDL binding was detected by immunofluorescences using an ADDL selective antibody ACU954. Cells following 7 days of in vitro culture (A), 14 days of in vitro culture (B), and 21 days of in vitro culture (C) were exposed to 5 nM of $A\beta_{1-42}$ that was allowed to assemble into ADDLs on the cells.

DETAILED DESCRIPTION OF THE INVENTION

Figure 1:
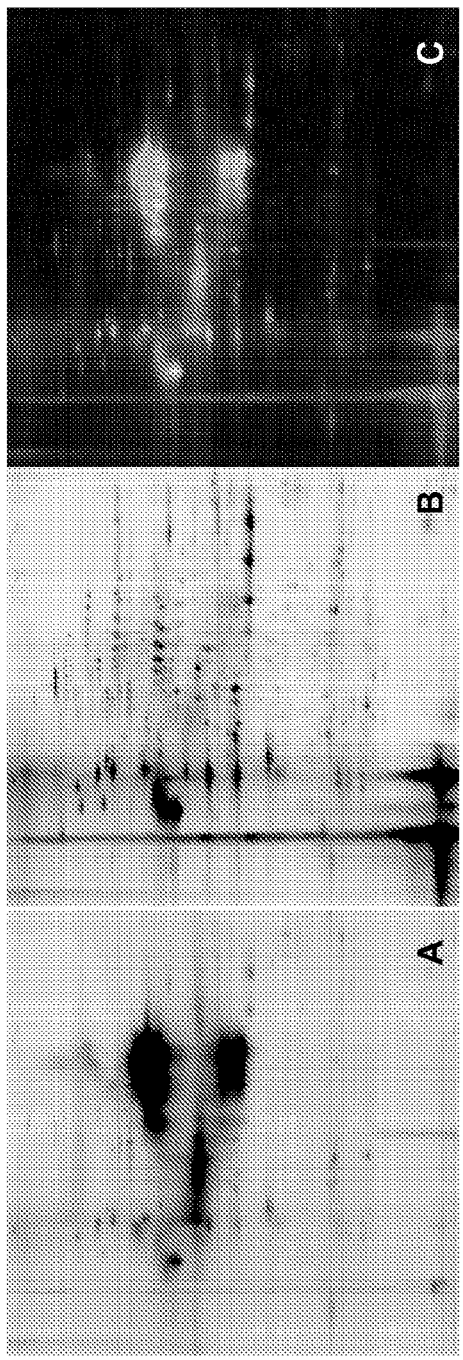
FIG. 1, panels A to C, show 2-Dimensional Differential In-Gel Electrophoresis (2-D DIGE) of polypeptides that binds to ADDL. (A) Vehicle control gel shows unspecific immunoprecipitation of proteins interacting with streptavidin beads. (B) ADDL treated sample shows differentially migrated proteins. (C) Shows an overlay of A and B.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

DEFINITIONS

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "receptor" refers to a protein or polypeptide typically found on the cell membrane, within the cytoplasm, or cell nucleus that binds to a specific molecule (e.g. a ligand) and initiates the cellular response to the molecule. Such a response includes those associated with, but are not limited to, peripheral membrane protein receptors, transmembrane receptors, metabotropic receptors, G protein-coupled receptors, receptor tyrosine kinases, guanylyl cyclase receptors, ionotropic receptors, and transcription factors. However, in the absence of, for example, a cell membrane such as conditions typically found in vitro, a receptor peptide may still initiate a response to the binding of a molecule. In one embodiment, a receptor polypeptide specifically recognizes and binds soluble ADDL.

The terms "binding," "binds," "recognition," or "recognize" as used herein are meant to include interactions between molecules that may be detected using, for example, a hybridization assay. The terms are also meant to include "binding" interactions between molecules. Interactions may be, for example, protein-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

The term "ADDL" is conventionally defined as amyloid beta-derived diffusible ligands which have the following characteristics: soluble, oligomeric, globular, non-fibrillar, neurotoxic $A\beta_{1-42}$ peptides (GenBank Ref. No. IZOQ_A, accessed on Nov. 21, 2007).

The term "soluble" means the ability for a given substance, the solute (an example in the instant invention is the $A\beta_{1-42}$ oligomer) to dissolve in a solvent. Within the context of the instant invention, soluble $A\beta$ oligomers are capable of being fractionated by centrifugation.

The term "oligomeric" means a protein complex of a finite number of monomer subunits. In the context of the invention, oligomers are referred to as trimers, low-n-mers, dodecamers (12-mers), and large-n-multimers composed of $A\beta_{1-42}$ peptides. The term "oligomeric" does not include senile amyloid plaques.

The term "globular" means a large soluble protein complex, which is to be distinguished from fibrils and amyloid plaques. Preferably, the globular structure ranges in size from 4 nanometers (nm) to about 12 nm, preferably, from about 4.7 to about 11 nm, which can be observed upon atomic force microscope analysis (AFM) of supernatant fractions of $A\beta_{1-42}$ soluble oligomer preparations as described in U.S. Pat. No. 6,218,506.

The term "non-fibrillar" means the $A\beta_{1-42}$ peptides and oligomeric complexes that are not aligned in a morphologically distinct pattern known as amyloid protofibrils or amyloid fibrils.

The term "ligand" refers to a biological or chemical molecule that is able to bind to and form a complex with a biomolecule to serve a biological purpose. In one embodiment, a ligand is an effector molecule binding to a site on a target protein, by intermolecular forces such as ionic bonds, hydrogen bonds and Van der Walls forces. This association is typically reversible. A non-limiting example is when a ligand binds to a receptor, thereby altering the chemical conformation, i.e. the three dimensional shape of the receptor protein. The conformational state of the receptor protein determines the functional state of the receptor.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

The phrase "biologically equivalent polypeptide" refers to protein or polynucleotide which hybridizes to the exemplified polynucleotide under stringent conditions and which exhibit similar biological activity in vivo, e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively more than 75%, or alternatively, more than 80%, or alternatively, more than 85%, or alternatively, more than 90%, or alternatively, more than 95%, or alternatively more than 97%, or alternatively, more than 98 or 99% sequence homology. Percentage homology can be determined by sequence comparison using programs such as BLAST run under appropriate conditions. In one aspect, the program is run under default parameters.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethan-olamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carb-oxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylgly-cerol (DPPG), dioleoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs).

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information, last accessed on Nov. 26, 2007. Biologically equivalent polynucleotides are those having the specified percent homology and encoding a polypeptide having the same or similar biological activity.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "non-contiguous" refers to the presence of an intervening peptide, nucleotide, polypeptide or polynucleotide between a specified region and/or sequence. For example, two polypeptide sequences are non-contiguous because the two sequences are separated by a polypeptide sequences that is not homologous to either of the two sequences. Non-limiting intervening sequences are comprised of at least a single peptide or nucleotide.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

"RNA interference" (RNAi) refers to sequence-specific or gene specific suppression of gene expression (protein synthesis) that is mediated by short interfering RNA (siRNA).

"Short interfering RNA" (siRNA) refers to double-stranded RNA molecules, generally, from about 10 to about 30 nucleotides long that are capable of mediating RNA interference (RNAi). As used herein, the term siRNA includes short hairpin RNAs (shRNAs).

A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

Applicants have provided herein the polypeptide and/or polynucleotide sequences for use in gene transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions.

A "gene delivery vehicle" is defined as any molecule that can carry inserted polynucleotides into a host cell. Examples of gene delivery vehicles are liposomes, micells biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells or cardiomyocytes. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

A "probe" when used in the context of polynucleotide manipulation refers to an oligonucleotide that is provided as a reagent to detect a target potentially present in a sample of interest by hybridizing with the target. Polynucleotide probes of the invention range in length from about 10 to 5,000 nucleotides. In one aspect, the probe is at least 10 nucleotides, or alternatively, at least 20 nucleotides, or alternatively, at least 30 nucleotides or alternatively, at least 50 nucleotides, or alternatively, at least 75, or alternatively, at least 100 nucleotides, or alternatively, at least 200 nucleotides, or alternatively, at least 500 nucleotides, or alternatively, at least 1000 nucleotides, or alternatively, at least 2000 nucleotides, or alternatively, at least 3000 nucleotides, or alternatively, at least 5000 nucleotides. Usually, a probe will comprise a detectable label or a means by which a label can be attached, either before or subsequent to the hybridization reaction. Alternatively, a "probe" can be a biological compound such as a polypeptide, antibody, or fragments thereof that is capable of binding to the target potentially present in a sample of interest.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as "replication." A primer can also be used as a probe in hybridization reactions, such as Southern or Northern blot analyses. Sambrook and Russell (2001), supra. Primers of the instant invention are comprised of nucleotides ranging from 17 to 30 nucleotides. In one aspect, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions and can be prepared using the polynucleotide sequences provided herein. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "propagate" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

A "composition" is intended to mean a combination of active polypeptide, polynucleotide or antibody and another compound or composition, inert (e.g. a detectable label) or active (e.g. a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are arrayed on a gene chip for determining the DNA sequence by the hybridization approach, such as that outlined in U.S. Pat. Nos. 6,025,136 and 6,018,041. The polynucleotides of this invention can be modified to probes, which in turn can be used for detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarrays" and similar technologies are know in the art. Examples of such include, but are not limited to, LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarrying system that can dispense from 12 to 64 spots onto multiple glass slides (Intelligent Bio-Instruments); Molecular Biology Workstation and NanoChip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "gene chips" or a "microarrays" are also described in U.S. Patent Publ. Nos.: 2007-0111322, 2007-0099198, 2007-0084997, 2007-0059769 and 2007-0059765 and U.S. Pat. Nos. 7,138,506, 7,070,740, and 6,989,267.

In one aspect, "gene chips" or "microarrays" containing probes or primers homologous to a polynucleotide, polypeptide or antibody described herein are prepared. A suitable sample is obtained from the patient, extraction of genomic DNA, RNA, protein or any combination thereof is conducted and amplified if necessary. The sample is contacted to the gene chip or microarray panel under conditions suitable for hybridization of the gene(s) or gene product(s) of interest to the probe(s) or primer(s) contained on the gene chip or microarray. The probes or primers may be detectably labeled thereby identifying the gene(s) of interest. Alternatively, a chemical or biological reaction may be used to identify the probes or primers which hybridized with the DNA or RNA of the gene(s) of interest. The genotypes or phenotype of the patient is then determined with the aid of the aforementioned apparatus and methods.

Other non-limiting examples of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

A "subject," "individual" or "patient" is used interchangeably herein, and refers to a vertebrate, preferably a mammal, more preferably a human. Mammals include, but are not limited to, marines, rats, rabbits, simians, bovines, ovines, porcines, canines, felines, farm animals, sport animals, pets, equines, and primates, particularly humans.

"Cell," "host cell" or "recombinant host cell" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "control" is an alternative subject or sample used in an experiment for comparison purpose. A control can be "positive" or "negative". For example, where the purpose of the experiment is to determine a correlation of an altered level of ADDLs with a particular phenotype, it is generally preferable to use a positive control (a subject or sample from a subject, suffering from a disease associated with ADDL formation), and a negative control (a subject or a sample from a subject not suffering from or predisposed to a disease associated with ADDL formation).

The terms "disease," "disorder," and "condition" are used inclusively and refer to any condition mediated at least in part by ADDLs. In the context of this invention the disease may be associated with insoluble amyloid fibrils, senile plaques, neurofibrillary tangles, and/or the over-expression of amyloid $\beta_{1-42}$ protein and/or ADDL receptor. Examples include, but are not limited to, Alzheimer's disease, Down's syndrome, mild cognitive impairment, stroke, focal ischemia associated dementia, and neuronal degeneration. Patients amenable to treatment include individuals at risk of disease but not exhibiting symptoms, as well as patients presently exhibiting symptoms. Therefore, a polynucleotide, polypeptide, antibody or composition described herein can be administered prophylactically to the general population without the need for any assessment of the risk of the patient.

The methods are especially useful for individuals who have a known genetic risk of Alzheimer's disease. Such individuals include those having relatives who have been diagnosed with the disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of Alzheimer's disease, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have Alzheimer's disease. These include measurement of CSF tau as described in Vandermeeren et al. (1993) J. Neurochem. 61:1828-1834; Arai et al. (1995) Ann. Neurol. 38:649-652; and Jansen et al. (1995) Neurosci. Lett. 186:189-191 and $A\beta_{1-42}$ levels as described in Andreasen et al. (1999) Arch. Neurol. 56:673-680; Vanderstichele et al., "Development of a specific diagnositic test for measurement of β-amyloid1-42 in CSF", *Progress in Alzheimer's and Parkinson's diseases*, Fisher et al. (eds), New York, Plenum, pgs. 773-778; and Hulstaert et al. (1999) Neurology 52:1555-1562. Individuals suffering from Alzheimer's disease can also be diagnosed by NINCDS-ADRDA (National Institute of Neurological and Communicative Diseases and Stroke/Alzheimer's Disease and Related Disorders Association) criteria as described in Hogervorst et al. "Diagnosing dementia: Interrater Reliability Assessment and Accuracy of the NINCDS/ADRDA Criteria versus CERAD Histopathological Criteria for Alzheimer's Disease" University of Oxford, Oxford Project to Investigate Memory and Aging (OPTIMA), Oxford, UK; and McKhann et al. (1984) Neurology 34(7):939-944 or the method disclosed herein.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time. Treatment can be monitored by assaying for the presence of ADDLs or ADDL receptors over time.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

The term "suffering" as it related to the term "treatment" refers to a patient or individual who has been diagnosed with or is predisposed to a disease. A patient may also be referred to being "at risk of suffering" from a disease. This patient has not yet developed characteristic disease pathology, however are know to be predisposed to the disease due to family history, being genetically predispose to developing the disease, or diagnosed with a disease or disorder that predisposes them to developing the disease to be treated.

In addition to Alzheimer's disease, several other disease are know to be associated with $A\beta_{1-42}$ formation including, but are not limited to, Down's Syndrome, stroke and mild cognitive impairment. It is conceivable that similar to Alzheimer's disease, treatment of patients suffering from or at risk of suffering from these diseases is possible due to the parallel mechanisms of the diseases.

Similarly, over-expression of $A\beta_{1-42}$ is associated with focal ischemia associated dementia and neuronal degeneration. Over-expression of $A\beta_{1-42}$ is believed to result in accumulation of ADDLs, thereby inducing neurotoxicity. Treating a patient suffering from or at risk of suffering from one of these diseases by administration of one or more of a polynucleotide, polypeptide, antibody or composition described herein will ameliorate the neurotoxicity of over-expressed $A\beta_{1-42}$.

The term "senile plaque" or "senile plaque formation" refers to the extracellular deposit of amyloid in the gray matter of the brain. The deposits are associated with degenerative neural structures. It is understood that senile plaque is different from and distinguished over ADDLs.

The term "neurotoxicity" refers to the toxic effect of ADDLs on neuronal cells either in vitro and/or in vivo. ADDLs bind to specific neuronal receptors triggering aberrant neuronal signaling, which compromises long term potentiation and causes memory deficits. Thus, ADDLs alter the function of the neuronal cell in such a manner that, while still viable, the neuron does not properly function. Such altered functionality is referred to herein as "neuronal dysfunction," which is a subclass of neurotoxicity. Persistent ADDL signaling causes aberrant transcription and the progressive loss of synapses, and very long term persistent ADDL signaling and accumulated structural pathology leads to eventual neuron death and gross brain dystrophy.

The neurotoxic effects of ADDLs in a patient suffering from an ADDL associated disease or disorder can result in diminished cognitive function. The term "cognitive function" refers to the intellectual process by which one becomes aware of, perceives, or comprehends ideas. Cognitive function embraces the quality of knowing, which includes all aspects of perception; recognition; conception; sensing; thinking; reasoning; remembering and imagining.

The term "diminished cognitive function" refers to memory loss, mental slowing, intellectual decline and/or amnesia. Memory loss may be characterized as the difficulty or failure for immediate or delayed recall. Mental slowing is the difficulty in processing or completing previously learned tasks in a timely manner or in processing new information quickly. Intellectual decline is defined as a loss of information, or an inability to utilize information previously possessed or utilized by a person. Amnesia is an extreme loss of cognitive ability which results in partial or total inability to recall past experiences and impaired or total loss of the ability to speak or write. Diminished cognitive function may be caused by a number of disease conditions which are more thoroughly discussed below.

Methods of assessing cognitive function include, but are not limited to, standardized instruments for example Folstein Mini-Mental State Examination; Modified Mini-Mental State Exam; Middlesex Elderly Assessment of Mental State; Short Portable Mental Status Questionnaire; Alzheimer's Disease Assessment Scale; Clock Drawing Test; Clinical Dementia Rating; Neuropsychiatric Inventory or any similarly designed test. Using the above listed tests, a skilled clinician would be able to assess the level of diminished cognitive function of a patient or enhanced cognitive function following treatment. Additionally, informal observations and interactions of individuals to a patient can also be used to assess cognitive function and include, but are not limited to, family members, friends, formal care givers such as nurses, and individuals who have previous intimate knowledge of the patient.

As previously described, for example in WO 01/10900 (PCT/US00/21458) assays can be carried out so as to identify compounds that modulate (i.e., either facilitate or block) binding to a cell surface protein of ADDLs or ADDL mediated downstream signaling. In such assays, a test compound is added to the ADDL preparation, prior to the contacting of the cells with the ADDLs. Also, a test compound can be added to the mixture of cells plus ADDLs. The specificity of the compounds for acting on ADDL binding to a cell-surface receptor or an ADDL-mediated downstream effect can be confirmed, for instance, by simply adding the test compound in the absence of any co-incubation with ADDLs. Of course, further appropriate controls, as known to those skilled in the art, should be included with all assays.

For instance, when 20 nL of an ADDL preparation was injected into the hippocampal region of an adult mouse 60-70 minutes prior to the conduct of a long-term potentiation (LTP) experiment, the stimulation phase of the experiment occurred in a manner identical with saline control injections, but the consolidation phase showed a significant continuing decline in synaptic activity as measured by cell body spike amplitude described by Namgung et al. (1995) Brain Research 689:85-92. Over the subsequent 2 hours, compared with control animals, synaptic activity remained at a level comparable to that exhibited during the stimulation phase. Analysis of brain slices after the experiment indicated that no cell death had occurred. Conducting similar experiments, treating the adult mouse with (i) an ADDL preparation plus a test compound, (ii) only the test compound, and (iii) control buffer solution (e.g., saline solution, neurobasal media, etc.) and comparing the results of these experiments upon LTP with those of the ADDL only treatment experiment will identify compounds that modulate binding to a cell surface protein of ADDLs or ADDL mediated downstream signaling.

Other signaling assays well known to those skilled in the art can be conducted in an analogues manner to identify compounds that modulate the binding to a cell surface protein of ADDLs or ADDL mediated downstream signaling. Such signaling assays include, but are not limited to, ADDL induce rapid complex formation between Fyn and focal adhesion kinase (Zhang et al. (1996) Neurosci. Letters 211:14); translocation of several phosphorylated proteins and Fyn-Fak complex to a Triton-insoluble fraction (Berg et al. (1997) J. Neurosci. Res. 50:979-989); ADDL induced tau-phosphorylation (De Felice et al. (2008) Neurobiol Aging 29(9):1334-1347); or ADDL induced Akt pSer473 phosphorylation (Zhao et al. (2007) FASEB J., *Epub ahead of print*, doi: 10.1096/fj.06-7703com).

A "neuronal cell" or "neuron" is a cell that transmits and processes signals in the brain or other parts of the nervous system. Additionally, a neuronal cell, as used in the invention, can be isolated from subject brain tissue and grown in tissue culture. Alternatively, isolated cells can be comprised of an established neuronal cell line selected from for example, but are not limited to, MC65; HCN-2; SH-SY5Y; SK-N-AS; SK-N-FI; SK-N-DZ; H19-7/IGF-IR; QNR/D; QNR/K2; C8-D30; C8-S; C8-D1A; OLGA-PH-J/92; Daoy; RSC96; SW10; RT4-D6P2T; RN33B; PC-12; DBRTG-05MG; C8-B4; SK-N-SH; B35; R3[33-10ras3]; Neuro-2A; and HCN-1A or any genetic, chemical, and/or biochemical modified variants thereof (Commercially available from American Type Culture Collection (ATCC)). The isolated cells can also be comprised of primary cells and/or astrocytes isolated from neuronal tissues selected from, for example, but are not limited to, the hippocampus; cerebellum; cortex; hypothalamus; mid-brain; spinal cord; striatum; frontal lobe; temporal lobe; parietal lobe; occipital lobe and any genetic, chemical, and/or biochemical modified variants thereof. The isolated, cultured cell can be comprised of a neural stem cell or any differentiated, genetic, chemical, and/or biochemical modified variants thereof. Additionally, a neuronal cell or neuron can be isolated and distinguished from other cell types by detecting expression of neuronal markers selected from, but not limited to, CD 133, GFAP, MAP-2, MPB, Nestin, Neural tubulin, Neurofilament, Neurosphere, Noggin, O4, O1, Synaptophysin, and Tau (http://stemcells.nih.gov/info/scireport/appendixE.asp, accessed on Nov. 26, 2007).

As used herein, the term "neuronal tissue" refers to any portion of the central nervous system including, but not limited to, the brain or spinal cord. Neuronal tissue can be composed of, at least in part, neuronal cells.

The term "amyloid fibrils" means protein aggregates sharing specific structural traits. Histopathological techniques generally identify the structures by apple-green birefringence when stained with Congo red and seen under polarized light.

The term "tangles" means the neurofibrillary tangles formed inside of degenerating neurons by bundling of paired helical filaments, which assemble from hyperphosphorylated forms of the microtubule-associated protein know as tau.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "bispecific molecule" is intended to include any agent, e.g., a protein, peptide, or protein or peptide complex, which has two different binding specificities.

The term "multispecific molecule" or "heterospecific molecule" is intended to include any agent, e.g. a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, "isotype" refers to the antibody class (e.g., IgM or IgG1) that is encoded by heavy chain constant region genes.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

In another aspect, the fluorescent label is functionalized to facilitate covalent attachment to a cellular component present in or on the surface of the cell or tissue such as a cell surface marker. Suitable functional groups, including, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Descriptive Embodiments

Isolated Polypeptides and Compositions

This invention provides isolated novel polypeptides that correspond to a receptor and/or a receptor complex expressed on neuronal cells. In one aspect, the receptor and complex are expressed on neuronal cells in a developmentally specific manner. The polypeptides are useful diagnostically and therapeutically to diagnose and treat neurodegenerative disorders associated with the expression of the receptor in a subject and ADDL binding to the receptor.

Thus, in one aspect this invention provides an isolated receptor polypeptide comprising the amino acid sequence ARAVIMFANEDDIRRILEAAKKLNQSGH-FLWIGSDSWGSKIAPVYQQEEIAEGAVTI LPKRASIDGFDQYFRSQTLANNRRNVW-FAEFWEENFGCKLGSHGKRNSHIKKCTE NVPVTD-FFVGPVCIIPKTDTKPRSSVWDERHDSHIPLEDCRF (SEQ ID NO. 1) or a polypeptide substantially homologous and biologically equivalent to SEQ ID NO. 1. Substantially homologous and biologically equivalent polypeptides intend those having at least 80% homology, or alternatively at least 85% homology, or alternatively at least 90% homology, or alternatively, at least 95% homology or alternatively, at least 98% homology to SEQ ID NO. 1, each as determined using methods known to those skilled in the art and identified herein, when run under default parameters.

Another aspect of this invention is an isolated receptor polypeptide comprising two non-contiguous binding regions (epitopes), wherein the epitopes comprise the amino acid sequences ASIDGFDQYFRSQTLANNR (SEQ ID NO. 3) and SSVWDERHDSHIPLEDCR (SEQ ID NO. 6), or amino acid sequences substantially homologous and biologically equivalent to these polypeptides. Substantially homologous and biologically equivalent polypeptides intend polypeptides having at least 60%, or alternatively at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 3 and 6, each as determined using methods known to those skilled in the art and identified herein, when run under default parameters.

Also provided by this invention is an isolated receptor polypeptide comprising the amino acid sequence ASIDG-FDQYFRSQTLANNRRNVWFAEFWEENF-GCKLGSHGKRNSHIKKCTENVPV TDFFVGPVCIIPKT-DTKPRSSVWDERHDSHIPLEDCR (SEQ ID NO. 8) or an amino acid sequence substantially homologous and biologically equivalent to SEQ ID NO. 8. Substantially homologous and biologically equivalent polypeptides intend those having at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NO. 8, each as determined using methods known to those skilled in the art and identified herein, when run under default parameters.

Further provided by this invention is an isolated receptor complex that comprises a plurality of polypeptides having two or more non-contiguous amino acid sequences of the group:

```
AVIMFANEDDIR;              (SEQ ID NO. 2)

ASIDGFDQYFRSQTLANNR;       (SEQ ID NO. 3)

ASIDGFDQYFR;               (SEQ ID NO. 4)

CTENVPVTDFFVGPVCIIPK;      (SEQ ID NO. 5)

SSVWDERHDSHIPLEDCR;        (SEQ ID NO. 6)
or

HDSHIPLEDCR.               (SEQ ID NO. 7)
```

Yet further provided is an isolated receptor complex having one or more polypeptides having varying degrees of sequence identity or homology to one or more of SEQ ID NOS. 2 through 7, e.g., at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NOS. 2 through 7, each as determined using methods known to those skilled in the art and identified herein, when run under default parameters.

This invention also provides an isolated receptor complex comprising two or more non-contiguous amino acids that in turn comprise at least the amino acid sequences ASIDG-FDQYFR (SEQ ID NO. 4) and HDSHIPLEDCR (SEQ ID NO. 7), or amino acids substantially homologous and biologically equivalent to SEQ ID NOS. 4 and 7. Substantially homologous and biologically equivalent polypeptides intend those have varying degrees of homology to SEQ ID. NOS. 4 and/or 7, e.g., polypeptide having at least 65% homology, or alternatively at least 70% homology, or alternatively at least 75% homology, or alternatively at least 85% homology, or alternatively at least 90% homology, or alternatively, at least 95% homology or alternatively, at least 98% homology to SEQ ID NO. 4 and/or 7, each as determined using methods known to those skilled in the art and identified herein, when run under default parameters.

Polypeptides comprising the amino acid sequences of the invention can be prepared by expressing polynucleotides encoding the polypeptide sequences of this invention in an appropriate host cell. This can be accomplished by methods of recombinant DNA technology known to those skilled in the art. Accordingly, this invention also provides methods for recombinantly producing the polypeptides of this invention in a eukaryotic or prokaryotic host cells. The proteins and polypeptides of this invention also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

It is know to those skilled in the art that modifications can be made to any peptide to provide it with altered properties. Polypeptides of the invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred.

In a further embodiment, subunits of polypeptides that confer useful chemical and structural properties will be chosen. For example, peptides comprising D-amino acids may be resistant to L-amino acid-specific proteases in vivo. Modified compounds with D-amino acids may be synthesized with the amino acids aligned in reverse order to produce the peptides of the invention as retro-inverso peptides. In addition, the present invention envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present invention provides a method to produce a constrained peptide that incorporates random sequences at all other positions.

The following non-classical amino acids may be incorporated in the peptides of the invention in order to introduce particular conformational motifs: 1,2,3,4-tetrahydroisoquinoline-3-carboxylate (Kazrnierski et al. (1991) J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby (1991) Tetrahedron Lett. 32(41):5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1989) J. Takeda Res. Labs. 43:53-76) histidine isoquinoline carboxylic acid (Zechel et al. (1991) Int. J. Pep. Protein Res. 38(2): 131-138); and HIC (histidine cyclic urea), (Dharanipragada et al. (1993) Int. J. Pep. Protein Res. 42(1):68-77) and (Dharanipragada et al. (1992) Acta. Crystallogr. C. 48:1239-1241).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); α-helix inducing analogs (Kemp et al. (1988) Tetrahedron Lett. 29:4935-4938); α-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Clones et al. (1988) Tetrahedron Lett. 29:3853-3856); tetrazole (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 56:436. Conformationally restricted mimetics of beta turns and beta bulges, and peptides containing them, are described in U.S. Pat. No. 5,440,013, issued Aug. 8, 1995 to Kahn.

It is know to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobicity, size, or charge. Methods used to determine the appropriate amino acid to be substituted and for which amino acid are know to one of skill in the art. Non-limiting examples include empirical substitution models as described by Dahoff et al. (1978) In Atlas of Protein Sequence and Structure Vol. 5 suppl. 2 (ed. M. O. Dayhoff), pp. 345-352. National Biomedical Research Foundation, Washington, D.C.; PAM matrices including Dayhoff matrices (Dahoff et al. (1978), supra, or JTT matrices as described by Jones et al. (1992) Comput. Appl. Biosci. 8:275-282 and Gonnet et al. (1992) Science 256:1443-1145; the empirical model described by Adach and Hasegawa (1996) J. Mol. Evol. 42:459-468; the block substitution matrices (BLOSUM) as described by Henikoff and Henikoff (1992) Proc. Natl. Acad. Sci. USA 89:10915-10919; Poisson models as described by Nei (1987) Molecular Evolutionary Genetics. Columbia University Press, New York.; and the Maximum Likelihood (ML) Method as described by Müller et al. (2002) Mol. Biol. Evol. 19:8-13.

Polypeptide Conjugates

The polypeptides and polypeptide complexes of the invention can be used in a variety of formulations, which may vary depending on the intended use. For example, one or more can be covalently or non-covalently linked (complexed) to various other molecules, the nature of which may vary depending on the particular purpose. For example, a peptide of the invention can be covalently or non-covalently complexed to a macromolecular carrier, including, but not limited to, natural and synthetic polymers, proteins, polysaccharides, polypeptides (amino acids), polyvinyl alcohol, polyvinyl pyrrolidone, and lipids. A peptide can be conjugated to a fatty acid, for introduction into a liposome, see U.S. Pat. No. 5,837,249. A peptide of the invention can be complexed covalently or non-covalently with a solid support, a variety of which are known in the art and described herein. An antigenic peptide epitope of the invention can be associated with an antigen-presenting matrix such as an MHC complex with or without co-stimulatory molecules.

Examples of protein carriers include, but are not limited to, superantigens, serum albumin, tetanus toxoid, ovalbumin, thyroglobulin, myoglobulin, and immunoglobulin.

Peptide-protein carrier polymers may be formed using conventional cross-linking agents such as carbodiimides. Examples of carbodiimides are 1-cyclohexyl-3-(2-morpholinyl-(4-ethyl)carbodiimide (CMC), 1-ethyl-3-(3-dimethyaminopropyl)carbodiimide (EDC) and 1-ethyl-3-(4-azonia-44-dimethylpentyl)carbodiimide.

Examples of other suitable cross-linking agents are cyanogen bromide, glutaraldehyde and succinic anhydride. In general, any of a number of homo-bifunctional agents including a homo-bifunctional aldehyde, a homo-bifunctional epoxide, a homo-bifunctional imido-ester, a homo-bifunctional N-hydroxysuccinimide ester, a homo-bifunctional maleimide, a homo-bifunctional alkyl halide, a homo-bifunctional pyridyl disulfide, a homo-bifunctional aryl halide, a homo-bifunctional hydrazide, a homo-bifunctional diazonium derivative and a homo-bifunctional photoreactive compound may be used. Also included are hetero-bifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homo-bifunctional cross-linking agents include the bifunctional N-hydroxysuccinimide esters dithiobis(succinimidylpropionate), disuccinimidyl suberate, and disuccinimidyl tartarate; the bifunctional imido-esters dimethyl adipimidate, dimethyl pimelimidate, and dimethyl suberimidate; the bifunctional sulfhydryl-reactive crosslinkers 1,4-di-[3'-(2'-pyridyldithio)propion-amido] butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether; the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetamide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl) amine, respectively.

Examples of common hetero-bifunctional cross-linking agents that may be used to effect the conjugation of proteins to peptides include, but are not limited to, SMCC (succinimidyl-4-(N-maleimidomethyl)cyclohexane-1-carboxylate), MBS (m-maleimidobenzoyl-N-hydroxysuccinimide ester), SIAB (N-succinimidyl(4-iodoacetyl)aminobenzoate), SMPB (succinimidyl-4-(p-maleimidophenyl)butyrate), GMBS (N-(γ-maleimidobutyryloxy)succinimide ester), MPBH (4-(4-N-maleimidophenyl)butyric acid hydrazide), M2C2H (4-(N-maleimidomethyl)cyclohexane-1-carboxyl-hydrazide), SMPT (succinimidyloxycarbonyl-α-methyl-α-(2-pyridyldithio)toluene), and SPDP (N-succinimidyl 3-(2-pyridyldithio)propionate).

Cross-linking may be accomplished by coupling a carbonyl group to an amine group or to a hydrazide group by reductive amination.

Peptides of the invention also may be formulated as non-covalent attachment of monomers through ionic, adsorptive, or biospecific interactions. Complexes of peptides with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of peptides may be done to surfaces such as microparticle latex beads or to other hydrophobic polymers, forming non-covalently associated peptide-superantigen complexes effectively mimicking cross-linked or chemically polymerized protein. Finally, peptides may be non-covalently linked through the use of biospecific interactions between other molecules. For instance, utilization of the strong affinity of biotin for proteins such as avidin or streptavidin or their derivatives could be used to form peptide complexes. These biotin-binding proteins contain four binding sites that can interact with biotin in solution or be covalently attached to another molecule. (See Wilchek (1988) Anal. Biochem. 171: 1-32). Peptides can be modified to possess biotin groups using common biotinylation reagents such as the N-hydroxysuccinimidyl ester of D-biotin (NHS-biotin) which reacts with available amine groups on the protein. Biotinylated peptides then can be incubated with avidin or streptavidin to create large complexes. The molecular mass of such polymers can be regulated through careful control of the molar ratio of biotinylated peptide to avidin or streptavidin.

Also provided by this application are the peptides and polypeptides described herein conjugated to a label, e.g., a fluorescent or bioluminescent label, for use in the diagnostic methods. For example, detectably labeled peptides and polypeptides can be bound to a column and used for the detection and purification of antibodies. Suitable fluorescent labels include, but are not limited to, fluorescein, rhodamine, tetramethylrhodamine, eosin, erythrosin, coumarin, methylcoumarins, pyrene, Malacite green, stilbene, Lucifer Yellow, Cascade Blue™, and Texas Red. Other suitable optical dyes are described in Haugland, Richard P. (1996) Molecular Probes Handbook.

The polypeptides of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to, Freund's Complete Adjuvant, Freund's Incomplete Adjuvant and mineral salts.

Host Cells

Also provided are host cells comprising one or more of the polypeptides of this invention. In one aspect, the polypeptides are expressed and present on the cell surface (extracellularly). Suitable cells containing the inventive polypeptides include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. The cells can be purchased from a commercial vendor such as the American Type Culture Collection (ATCC, Rockville, Md., USA) or cultured from an isolate using methods known in the art. Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia,* or *Pichia*. See e.g., U.S. Pat. Nos. 4,812,405; 4,818,700; 4,929,555; 5,736,383; 5,955,349; 5,888,768 and 6,258,559.

In addition to species specificity, the cells can be of any particular tissue type such as neuronal or alternatively a somatic or embryonic stem cell such as a stem cell that can or can not differentiate into a neuronal cell, e.g., embryonic stem cell, adipose stem cell, neuronal stem cell and hematopoieitic stem cell. The stem cell can be of human or animal origin, such as mammalian.

Isolated Polynucleotides and Compositions

This invention also provides isolated polynucleotides encoding the polypeptides described above. In one aspect the polynucleotides encode polypeptides comprising the sequences (SEQ ID NOS: 1 through 8). In another aspect, the isolated polynucleotides encode a polypeptide comprising two non-contiguous binding regions, the binding regions comprising the amino acids ASIDGFDQYFRSQTLANNR (SEQ ID NO. 3) and SSVWDERHDSHIPLEDCR (SEQ ID NO. 6). Another aspect of this invention is an isolated polynucleotide encoding a complex which comprises two non-contiguous amino acids ASIDGFDQYFR (SEQ ID NO. 4) and HDSHIPLEDCR (SEQ ID NO. 7). In yet a further aspect, the isolated polynucleotides encode polypeptides having two or more non-contiguous amino acid sequences of the group:

| AVIMFANEDDIR; | (SEQ ID NO. 2) |
| ASIDGFDQYFRSQTLANNR; | (SEQ ID NO. 3) |
| ASIDGFDQYFR; | (SEQ ID NO. 4) |
| CTENVPVTDFFVGPVCIIPK; | (SEQ ID NO. 5) |
| SSVWDERHDSHIPLEDCR; | (SEQ ID NO. 6) |
| HDSHIPLEDCR; | (SEQ ID NO. 7) | or amino acids having at least 65% sequence homology to SEQ ID NOS.: 2 through 7. Examples of polynucleotides encoding these polypeptides are provided in Table 2.

This invention also provides the complementary polynucleotides to the sequences identified above or their complements. Complementarity can be determined using traditional hybridization under conditions of moderate or high stringency. As used herein, the term polynucleotide intends DNA and RNA as well as modified nucleotides. For example, this invention also provides the anti-sense polynucleotide stand, e.g. antisense RNA to these sequences or their complements. One can obtain an antisense RNA using the sequences that encode SEQ ID NOS: 1 through 8 (e.g., provided in Seq. ID NOS. 9 through 16), and the methodology described in Van der Krol, et al. (1988) BioTechniques 6:958.

Also provided are polynucleotides encoding substantially homologous and biologically equivalent polypeptides to the inventive polypeptides and polypeptide complexes. Substantially homologous and biologically equivalent intends those having varying degrees of homology, such as at least 65%, or alternatively, at least 70%, or alternatively, at least 75%, or alternatively at least 80%, or alternatively, at least 85%, or alternatively at least 90%, or alternatively, at least 95%, or alternatively at least 97% homologous as defined above and which encode polypeptides having the biological activity to bind ADDLs as described herein. It should be understood although not always explicitly stated that embodiments to substantially homolgous polypeptides and polynucleotides are intended for each aspect of this invention, e.g., polpeptides, polynucleotides and antibodies.

The polynucleotides of this invention can be replicated using conventional recombinant techniques. Alternatively, the polynucleotides can be replicated using PCR technology. PCR is the subject matter of U.S. Pat. Nos. 4,683,195; 4,800, 159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this invention also provides a process for obtaining the polynucleotides of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable prokaryotic or eukaryotic host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook and Russell (2001) supra. For instance, mRNA can be isolated using various lytic enzymes or chemical solutions according to the procedures set forth in Sambrook and Russell (2001) supra or extracted by nucleic-acid-binding resins following the accompanying instructions provided by manufactures.

In one aspect, the RNA is short interfering RNA, also known as siRNA. Methods to prepare and screen interfering RNA and select for the ability to block polynucleotide expression are known in the art and non-limiting examples of which are shown below. These interfering RNA are provided by this invention.

siRNA sequences can be designed by obtaining the target mRNA sequence and determining an appropriate siRNA complementary sequence. siRNAs of the invention are designed to interact with a target sequence, meaning they complement a target sequence sufficiently to hybridize to that sequence. An siRNA can be 100% identical to the target sequence. However, homology of the siRNA sequence to the target sequence can be less than 100% as long as the siRNA can hybridize to the target sequence. Thus, for example, the siRNA molecule can be at least 70%, 75%, 80%, 85%, 90%, 95%, 96%, 97%, 98%, 99% or 100% identical to the target sequence or the complement of the target sequence. Therefore, siRNA molecules with insertions, deletions or single point mutations relative to a target may also be used. The generation of several different siRNA sequences per target mRNA is recommended to allow screening for the optimal target sequence. A homology search, such as a BLAST search, should be performed to ensure that the siRNA sequence does not contain homology to any known mammalian gene.

In general, its preferable that the target sequence be located at least 100-200 nucleotides from the AUG initiation codon and at least 50-100 nucleotides away from the termination codon of the target mRNA (Duxbury (2004) J. Surgical Res. 117:339-344).

Researchers have determined that certain characteristics are common in siRNA molecules that effectively silence their target gene (Duxbury (2004) J. Surgical Res. 117:339-344; Ui-Tei et al. (2004) Nucl. Acids Res. 32:936-48). As a general guide, siRNAs that include one or more of the following conditions are particularly useful in gene silencing in mammalian cells: GC ratio of between 45-55%, no runs of more than 9 G/C residues, G/C at the 5' end of the sense strand; A/U at the 5' end of the antisense strand; and at least 5 A/U residues in the first 7 bases of the 5' terminal of the antisense strand.

siRNA are, in general, from about 10 to about 30 nucleotides in length. For example, the siRNA can be 10-30 nucleotides long, 12-28 nucleotides long, 15-25 nucleotides long, 19-23 nucleotides long, or 21-23 nucleotides long. When an siRNA contains two strands of different lengths, the longer of the strands designates the length of the siRNA. In this situation, the unpaired nucleotides of the longer strand would form an overhang.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. For example, the stem can be 10-30 nucleotides long, 12-28 nucleotides long, 15-25 nucleotides long, 19-23 nucleotides long, or 21-23 nucleotides long.

Tools to assist siRNA design are readily available to the public. For example, a computer-based siRNA design tool is available by Dharmacon RNAi Technologies, last accessed on Nov. 26, 2007.

Synthesis of dsRNA and siRNA dsRNA and siRNA can be synthesized chemically or enzymatically in vitro as described in Micura (2002) Agnes Chem. Int. Ed. Emgl. 41:2265-2269; Betz (2003) Promega Notes 85:15-18; and Paddison and Hannon (2002) Cancer Cell. 2:17-23. Chemical synthesis can be performed via manual or automated methods, both of which are well known in the art as described in Micura (2002), supra. siRNA can also be endogenously expressed inside the cells in the form of shRNAs as described in Yu et al. (2002) Proc. Natl. Acad. Sci. USA 99:6047-6052; and McManus et al. (2002) RNA 8:842-850. Endogenous expression has been achieved using plasmid-based expression systems using small nuclear RNA promoters, such as RNA polymerase III U6 or H1, or RNA polymerase II U1 as described in Brummelkamp et al. (2002) Science 296:550-553 (2002); and Novarino et al. (2004) J. Neurosci. 24:5322-5330.

In vitro enzymatic dsRNA and siRNA synthesis can be performed using an RNA polymerase mediated process to produce individual sense and antisense strands that are annealed in vitro prior to delivery into the cells of choice as describe in Fire et al. (1998) Nature 391:806-811; Donze and Picard (2002) Nucl. Acids Res. 30(10):e46; Yu et al. (2002); and Shim et al. (2002) J. Biol. Chem. 277:30413-30416. Several manufacturers (Promega, Ambion, New England Biolabs, and Stragene) produce transcription kits useful in performing the in vitro synthesis.

In vitro synthesis of siRNA can be achieved, for example, by using a pair of short, duplex oligonucleotides that contain T7 RNA polymerase promoters upstream of the sense and antisense RNA sequences as the DNA template. Each oligonucleotide of the duplex is a separate template for the synthesis of one strand of the siRNA. The separate short RNA strands that are synthesized are then annealed to form siRNA as described in Protocols and Applications, Chapter 2: RNA interference, Promega Corporation, (2005).

In vitro synthesis of dsRNA can be achieved, for example, by using a T7 RNA polymerase promoter at the 5'-ends of both DNA target sequence strands. This is accomplished by using separate DNA templates, each containing the target sequence in a different orientation relative to the T7 promoter, transcribed in two separate reactions. The resulting transcripts are mixed and annealed post-transcriptionally. DNA templates used in this reaction can be created by PCR or by using two linearized plasmid templates, each containing the T7 polymerase promoter at a different end of the target sequence. Protocols and Applications, Chapter 2: RNA interference, Promega Corporation, (2005).

In order to express the proteins described herein, delivery of nucleic acid sequences encoding the gene of interest can be delivered by several techniques. Examples of which include viral technologies (e.g. retroviral vectors, adenovirus vectors, adeno-associated virus vectors, alphavirus vectors and the like) and non-viral technologies (e.g. DNA/liposome complexes, micelles and targeted viral protein-DNA complexes) as described herein. Once inside the cell of interest, expression of the transgene can be under the control of ubiquitous promoters (e.g. EF-1α) or tissue specific promoters (e.g. Calcium Calmodulin kinase 2 (CaMKI) promoter, NSE promoter and human Thy-1 promoter). Alternatively expression levels may controlled by use of an inducible promoter system (e.g. Tet on/off promoter) as described in Wiznerowicz et al. (2005) Stem Cells 77:8957-8961.

Non-limiting examples of promoters include, but are not limited to, the cytomegalovirus (CMV) promoter (Kaplitt et al. (1994) Nat. Genet. 8:148-154), CMV/human β3-globin promoter (Mandel et al. (1998) J. Neurosci. 18:4271-4284), NCX1 promoter, αMHC promoter, MLC2v promoter, GFAP promoter (Xu et al. (2001) Gene Ther., 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277) and the β-glucuronidase (GUSB) promoter (Shipley et al. (1991) Genetics 10:1009-1018), the human serum albumin promoter, the alpha-1-antitrypsin promoter. To improve expression, other regulatory elements may additionally be operably linked to the transgene, such as, e.g., the Woodchuck Hepatitis Virus Post-Regulatory Element (WPRE) (Donello et al. (1998) J. Virol. 72: 5085-5092) or the bovine growth hormone (BGH) polyadenylation site. Also provided herein is a polynucleotide probe or primer comprising at least 10, or alternatively, at least 17 or alternatively at least 20, or alternatively, at least 50, or alternatively, at least 75 polynucleotides, or alternatively at least 100 polynucleotides encoding SEQ ID NOS: 1 through 8 or their complements. Suitable probes and primers are described supra. It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. A probe useful for detecting the aforementioned mRNA is at least about 80% identical to the homologous region of comparable size contained in the previously identified sequences (identified above) which correspond to previously characterized polynucleotides of this invention. Alternatively, the probe is 85% identical to the corresponding gene sequence after alignment of the homologous region; and yet further, it exhibits 90% identity, or still further, at least 95% identical.

These probes can be used in radioassays (e.g. Southern and Northern blot analysis) to detect or monitor expression of the polynucleotides or polypeptides of this invention. The probes also can be attached to a solid support or an array such as a chip for use in high throughput screening assays for the detection of expression of the gene corresponding to one or more polynucleotide(s) of this invention.

The polynucleotides and fragments of the polynucleotides of the present invention also can serve as primers for the detection of genes or gene transcripts that are expressed in neuronal cells, for example, to confirm transduction of the polynucleotides into host cells. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. Primer length is the same as that identified for probes, above.

The invention further provides the isolated polynucleotides of this invention operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells as described above and constructed using well known methods. See Sambrook and Russell (2001), supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; DEAE-dextran; electroporation; or microinjection. See Sambrook and Russell (2001), supra for this methodology.

The present invention also provides delivery vehicles suitable for delivery of a polynucleotide of the invention into cells (whether in vivo, ex vivo, or in vitro). A polynucleotide of the invention can be contained within a gene delivery vehicle, a cloning vector or an expression vector. These vectors (especially expression vectors) can in turn be manipulated to assume any of a number of forms which may, for example, facilitate delivery to and/or entry into a cell.

These isolated host cells containing the polynucleotides of this invention are useful for the recombinant replication of the polynucleotides and for the recombinant production of peptides and for high throughput screening.

The polynucleotides of this invention can be conjugated to a detectable label or combined with a carrier such as a solid support or pharmaceutically acceptable carrier. Suitable solid supports are described above as well as have suitable labels. Methods for attaching a label to a polynucleotide are known to those skilled in the art. See Sambrook and Russell (2001), supra.

Diagnostic and Therapeutic Antibody Compositions

This invention also provides an antibody capable of specifically forming a complex with a protein or polypeptide of this invention, which are useful in the diagnostic and therapeutic methods of this invention. The term "antibody" includes polyclonal antibodies and monoclonal antibodies, antibody fragments, as well as derivatives thereof (described above). The antibodies include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify therapeutic and/or diagnostic polypeptides.

In one aspect, an antibody of the present invention binds a polypeptide comprising SEQ ID NO. 1 or an amino acid sequence having at least 80% homology, or alternatively, at least 85% homology, or alternatively, at least 90% homology, or alternatively, at least 95% homology, or alternatively at least 98% homology to SEQ ID NO. 1.

The invention also provides an antibody that binds two binding regions, the two binding regions being non-contiguous and comprising the amino acid sequences ASIDGFDQYFRSQTLANNR (SEQ ID NO. 3) and SSVWDERHDSHIPLEDCR (SEQ ID NO. 6), or an amino acid sequence at least 65% homologous, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NOS. 3 or 6.

Also provided is an antibody that binds a polypeptide comprising two non-contiguous amino acids comprising ASIDGFDQYFR (SEQ ID NO. 4 and HDSHIPLEDCR (SEQ ID NO. 7), or a polypeptide having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NOS. 4 or 7.

This invention further provides an antibody that binds a polypeptide comprising the amino acid sequence ASIDGFDQYFRSQTLANNRRNVWFAEFWEENFGCKLGSHGKRNSHIKKCTENVPV TDFFVGPVCIIPKTDTKPRSSVWDERHDSHIPLEDCR (SEQ ID NO. 8) or an amino acid sequence having at least 60% homology, or alternatively at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 8.

Also provided is antibody that binds at least one polypeptide of the group:

```
AVIMFANEDDIR;              (SEQ ID NO. 2)

ASIDGFDQYFRSQTLANNR;       (SEQ ID NO. 3)

ASIDGFDQYFR;               (SEQ ID NO. 4)

CTENVPVTDFFVGPVCIIPK;      (SEQ ID NO. 5)

SSVWDERHDSHIPLEDCR;        (SEQ ID NO. 6)

HDSHIPLEDCR;               (SEQ ID NO. 7)
or
``` amino acids having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NOS. 2 through 7, as defined herein.

In another aspect, the invention provides an antibody that does not bind soluble ADDL, but does bind at least one of the following polypeptides:

a. a polypeptide comprising amino acid sequence ARAVIMFANEDDIRRILEAAKKLNQSGHFLWIGSDSWGSKIAPVYQQEEI AEGAVTILPKRASIDGFDQYFRSQTLANNRRNVWFAEFWEENFGCKLGS HGKRNSHIKKCTENVPVTDFFVGPVCIIPKTDTKPRSSVWDERHDSHIPLE DCRF (SEQ ID NO. 1) or an amino acid sequence having at least 80% homology, or alternatively at least 85% homology, or alternatively, at least 90% homology, or alternatively, at least 95% homology, or alternatively, at least 98% homology to SEQ ID NO. 1;

b. a polypeptide comprising the amino acid sequence AVIMFANEDDIR (SEQ ID NO. 2) or an amino acid sequence having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 2;

c. a polypeptide comprising the amino acid sequence ASIDGFDQYFRSQTLANNR (SEQ ID NO. 3) or an amino acid sequence having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 3;

e. a polypeptide comprising the amino acid sequence ASIDGFDQYFR (SEQ ID NO. 4) or an amino acid sequence having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 4;

f. a polypeptide comprising the amino acid sequence CTENVPVTDFFVGPVCIIPK (SEQ ID NO. 5) or an amino acid sequence having at least 65%, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology homology to SEQ ID NO. 5;

g. a polypeptide comprising the amino acid sequence SSVWDERHDSHIPLEDCR (SEQ ID NO. 6) or an amino acid sequence having at least 65%, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 6;

h. a polypeptide comprising the amino acid sequence HDSHIPLEDCR (SEQ ID NO. 7) or an amino acid sequence having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 7;
i. a polypeptide comprising the amino acid sequence ASIDGFDQYFRSQTLANNRRNVWFAEFWEENFGCKLGSHGKRNSHIKK CTENVPVTDFFVGPVCIIPKTDTKPRSSVWDERHDSHIPLEDCR (SEQ ID NO. 8) or an amino acid sequence having at least 60% homology, or alternatively, at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NO. 8;
j. a polypeptide comprising two non-contiguous binding regions, the binding regions comprising ASIDGFDQYFRSQTLANNR (SEQ ID NO. 3) and SSVWDERHDSHIPLEDCR (SEQ ID NO. 6) or an amino acid sequence having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NOS. 3 or 6;
k. a polypeptide comprising two non-contiguous binding regions, the binding regions comprising ASIDGFDQYFR (SEQ ID NO. 4) and HDSHIPLEDCR (SEQ ID NO. 7) or an amino acid sequence having at least 65% homology, or alternatively, at least 70% homology, or alternatively, at least 75% homology, or alteratively, at least 80% homology, or alternatively at least 85% homology, or alternatively, at least 90% homology, or alternatively, at least 95% homology, or alternatively, at least 98% homology to SEQ ID NOS. 4 or 7;
l. a polypeptide comprising amino acid sequence ARAVIMFANEDDIRRILEAAKKLNQSGHFLWIGSDSWGSKIAPVYQQEEI AEGAVTILPKRASIDGFDQYFRSQTLANNRRNVWFAEFWEENFGCKLGS HGKRNSHIKKCTENVPVTDFFVGPVCIIPKTDTKPRSSVWDERHDSHIPLE DCRF (SEQ ID NO. 1);
m. a polypeptide comprising the amino acid sequence AVIMFANEDDIR (SEQ ID NO. 2);
n. a polypeptide comprising the amino acid sequence ASIDGFDQYFRSQTLANNR (SEQ ID NO. 3);
o. a polypeptide comprising the amino acid sequence ASIDGFDQYFR (SEQ ID NO. 4);
p. a polypeptide comprising the amino acid sequence CTENVPVTDFFVGPVCIIPK (SEQ ID NO. 5);
q. a polypeptide comprising the amino acid sequence SSVWDERHDSHIPLEDCR (SEQ ID NO. 6);
r. a polypeptide comprising the amino acid sequence HDSHIPLEDCR (SEQ ID NO. 7);
s. a polypeptide comprising the amino acid sequence ASIDGFDQYFRSQTLANNRRNVWFAEFWEENFGCKLGSHGKRNSHIKK CTENVPVTDFFVGPVCIIPKTDTKPRSSVWDERHDSHIPLEDCR (SEQ ID NO. 8);
t. a polypeptide comprising two non-contiguous binding regions, the binding regions comprising ASIDGFDQYFRSQTLANNR (SEQ ID NO. 3) and SSVWDERHDSHIPLEDCR (SEQ ID NO. 6); or
u. a polypeptide comprising two non-contiguous binding regions, the binding regions comprising ASIDGFDQYFR (SEQ ID NO. 4) and HDSHIPLEDCR (SEQ ID NO. 7).

This invention also provides an antibody-peptide complex comprising antibodies described above and a polypeptide that specifically binds to the antibody. In one aspect the polypeptide is the polypeptide against which the antibody was raised. In one aspect the antibody-peptide complex is an isolated complex. In a further aspect, the antibody of the complex is, but not limited to, a polyclonal antibody, a monoclonal antibody, a humanized antibody or an antibody derivative described herein. Either or both of the antibody or peptide of the antibody-peptide complex can be detectably labeled. In one aspect, the antibody-peptide complex of the invention can be used as a control or reference sample in diagnostic or screening assays.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., American Type Culture Collection (ATTC) and Life Technologies., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490 and is herein incorporated by reference in its entirety.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits. (1998) Advanced Drug Delivery Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4): 247-260; Jakobovits (1993) Nature 362(6417):255-258; Jakobovits et al. (1993) Proc. Natl. Acad. Sci. USA 90(6): 2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create vereered antibodies. Vereered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate vereered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al., (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. USA 82:8653 or Spira, et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn, et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

This invention also provides antibodies that not only bind to a polypeptide or complex as identified herein but are further characterized by blocking ADDL binding to neuronal cells or cells expressing target receptors; inhibition of ADDL binding or ADDL binding competent mimetic structures measured in the presence of identified agonists/antagonist; inhibition of the endogenous ligand glutamate or small molecules which may act as co-agonist to confer structural changes which promote ADDL binding/inhibition; the properties of antibodies that block ADDL binding to receptors, which are not restricted to the primary sequence information, i.e. linear binding epitopes; and identification of ADDL binding epitopes to mGluR class receptor, which will provide the basis for rational design of neighboring sequences and subsequent antibody generation.

In some aspects of this invention, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Nonhuman Transgenic Animals

In yet another aspect, the present invention provides a transgenic non-human animal, such as a transgenic mouse (also referred to herein as a "HuMAb mouse"), which expresses a fully human monoclonal antibody that neutralizes at least one protein subtype similar to an antibody of this invention as defined above. In a particular embodiment, the transgenic nonhuman animal is a transgenic mouse having a genome comprising a human heavy chain transgene and a human light chain transgene encoding all or a portion of an antibody of the invention. To generate human antibodies, the transgenic non-human animal can be immunized with a purified or enriched preparation of the peptide compositions of the present invention. Preferably, the transgenic nonhuman animal, e.g., the transgenic mouse, is capable of producing multiple isotypes of human monoclonal antibodies to the polypeptides or polypeptide complexes described above (e.g., IgG, IgA and/or IgM) by undergoing V-D-J recombination and isotype switching. Isotype switching may occur by, e.g., classical or non-classical isotype switching.

Accordingly, in another embodiment, the invention provides isolated cells derived or isolated from a transgenic nonhuman animal as described above, e.g., a transgenic mouse, which express human antibodies. The isolated B-cells can then be immortalized by fusion to an immortalized cell to provide a source (e.g., a hybridoma) of human antibodies. These hybridomas are also included within the scope of the invention.

The present invention is also directed to a transgenic non-human animal whose genome comprises a homozygous genotype encoding one or more polypeptides comprising amino acid sequences of SEQ ID NOS. 1-8 or a biologically equivalent polypeptides as described herein. In another embodiment, the present invention is directed to a transgenic non-human animal whose germ cells and somatic cells contain a recombinant polynucleotide sequence that encodes one or more polypeptides comprising amino acid SEQ ID NOS. 1-8 or a biologically equivalent polypeptides as described herein, wherein the transgene sequence is introduced into said non-human animal, or an ancestor of said non-human animal, at an embryonic stage, where the transgene encodes a polypeptide described herein.

In another aspect, the present invention provides a method of making a knock-in non-human animal cell comprising the steps of (1) effecting homologous recombination between an endogenous gene and a transgene, wherein said transgene comprises (a) a sequence encoding at least one amino acid sequence of SEQ ID NOS. 1-8 or a biologically equivalent polypeptide as described herein, (b) a selectable marker flanked by a pair of repeat sites, and (c) a pair of sequences homologous to the endogenous gene flanking both the transgene and the selectable marker; and, (2) effecting further recombination to remove the selectable marker, wherein the transgene encodes at least one amino acid sequence of SEQ ID NOS. 1-8.

The present invention is also directed to a knockout-transgenic non-human animal whose genome comprises a deletion of the entire or a functional portion of an endogenous gene which encodes one or more polypeptides comprising amino acid sequences of SEQ ID NOS. 1-8. In another aspect, the genome comprises a deletion of the entire or a functional portion of an endogenous gene which encodes a polypeptide comprising at least 60% homology to SEQ ID NO. 8. In yet another aspect, the genome comprises a deletion of the entire or a functional portion of an endogenous gene which encodes a polypeptide comprising two non-contiguous binding regions, the binding regions have at least 65% homology to SEQ ID NOS. 3 and 6 or alternatively SEQ ID NOS. 4 and 7. Methods for generating a knockout-transgenic non-human animal is described in U.S. Pat. Nos. 7,247,767; 6,984,773; 6,245,963; and 5,777,195.

Compositions for Diagnosis and Therapy

One or more of the above compositions can be further combined with a carrier, a pharmaceutically acceptable carrier or medical device which is suitable for use of the compositions in diagnostic or therapeutic methods.

The carrier can be a liquid phase carrier or a solid phase carrier, e.g., bead, gel, microarray, or carrier molecule such as a liposome. The composition can optionally further comprise at least one further compound, protein or composition.

Additional examples of "carriers" includes therapeutically active agents such as another peptide or protein (e.g., an Fab' fragment). For example, an antibody of this invention, derivative or fragment thereof can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, this invention encompasses a large variety of antibody conjugates, bi- and multispecific molecules, and fusion proteins, whether or not they target the same epitope as the antibodies of this invention.

Yet additional examples of carriers are organic molecules (also termed modifying agents) or activating agents, that can be covalently attached, directly or indirectly, to an antibody of this invention. Attachment of the molecule can improve pharmacokinetic properties (e.g., increased in vivo serum half-life). Examples of organic molecules include, but are not limited to a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane.

Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. A suitable hydrophilic polymer that modifies the antibody of the invention has a molecular weight of about 800 to about 150,000 Daltons as a separate molecular entity. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Examples of such include, but are not limited to n-dodecanoate, n-tetradecanoate, n-octadecanoate, n-eicosanoate, n-docosanoate, n-triacontanoate, n-tetracontanoate, cis-Δ9-octadecanoate, all cis-Δ5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The present invention further provides at least one antibody method or composition, for detecting or monitoring receptor expression in a cell, tissue, organ, animal or patient. They are also used to prognose or monitor disease progression.

Also provided is a composition containing at least one antibody of this invention, derivative or fragment thereof, suitable for administration in an effective amount to modulate a neurodegenerative disorder correlative to the expression of the receptor or receptor complex. The compositions include, for example, pharmaceutical and diagnostic compositions/kits, comprising a pharmaceutically acceptable carrier and at least one antibody of this invention, variant, derivative or fragment thereof. As noted above, the composition can further comprise additional antibodies or therapeutic agents which in combination, provide multiple therapies tailored to provide the maximum therapeutic benefit.

Alternatively, a composition of this invention can be co-administered with other therapeutic agents, whether or not linked to them or administered in the same dosing. They can be coadministered simultaneously with such agents (e.g., in a single composition or separately) or can be administered before or after administration of such agents. Such agents can include Aricept® (donepezil), Razadyne® (galantamine), Nanenda® (mementine), Exalon® (rivastigmine), Cognex® (tacrine), or other agents known to those skilled in the art. The compositions can be combined with alternative therapies such as administration of tranquilizers, mood stabilizing medications, behavior treatments (including treatments for aggressive behavior, incontinence, sleep difficulties, and wandering behavior), and individual activities and therapies (e.g., Reminiscence therapy) known to those skilled in the art.

Diagnostic Methods Utilizing Recombinant DNA Technology and Bioinformatics

In diagnosing disease characterized by expression of or differential expression of a gene, one typically conducts a comparative analysis of the subject's sample and appropriate controls. Preferably, a diagnostic test includes a control sample derived from a subject (hereinafter "positive control"), that exhibits the expression or expression level of the gene or polynucleotide of interest. It is also useful to include a "negative control" that lacks the clinical characteristics of the pathological state and whose expression level of the gene is within a normal range. A positive correlation between the subject and the positive control with respect to the identified alterations indicates a positive response or indication. A lack of correlation between the subject and the negative control confirms the diagnosis. Applying these general concepts and the discovery and characterization of the novel receptor and/or complex as described above, in one aspect, the invention provides compositions and methods for diagnosing or monitoring the expression of the receptor and/or receptor complex by detecting or determining the expression level of the gene encoding this receptor or components of the receptor. Various methods are known for quantifying the expression of a gene of interest and include but are not limited to hybridization assays (Northern blot analysis), PCR based hybridization assays.

In assaying for an alteration in mRNA level, the nucleic acid contained in a sample is first extracted according to a standard method in the art. For instance, mRNA can be isolated using various lytic enzymes or chemical solutions according to the procedures set forth in Sambrook and Russell (2001), supra or extracted by nucleic-acid-binding resins following the accompanying instructions provided by the manufacturers. As an example, the mRNA contained in the extracted nucleic acid sample is then detected by hybridization (e.g., Northern blot analysis) and/or amplification procedures using nucleic acid probes and/or primers, respectively, according to standard procedures.

One can also utilize detect and quantify mRNA level or its expression using quantitative PCR or high throughput analysis such as Serial Analysis of Gene Expression (SAGE) as described in Velculescu, V. et al. (1995) Science 270:484-487. Briefly, the method comprises isolating multiple mRNAs from cell or tissue samples suspected of containing the transcript. Optionally, the gene transcripts can be converted to cDNA. A sampling of the gene transcripts are subjected to sequence-specific analysis and quantified. These gene transcript sequence abundances are compared against reference database sequence abundances including normal data sets for diseased and healthy patients. The patient has the disease(s) with which the patient's data set most closely correlates and for this application, includes the differential of the transcript.

After amplification, the resulting DNA fragments can be detected by agarose gel electrophoresis followed by visualization with ethidium bromide staining and ultraviolet illumination. A specific amplification of an expressed genes of interest can be verified by demonstrating that the amplified DNA fragment has the predicted size, exhibits the predicated restriction digestion pattern, and/or hybridizes to the correct cloned DNA sequence.

Polynucleotides also can be attached to a solid support for use in high throughput screening assays using methods known in the art. For example, the polynucleotide of SEQ ID NO. 8 can be used as a probe to identify receptor expression in a subject sample. International PCT Application No. WO 97/10365 and U.S. Pat. Nos. 5,405,783; 5,412,087 and 5,445,934, for example, disclose the construction of high density oligonucleotide chips which can contain one or more sequences. The chips can be synthesized on a derivatized glass surface using the methods disclosed in U.S. Pat. Nos. 5,405,783; 5,412,087 and 5,445,934. Photoprotected nucleoside phosphoramidites can be coupled to the glass surface, selectively deprotected by photolysis through a photolithographic mask, and reacted with a second protected nucleoside phosphoramidite. The coupling/deprotection process is repeated until the desired probe is complete.

Chemical synthesis of the nucleotides of the present invention can by done using techniques known to one of skill in the art. Chemical synthesis of oligonucleotides can be accomplished using a number of protocols, including the use of solid support chemistry, where an oligonucleotide is synthesized one nucleoside at a time while anchored to an inorganic polymer. The first nucleotide is attached to an inorganic polymer using a reactive group on the polymer which reacts with a reactive group on the nucleoside to form a covalent linkage. Each subsequent nucleoside is then added to the first nucleoside molecule by: 1) formation of a phosphite linkage between the original nucleoside and a new nucleoside with a protecting group; 2) conversion of the phosphite linkage to a phosphate linkage by oxidation; and 3) removal of one of the protecting groups to form a new reactive site for the next nucleoside as described in U.S. Pat. Nos. 4,458,066; 5,153,319; 5,132,418; 4,973,679 all of which are incorporated by reference herein. Solid phase synthesis of oligonucleotides eliminates the need to isolate and purify the intermediate products after the addition of every nucleotide base. Following the synthesis of RNA, the oligonucleotides is deprotected (U.S. Pat. No. 5,831,071) and purified to remove by-products, incomplete synthesis products, and the like.

U.S. Pat. No. 5,686,599, describes a method for one pot deprotection of RNA under conditions suitable for the removal of the protecting group from the 2' hydroxyl position. U.S. Pat. No. 5,804,683, describes a method for the removal of exocyclic protecting groups using alkylamines. U.S. Pat. No. 5,831,071, describes a method for the deprotection of RNA using ethylamine, propylamine, or butylamine. U.S. Pat. No. 5,281,701, describes methods and reagents for the synthesis of RNA using 5'-O-protected-2'-O-alkylsilyl-adenosine phosphoramidite and 5'-O-protected-2'-O-alkylsilylguanosine phosphoramidite monomers which are deprotected using ethylthiotetrazole. Usman and Cedergren (1992) Trends in Biochem. Sci. 17:334-339 describe the synthesis of RNA-DNA chimeras for use in studies of the role of 2' hydroxyl groups. Sproat et al. (1995) Nucleosides & Nucleotides 14:255-273, describe the use of 5-ethylthio-1H-tetrazole as an activator to enhance the quality of oligonucleotide synthesis and product yield. Gait et al. (1991) Oligonucleotides and Analogues, ed. F. Eckstein, Oxford University Press 25-48, describe general methods for the synthesis of RNA. U.S. Pat. Nos. 4,923,901; 5,723,599; 5,674,856; 5,141,813; 5,419,966; 4,458,066; 5,252,723; Weetall et al. (1974) Methods in Enzymology 34:59-72; Van Aerschot et al. (1988) Nucleosides and Nucleotides 7:75-90; Maskos and Southern (1992) Nucleic Acids Research 20: 1679-1684; Van Ness et al. (1991) Nucleic Acids Research 19:3345-3350; Katzhendler et al. (1989) Tetrahedron 45:2777-2792; Hovinen et al. (1994) Tetrahedron 50:7203-7218; GB 2,169,605; EP 325,970; PCT publication No. WO 94/01446; German Patent No. 280,968; and BaGerman Patent No. 4,306,839, all describe specific examples of solid supports for oligonucleotide synthesis and specific methods of use for certain oligonucleotides. Additionally, methods and reagents for oligonucleotide synthesis as know to one of skill in the areas describe by U.S. Pat. No. 7,205,399, here incorporated by reference in its entirety.

The expression level of the gene is determined through exposure of a sample suspected of containing the polynucleotide to the probe-modified chip. Extracted nucleic acid is labeled, for example, with a detectable label, preferably during an amplification step. Hybridization of the labeled sample is performed at an appropriate stringency level. The degree of probe-nucleic acid hybridization is quantitatively measured using a detection device, such as a confocal microscope. See, U.S. Pat. Nos. 5,578,832 and 5,631,734. The obtained measurement is directly correlated with gene expression level.

The probes and high density oligonucleotide probe arrays also provide an effective means of monitoring expression of a multiplicity of genes, one of which includes the gene. Thus, the expression monitoring methods can be used in a wide variety of circumstances including detection of disease, identification of differential gene expression between samples isolated from the same patient over a time course, or screening for compositions that upregulate or downregulate the expression of the gene at one time, or alternatively, over a period of time.

Detectable labels suitable for use in the present invention include those identified above as well as any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$) enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are known to those of skill in the art. Thus, for example, radiolabels may be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Patent Publication WO 97/10365 describes methods for adding the label to the target (sample) nucleic acid(s) prior to or alternatively, after the hybridization. These are detectable labels that are directly attached to or incorporated into the target (sample) nucleic acid prior to hybridization. In contrast, "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids, see Laboratory Techniques In Biochemistry And Molecular Biology, Vol. 24: Hybridization with Nucleic Acid Probes, P. Tijssen, ed. Elsevier, N.Y. (1993).

The nucleic acid sample also may be modified prior to hybridization to the high density probe array in order to reduce sample complexity thereby decreasing background signal and improving sensitivity of the measurement using the methods disclosed in International PCT Application No. WO 97/10365.

Results from the chip assay are typically analyzed using a computer software program. See, for example, EP 0717 113 A2 and WO 95/20681. The hybridization data is read into the program, which calculates the expression level of the targeted gene(s). This figure is compared against existing data sets of gene expression levels for diseased and healthy individuals. A correlation between the obtained data and that of a set of diseased individuals indicates the onset of a disease in the subject patient.

Diagnostic Methods for Detecting and Quantifying Protein or Polypeptides

This invention also provided methods for detecting novel receptor and receptor/or complex expression by detecting receptor and/or complex expression. A variety of techniques are available in the art for protein analysis and include, but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays and PAGE-SDS each of which can be applied in the contexts described in more detail herein. As is apparent to those skilled in the art, a positive and a negative control can by assayed concurrently to verify the integrity of the results.

Applying these general concepts and the discovery and characterization of the novel receptor and/or complex as described above, in one aspect, the invention provides a method to detect receptor and/or complex expression by contacting an agent that binds the receptor or alternatively, the receptor complex with a sample suspected of containing the receptor and/or complex under conditions that favor binding of the agent to the receptor and/or complex and detecting agent receptor complex so formed. In the context of this method, the term "agent" intends a an antibody, an antibody derivative, an antibody fragment or a polypeptide, examples of which have been identified above. Examples of samples that may contain cells expressing the receptor or receptor complex include but are not limited to tissue or fluid comprising neuronal cells. The samples can be isolated from a patient or animal that is suffering from a neurodegenerative disorder that has been correlated to receptor or complex expression, e.g., Alzheimer's disease, Down's Syndrome, mild cognitive impairment, stroke, focal ischemia associated dementia, and neuronal degeneration.

Yet further provided is a method for monitoring receptor and/or complex expression in a subject by contacting a diagnostic agent that binds the receptor or complex in vivo with the two or more samples isolated from the subject at two or more time points, each contacting conducted under conditions that favor binding of the agent to the receptor in vivo and detecting and comparing agent-receptor or agent-complex binding occurring in vivo at the two or more time periods. In the context of this method, the term "agent" intends an antibody, an antibody derivative, an antibody fragment or a polypeptide. In the context of this method, a subject intends a patient or animal that is suffering from a neurodegenerative disorder that has been correlated to receptor or complex expression, e.g., Alzheimer's disease, Down's Syndrome, mild cognitive impairment, stroke, focal ischemia associated dementia, and neuronal degeneration.

This invention also provides a method for detecting receptor and/or receptor complex expression in a subject by administering to the subject an agent that binds the receptor and/or receptor complex in vivo and under conditions that favor binding of the agent to the receptor and/or complex in vivo, and detecting any agent binding in vivo. In the context of this method, the term "agent" intends an antibody, an antibody fragment or a polypeptide, examples of which have been identified above. In the context of this method, a subject intends a patient or animal that is suffering from a neurodegenerative disorder that has been correlated to receptor or complex expression, e.g., Alzheimer's disease, Down's Syndrome, mild cognitive impairment, stroke, focal ischemia associated dementia, and neuronal degeneration.

Further provided by this invention is a method for diagnosing predisposition to a neurodegenerative disorder in a subject by contacting an agent that binds the receptor or receptor complex with a suitable sample isolated from the subject under conditions that favor binding of the agent to the receptor and/or complex and any agent binding, the presence of binding indicating predisposition to a neurodegenerative disorder. In one aspect, the neurodegenerative disorder has been linked to expression of the complex. In another aspect, the neurodegenerative disorder has been linked to ADDL formation in the subject. In the context of this method, the term "agent" intends an antibody, an antibody fragment or a polypeptide, examples of which have been identified above. In the context of this method, a subject intends a patient or animal that is suffering from a neurodegenerative disorder that has been correlated to receptor or complex expression, e.g., Alzheimer's disease, Down's Syndrome, mild cognitive impairment, stroke, focal ischemia associated dementia, and neuronal degeneration. Suitable samples for use of the method are those suspected of containing tissue or cells that express the receptor such as neuronal cells or tissues. This method can also be practiced in vivo, by administering to the subject the agent that binds the receptor and/or complex in vivo and under conditions that favor binding of the agent to the receptor or complex in vivo, and detecting bound agent if it is present.

A method for monitoring disease progression in a subject suffering from a neurodegenerative disorder is further provided by this invention. The method requires contacting a diagnostic agent that binds the receptor and/or receptor complex with two or more samples isolated from the subject at two or more time points, each contacting conducted under conditions that favor binding of the agent to the receptor and/or complex and detecting and comparing agent binding, if present, at the two or more time periods. In the context of this method, the term "agent" intends a an antibody, an antibody fragment or a polypeptide, examples of which have been identified above. In the context of this method, a subject intends a patient or animal that is suffering from a neurodegenerative disorder that has been correlated to receptor or complex expression, e.g., Alzheimer's disease, Down's Syndrome, mild cognitive impairment, stroke, focal ischemia associated dementia, and neuronal degeneration. In another aspect, the neurodegenerative disorder has been linked to ADDL formation in the subject. Suitable samples for use of the method are those suspected of containing tissue or cells that express the receptor such as neuronal cells or tissues. This method can also be practiced in vivo, by administering to the subject the agent that binds the receptor and/or complex in vivo and under conditions that favor binding of the agent to the receptor or complex in vivo, and detecting bound agent if it is present.

A method to identify a patient that is responsive to anti-receptor therapy also is provided by identifying receptor or complex expression using a method described above. If the patient is positive for receptor or complex expression, that patient is more likely to be responsive to the administration of an agent that inhibits receptor activation or ligand binding to the receptor. An effective amount of the agent can then be administered to the subject.

One can also modify known immunoassays to detect and quantify expression of the receptor or the complex. Determination of the gene product requires measuring the amount of immunospecific binding that occurs between an antibody reactive to the gene product. To detect and quantify the immunospecific binding, or signals generated during hybridization or amplification procedures, digital image analysis systems including but not limited to those that detect radioactivity of the probes or chemiluminescence can be employed.

Methods to Identify Therapeutic Agents

The present invention also provides methods to identify leads and methods for neurodegenerative disorders or selectively inhibiting activation of the receptor or receptor complex. In one aspect, the screen identifies lead compounds or biologics agents which are useful to treat neurodegenerative disorders or to treat or ameliorate the symptoms associated with neurodegenerative disorders. In one aspect the neurodegenerative disorder has been correlated to receptor or complex expression, e.g., Alzheimer's disease, Down's Syndrome, mild cognitive impairment, stroke, focal ischemia associated dementia, and neuronal degeneration. In another aspect, the neurodegenerative disorder has been linked to ADDL formation in the subject. The screens can be practiced in vitro or in vivo.

Test substances for screening can come from any source. They can be libraries of natural products, combinatorial chemical libraries, biological products made by recombinant libraries, etc. The source of the test substances is not critical to the invention. The present invention provides means for screening compounds and compositions which may previously have been overlooked in other screening schemes.

To practice the screen or assay in vitro, suitable cell cultures or tissue cultures are first provided. The cell can be a cultured cell or a genetically modified cell which differentially expresses the receptor and/or receptor complex. Alternatively, the cells can be from a tissue culture as described below. The cells are cultured under conditions (temperature, growth or culture medium and gas ($CO_2$)) and for an appropriate amount of time to attain exponential proliferation without density dependent constraints. It also is desirable to maintain an additional separate cell culture; one which does not receive the agent being tested as a control.

As is apparent to one of skill in the art, suitable cells may be cultured in microtiter plates and several agents may be assayed at the same time by noting genotypic changes, phenotypic changes and/or cell death.

When the agent is a composition other than a DNA or RNA nucleic acid molecule, the suitable conditions may be by directly added to the cell culture or added to culture medium for addition. As is apparent to those skilled in the art, an "effective" amount must be added which can be empirically determined.

The screen involves contacting the agent with a test cell expressing the receptor or complex and then assaying the cell for binding of the agent to the receptor or receptor complex. In yet another aspect, the test cell or tissue sample is isolated from the subject to be treated and one or more potential agents are screened to determine the optimal therapeutic and/or course of treatment for that individual patient. For a neuronal cell or tissue is suitable for this assay.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies. They can be administered concurrently or sequentially.

Use of the screen in an animal such as a rat or mouse, the method provides a convenient animal model system which can be used prior to clinical testing of the therapeutic agent or alternatively, for lead optimization. In this system, a candidate agent is a potential drug, and may therefore be suitable for further development, if the agent binds the receptor or receptor complex each as compared to untreated, animal expressing the receptor and/or complex. It also can be useful to have a separate negative control group of cells or animals which are healthy and not treated, which provides a further basis for comparison.

Therapeutic Antibody Compositions and Methods of Use

Certain antibodies of this invention are useful therapeutically to treat or ameliorate the symptoms of neurodegenerative disorders. The antibodies are prepared as identified above but are further screened for their ability to block ADDL binding to the receptor and/or receptor complex identified by Applicants. Thus, this invention also provides a method to treat such a neurodegenerative disorder by administering to a subject in need thereof an effective amount of the therapeutic antibody, antibody derivative, fragment, thereof and as described herein. Administration can be by any suitable method and effective amounts can be empirically determined by a treating physician. The antibodies can be delivered alone or in combination with another active agent.

In one aspect, the therapeutic and diagnostic agents are used in combination with other agents. Co-administration of these antibodies with other agents or therapies can provide unexpected synergistic therapeutic benefit. In the co-administration methods, the antibodies are also useful in reducing deleterious side-effects of known therapies and therapeutic agents, as well as yet to be discovered therapies and therapeutic agents, by decreasing dosage. In one aspect, the use of operative combinations is contemplated to provide therapeutic combinations requiring a lower total dosage of each component than may be required when each individual therapeutic method, antibody or drug is used alone, thereby reducing adverse effects. Thus, the present invention also includes methods involving co-administration of the therapeutic antibodies described herein with one or more additional active agents or methods. Indeed, it is a further aspect of this invention to provide methods for enhancing other therapies and/or pharmaceutical compositions by co-administering an antibody of this invention. In co-administration procedures, the agents may be administered concurrently or sequentially. In one embodiment, the antibodies described herein are administered prior to the other active agent(s), therapy or therapies. The pharmaceutical formulations and modes of administration may be any of those described herein or known to those of skill in the art.

In therapeutic applications, a pharmaceutical composition containing one or more polynucleotide, polypeptide, antibody, antibody fragment or derivative thereof, or composition described herein is administered to a patient suspected of, or already suffering from such a disease associated with the accumulation of ADDLs, wherein said composition is administered in an amount sufficient to cure, or at least partially arrest, the symptoms of the disease (biochemical, histological and/or behavioral), including its complication and intermediate pathological phenotypes in development of the disease. In prophylactic applications, a pharmaceutical composition containing one or more polynucleotide, polypeptide, antibody or composition described herein is administered to a patient susceptible to, or otherwise at risk of, a disease associated with the accumulation of ADDLs, wherein said compounds are administered in an amount sufficient to eliminate or reduce the risk, lessen the severity, or delay the outset of the disease. This monitoring of "disease progression" includes biochemical, histological and/or behavioral symptoms of the disease, its complications and intermediate pathological phenotypes presenting during development of the disease.

In some methods, administration of a polynucleotide, polypeptide, antibody or composition described herein reduces or eliminates mild cognitive impairment in patients that have not yet developed characteristic Alzheimer's pathology. In particular embodiments, a therapeutically effective amount intends to indicate the amount of one or more polynucleotide, polypeptide, antibody or composition described herein administered or delivered to the patient which is most likely to result in the desired response to treatment.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the polypeptide, polynucleotide, antibody, antibody fragment or derivative thereof, or compositions of this invention to decrease ADDL binding to the receptor either in vitro or in vivo by at least 10%, 25%, 40%, 60%, 80%, 90% or 95% as compared to control. Determination of these parameters is well within the skill of the art. These considerations, as well as effective formulations and administration procedures are well known in the art and are described in standard textbooks.

The "therapeutically effective amount" will vary depending on the polypeptide, polynucleotide, or compositions, the disease and its severity and the age, weight, etc., of the patient to be treated all of which is within the skill of the attending clinician. It is contemplated that a therapeutically effective amount of one or more of a polynucleotide, polypeptide, antibody or composition described herein will alter ADDL binding to the receptor in the patient as compared to binding of ADDLs in the absence of treatment. As such, impairment of long term potentiation and subsequent memory formation is decreased. A therapeutically effective amount is distinguishable from an amount having a biological effect (a "biologically effective amount"). A polypeptide, polynucleotide, or compositions of the present invention may have one or more biological effects in vitro or even in vivo, such as reducing ADDL binding to the receptor. A biological effect, however, may not result in any clinically measurable therapeutically effect as described above as determined by methods within the skill of the attending clinician.

The following examples are intended to illustrate, and not limit, the inventions disclosed herein.

EXPERIMENTAL EXAMPLES

In these examples and elsewhere, abbreviations have the following meanings:
μL or μl=Microliter
nL or nl=Nanoliter
DMSO=Dimethylsulfoxide
g=Gram
h=Hour
Hz=Hertz
M=Molar
mg=Milligram
min=Minute
mL=Milliliter
mM=Millimolar
mm=Millimeter
mmol=Millimolar
mol=Moles
MS=Mass Spectroscopy
N=Normal
cm=Centimeter
nm=Nanometer
μM=Micromolar
PBS=Phosphate Buffered Saline PBST=Phosphate Buffered Saline with Tween 20
SDS=Sodium Dodecyl Sulfate
CHAPS=3[(3-Cholamidopropyl)dimethylammonio]-propanesulfonic acid
DTT=Dithiothreitol
HFIP=Hexafluoroisopropanol
PVDF=Polyvinylidene Fluoride
HAT=Hypoxanthine and Thymine
TMB=3,3',5,5'-tetramethylbenzidine Example 1

Immunoprecipitation of ADDL Receptor Complex

Aβ soluble oligomers were assembled from peptides (SEQ ID NO. 25).
Biotin—$A\beta_{1-42}$ (SEQ ID NO. 25):
Biotin—DAEFRHDSGYEVHHQKLVFFAEDVGSNK-GAIIGLMVGGVVIA

TABLE 3

Amino Acid Sequence Used for Immunopercipitation

| SEQ ID NO. | Sequence |
|---|---|
| 25 | DAEFRHDSGYEVHHQKLVFFAEDVGSNKGAIIGLMVGGVVIA |

HFIP-treated and dried $A\beta_{1-42}$ peptides were dissolved in anhydrous DMSO at 10 mM final concentration. 1×PBS (pH 7.4) containing 100 μm $CuCl_2$ and 0.04% SDS was added to adjust the final peptide concentration to 100 μM.

Peptide monomer was allowed to assemble for 40 min at 37° C. ($A\beta_{1-42}$ into ADDLs). The solution was centrifuged at 13 k rpm for 5 min and the supernatant was transferred to a fresh reagent vial. Protein concentration post assembly was determined to be 64 μM or 0.3 mg/ml (measured by Coomassie or BCA kit, respectively).

Rat synaptosomal membranes from hippocampus were freshly prepared according to Peng et al. (2004) J. Bio. Chem. 279(20):21003-21011. Purified hippocampal membranes were pre-cleared with streptavidin beads (Pierce) to avoid unspecific binding during immunoprecipitation. 50 μl of bead slurry (50% in PBS) was added per 200 μg of hippocampal membrane and incubated for 30 min at room temperature on a shaker. After brief centrifugation, the cleared supernatant was collected in a separate vial.

100 μl of assembled oligomer (ADDLs) samples: ADDL or vehicle controls were mixed with 200 μg of pre-cleared synaptosomal membranes and allowed to bind for 30 min at room temperature. Subsequently, 50 μl of streptavidin bead slurry was added to each sample and allowed to bind for 30 min at room temperature. After incubation with beads the samples were spun for 1 min at 13,000 rpm and supernatants were discarded. Bead pellets were washed 3× with 700 μl of PBS, pH 7.4 and lastly in distilled water. Washed pellets were snap frozen on dry ice for 2-Dimensional Differential In-Gel Electrophoresis (2-D DIGE) analysis as describe in Example 2.

Example 2

Sequence Analysis and Protein Identity

Samples isolated from Example 1 were analyzed by 2-Dimensional Differential In-Gel Electrophoresis (2-D DIGE) coupled with Mass Spectrometry. This technology offers a powerful and rapid tool for analyzing global protein differential expression in cells and tissues. Protein extracts were first labeled with different fluorescence dyes, and then co-migrated on the same 2-D protein gel. Protein differential expression profiles were visualized and quantified by fluorescence readout using available software, and protein spots of interests were identified by mass spectrometry.

Mass spectrometry (MS)-based proteomics involves the enzymatic degradation of proteins to peptides by trypsin, Aebersold and Mann (2003) Nature 422:198-207. This protease has high cleavage specificity and is stable under a wide variety of conditions. Most importantly, cleaving C-terminal to arginine or lysine residues leads to peptides in the preferred mass range for effective fragmentation by tandem mass spectrometry (MS/MS) and places the highly basic residues at the C termini of the peptides. This generally leads to informative high mass y-ion series and makes tandem mass spectra more easily interpretable, Olsen et al. (2004) Molecular and Cellular Proteomics 3(6):608-614.

Sample Preparation and CyDye Labeling

Proteins bound to the beads were eluted by incubating in 100 μl lysis buffer (7M Urea, 2M Thiourea, 4% CHAPS, 30 mM TrisHCl, pH8.8) for 1 hr with agitation. The elution was repeated and the two eluates were combined. The eluted proteins were labeled with 400 pmoles of CyDye (GE Healthcare) for 40 min at 4° C. The labeling was stopped by adding 0.9 μl of 10 mM L-Lysine and incubating for 15 min at 4° C. The volume of the labeled sample was reduced to 60 μl using a viva spin column (VIVA Science) and 100 μl of destreak solution (GE Healthcare) was added. The total sample volumes were adjusted to 260 μl by adding Rehydration buffer (7 M urea, 2 M thiourea, 4% CHAPS, 20 mg/ml DTT, 1% pharmalytes and trace amount of bromophenol blue). The samples were incubated at room temperature for 10 min on a shaker and centrifuged for 10 min at 16000× gravity. The supernatants were loaded onto a 13 cm IPG strip holder (GE Healthcare).

2-Dimensional Differential In-Gel Electrophoresis (2-D DIGE):

Thirteen cm IPG strips (pH 3-10) were put on the loaded samples and 1 ml of mineral oil was added on top of the strip. Isoelectric focusing gels (IEF) were run following the protocol provided by the manufacturer (GE Healthcare). Upon completion of the IEF, the strips were equilibrated in buffer 1 (50 mM Tris-HCl, pH 8.8, containing 6 M urea, 30% glycerol, 2% SDS, trace amount of bromophenol blue and 10 mg/ml DTT) for 15 minutes and buffer 2 (50 mM Tris-HCl, pH 8.8, containing 6 M urea, 30% glycerol, 2% SDS, trace amount of bromophenol blue and 45 mg/ml DTT) for 10 minutes with gentle agitation. The IPG strips were then rinsed once in the SDS-gel running buffer, transferred to SDS-Gel (9-12% SDS-gel prepared using low florescent glass plates) and sealed with 0.5% (w/v) agarose solution (in SDS-gel running buffer). The electrophoresis was performed at room temperature until the dye fronts run out of the gels.

Image Scan and Data Analysis:

Upon completion of the electrophoresis, the gels were scanned using Typhoon TRIO (Amersham BioSciences) following the manufacturer's protocols and default parameter settings. The scanned images were then processed by Image Quant software (version 5.0, Amersham BioScience). Examples of scanned gels for ADDL are shown in FIG. 1. The quantitative analysis of protein spots were performed using DeCyder software (version 6.0).

Mass Spectometry:

Protein spots of interest on the 2D-gels were picked by Ettan Spot Picker (Amersham BioSciences) and subjected to in-gel trypsin digestion, peptide extraction, and desalting prior to MALDI-TOF/MS-MS (ABI 4700, Applied Biosystems). Protein spots were selected based on the differential fluorescent intensity between ADDL treated and control samples (brighter spots contain higher protein levels arising from higher affinity to ADDLs during the immunopercipitation). Identified amino acid sequences are shown in Table 4.

TABLE 4

Identified ADDL binding epitopes
Peptide Sequence

AVIMFANEDDIR (SEQ ID NO. 2)

ASIDGFDQYFRSQTLANNR (SEQ ID NO. 3)

ASIDGFDQYFR (SEQ ID NO. 4)

CTENVPVTDFFVGPVCIIPK (SEQ ID NO. 5)

TABLE 4-continued

Identified ADDL binding epitopes
Peptide Sequence

SSVWDERHDSHIPLEDCR (SEQ ID NO. 6)

HDSHIPLEDCR (SEQ ID NO. 7)

Figure 2:
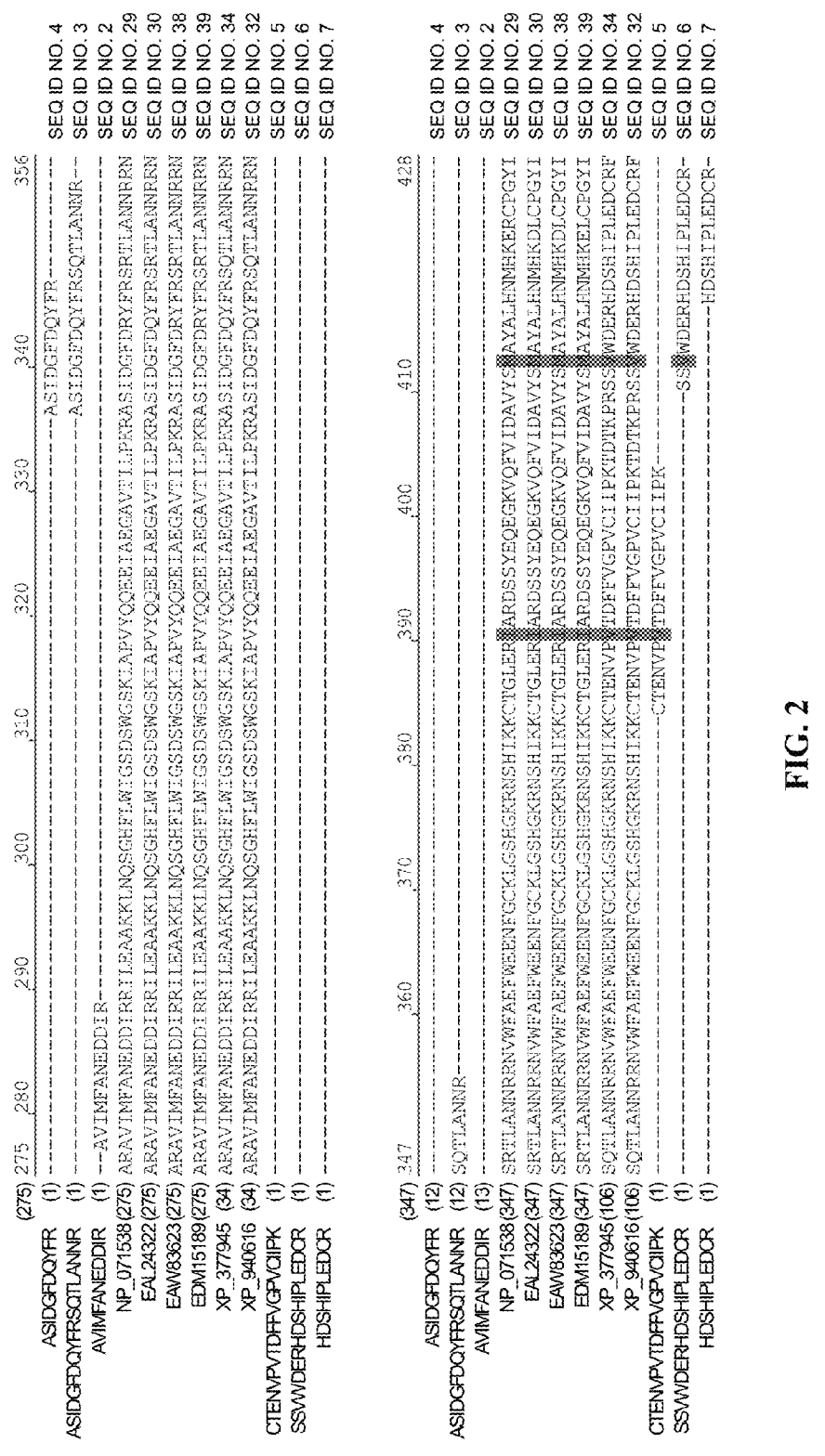

Identified ADDL binding epitopes were analyzed using BLASTP search for identification of related protein sequences (FIG. 2 and FIG. 3) (Altschul et al. (1997) Nucleic Acids Res. 25:3389-3402.). Similarity is based on a comparison or alignment of two or more amino acid or nucleotide sequences. Percent similarity can be determined by methods well-known in the art (Higgins and Sharp (1988) Gene 73:237-244 and programs for determining sequence identity for example Vector NTI (Invitrogen) and DNASTAR Inc).

The identified peptide sequences partially aligned to known/expressed metabotropic Glutamate receptors (FIG. 3 and FIG. 4). The "percent identity" of the identified peptide sequences depends on species from which the Glutamate receptor originated and is dependent on the peptide queried (Table 5). This data provides the first evidence of a novel ADDL receptor (ACU-mGlu receptor).

TABLE 5

Sequence homology to the most similar previously identified or predicted polypeptides

| Sequence | Amino Acid Position | Identity | GenBank Accession No./Description (Last Accessed on Nov. 26, 2007) |
|---|---|---|---|
| AVIMFANEDDIR (SEQ ID NO. 2) | 277-288 | 100% | EAL24322.1 - Glutamate receptor, metabotropic 8 [Homo sapiens] |
| | 277-288 | 100% | EDM15189.1 - Glutamate receptor, metabotropic 8, isoform CRA_a [Rattus norvegicus] |
| | 277-288 | 100% | NP_032200.2 - Glutamate receptor, metabotropic 8 [Mus musculus] |
| ASIDGFDQYFRSQT LANNR (SEQ ID NO. 3) | 91-113 | 100% | XP_377945.3 and XP_940616.1 - Predicted similar to glutamate receptor, metabotripic 8 [Homo sapiens] |
| | 336-354 | 94% | EAL24322.1 - Glutamate receptor, metabotropic 8 [Homo sapiens] |
| | 336-354 | 89% | EDM15189.1 - Glutamate receptor, metabotropic 8, isoform CRA_a [Rattus norvegicus] |
| | 336-354 | 89% | NP_032200.2 - Glutamate receptor, metabotropic 8 [Mus musculus] |
| ASIDGFDQYF (SEQ ID NO. 4) | 95-105 | 100% | XP_377945.3 and XP_940616.1 - Predicted similar to glutamate receptor, metabotripic 8 [Homo sapiens] |
| | 336-346 | 100% | EAL24322.1 - Glutamate receptor, metabotropic 8 [Homo sapiens] |
| | 336-346 | 90% | EDM15189.1 - Glutamate receptor, metabotropic 8, isoform CRA_a [Rattus norvegicus] |
| | 336-354 | 90% | NP_032200.2 - Glutamate receptor, metabotropic 8 [Mus musculus] |
| CTENVPVTDFFVGP VCIIPK (SEQ ID NO. 5) | 143-162 | 100% | XP_377945.3 and XP_940616.1 - Predicted similar to glutamate receptor, metabotripic 8 [Homo sapiens] |
| | 141-160 | 100% | XP_001147252.1 - Predicted similar to metabotropic glutamate receptor 8 precursor [Pan troglogytes] |
| | 92-109 | 66% | NP_001039177.1 - Novel protein similar to Tmem30b [Xenopus tropicalis]. |

TABLE 5-continued

Sequence homology to the most similar previously identified or predicted polypeptides

| Sequence | Amino Acid Position | Identity | GenBank Accession No./Description (Last Accessed on Nov. 26, 2007) |
|---|---|---|---|
| SSVWDERHDSHIPL EDCR (SEQ ID NO. 6) | 167-184 | 100% | XP_377945.3 and XP_940616.1 - Predicted similar to glutamate receptor, metabotripic 8 [Homo sapiens] |
| | 167-184 | 100% | XP_001147252.1 - Predicted similar to metabotropic glutamate receptor 8 precursor [Pan troglogytes] |
| | 50-61 | 64% | XP_001314382.1 - C2 domain containing protein [Trichomonas vaginalis G3] |
| HDSHIPLEDCR (SEQ ID NO. 7) | 176-186 | 100% | XP_377945.3 and XP_940616.1 - Predicted similar to glutamate receptor, metabotripic 8 [Homo sapiens] |
| | 176-186 | 100% | XP_001147252.1 - Predicted similar to metabotropic glutamate receptor 8 precursor [Pan troglogytes] |
| | 8-18 | 73% | YP_982675 - hypothetical protein Pnap_2447 [Polaromonas naphthalenivorans] |

The computer predicted sequences (XP_377945 and XP_940616) shows that the possible chromosomal location of the ADDL receptor is at 7q11.21, whereas the closest identified protein, metabotropic glutamate receptor 8 (mGluR8), is located at 7q31.3 to 32.1.

The identified peptide sequences provides the first biological evidence for the existence of a novel ADDL receptor. These peptides have overall low sequence identity to any metabotropic glutamate receptor. However, these same sequences maintain four conserved residues (S-----H--H--L) at positions S137, H143, H146, and L149 of SEQ ID NO. 1, which are conserved in the metabotropic glutamate receptor family (FIG. 3). This observation supports that the ADDL receptor is a novel receptor variant of the metabotropic glutamate receptor family.

Domain 1:
ASIDGFDQYFRSQTLANNR

ASIDGFDQYFR

Domain 2:
SSVWDERHDSHIPLEDCR

HDSHIPLEDCR

Example 3

Generation of Blocking Antibodies

Using methods known in the art, some of which are described herein, antibodies that modulate and inhibit ADDL binding to ADDL receptors are derived from any one or more than one of the following methods including synthetic peptides comprising identified or neighboring sequences; purified proteins of the mGluR class receptors (full length or partial clones containing the extracellular domain); three dimensional modeling and rational design of epitopes; or peptides or proteins designs, which are not restricted to any species sharing sequence identity/similarity with identified epitopes of SEQ ID NOS. 2 through 7. After generation of the antibodies, they are selected by screening assays, which identify one or more antibodies used to block ADDL binding to neuronal cells or cells expressing target receptors; inhibition of ADDL binding or ADDL binding competent mimetic structures measured in the presence of identified agonists/antagonist; inhibition of the endogenous ligand glutamate or small molecules which may act as co-agonist to confer structural changes which promote ADDL binding/inhibition; the properties of antibodies that block ADDL binding to receptors, which are not restricted to the primary sequence information, i.e linear binding epitopes; and identification of ADDL binding epitopes to mGluR class receptor, which will provide the basis for rational design of neighboring sequences and subsequent antibody generation.

Synthetic short peptides are used to generate protein-reactive antibodies, which can be concatormerized to enhance antibody production (see, Example 1). The advantage of immunizing with synthetic peptides is that unlimited quantity of pure stable antigen can be used. This approach involves synthesizing short peptide sequences, coupling them to a large carrier molecule, and immunizing the animal of choice with the peptide-carrier molecule.

A good response to the desired peptide usually can be generated with careful selection of the sequence and coupling method. Most peptides can elicit a good response. The advantage of anti-peptide antibodies is that they can be prepared immediately after determining the amino acid sequence of a protein and the particular regions of a protein can be targeted specifically for antibody production.

The successful production of anti-peptide antibodies is often determined by the prediction of the location of certain peptide sequences in the three-dimensional structure of the protein. Protein prediction programs are available for such analysis (e.g. SWISS-MODEL, 3Djigsaw, CPHmodels, ESyPred3D, Geno3d, SDSC1, 3D-PSSM, Fugue, HHpred, Libellua, LOOPP, SAM-T02, Threader, ProSup, SWEET, HMMSTR/Rosetta, Swiss-PdbViewer, MODELLER, STRUCTFAST, Folding@home, Rosetta@home, Human Proteomic Folding Project, Predictor@home, and TANPAKU). Important factors to consider include protein hydrophilicity and flexibility.

Another peptide method used in anti-peptide antibody production is the Multiple Antigenic Peptide system (MAPs). The advantage of MAPs is that the conjugation method is not necessary. No carrier protein or linkage bond is introduced into the immunized host. Another system is described in Horvath (cite) termed Lipid Core Peptides (LCP). The antibody titer is higher (3200-fold) with the LCP system, than found with CFA.

TABLE 6

Example for synthesis of Multiple Antigenic Peptides

| SEQ ID NO. | Sequence | Species |
|---|---|---|
| 26 | Ac-FDQYFRSQTLGG-MAP8 | RAT/HU |
| 27 | Ac-FDRYFRSRTLGG-MAP8 | RAT/HU |
| 28 | Ac-FDDYFLKLRLGG-MAP8 | RAT/HU |

Yet another method uses ImmunoPrecise, which is able to develop hybridomas in both rats and mice against individual amino acids, (in) organic compounds, peptides, post-translational modifications including phosphorylation, acetylation and methylation along with native and recombinant proteins as well as polyclonal antibodies in a variety of species including rabbit, goat and sheep against a variety of immunogens. Methods known in the art include humanization and optimization of antibodies, non-limiting examples are described herein.

Example 4

Developmental Progression of ADDL Binding to Rat Hippocampal Neurons

The initial identification of peptide fragments similar to mGluR8 was based on co-immunoprecipitation of ADDL with adult rat hippocampus synaptic fractions. Primary hippocampal cultures are a well established model system for ADDL binding and signaling (Lacor et al. (2004) J. Neurosci. 24(45):10191-10200 and Shanker et al. (2007) Neurosci. 27(11):2866-2875) bridging biological findings in vivo. ADDL binding has been shown to follow a developmental profile of neuronal maturation in vitro and is most prominent in mature, 21 days in vitro (DIV21), neuronal cultures. (FIG. 4).

Example 5

Characterization of mGluR8 Expression in Rat Primary Hippocampal Neurons

Western blot analysis was conducted to determine whether mGluR8 could be detected in hippocampal neurons. Dissociated hippocampal cells were plated at a density of 80,000 cells/well into 24-well poly-D-Lysin coated plates and allowed to differentiate. Cells were harvested at indicated time points (days in vitro (DIV) 3; 10; 24; 31; 38; 45) using 100 µl of SDS-loading buffer (Invitrogen) and lysed immediately. Samples were heated for 15 min at 95 C and equal volumes were loaded onto a 4-12% Bis-Tris gel (Invitrogen). Expression of mGluR8 in cultured neurons was detected via chemoluminescence using a polyclonal antibody raised against a c-terminal mGluR8 peptide that is conserved in human and rodent sequences. (Chemicon Ab9451), and distinct from sequences of other known mGluR subtypes.

Figure 5:
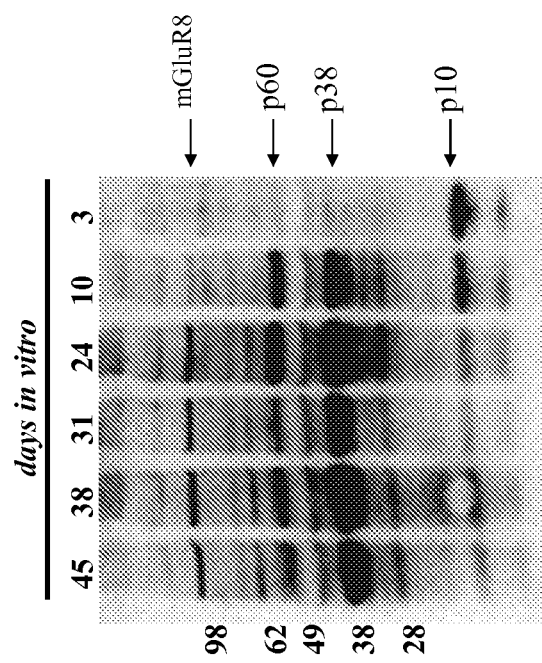
FIG. 5 shows developmental expression of mGluR8. The full length protein, mGluR8, is located at 101 kDa. Additionally, three potential mGluR8 variants (p60, p38, and p10, indicated by arrows) are detectable in cultured neuronal cells. Numeric values to the left of the figure indicate the corresponding size of the proteins as measured by kDa.

The results of this experiment show that mGluR8, or an mGlur8-like immunoreactive protein (101 kDa) is developmentally regulated. As the neuronal cells mature during in vitro culture, the intensity of the mGluR8 immunoreactive protein increases. (FIG. 5) This increase parallels an increase in the extent of punctate ADDL binding as shown in Example 4 and FIG. 4. The western blot reveals three lower molecular weight immunoreactive bands (p60, p38 and p10), in addition to protein band corresponding to a full-length 101 kDa mGluR8 protein. These bands may be indicative of a novel mGluR8 variant and they may arise from proteolysis of full-length mGlur8 or a novel, full-length variant of mGlur8.

The pronounced increase of the mGlur8 immunoreactive protein in these hippocampal neurons is a surprising finding, in view of recent results showing prominent mGluR8 modulatory activity in neonatal hippocampal slices, but not in adult slices, where synaptic transmission was not attenuated by (S)-DCPG, an mGluR8-selective agonist. (Ayala et al. (2008) Neuropharmacology 54:804-814) The strong expression in developed neurons is also surprising, given the observation that hippocampal mGluR8 expression is pre-synaptic and limited to nerve terminals of GABAergic neurons projecting into CA1. (Ferraguti et al. (2005) J. Neuroscience 25:10520-10536). In situ hybridization using an mGluR8-specific oligonucleotide probe showed no mGluR8 mRNA in hippocampal CA1 neurons, suggesting that the mGluR8-positive nerve terminals detected by Ferraguti et al. in the hippocampus originated from extra-hippocampal neurons or CA3 pyramidal neurons. It is noteworthy that the cultured hippocampal neurons of the present examples are predominantly CA1-type pyramidal neurons that would not be expected to express mGluR8 to a significant extent.

Example 6

Co-Immunopercipitation of ADDL Receptor Complex

Figure 6:
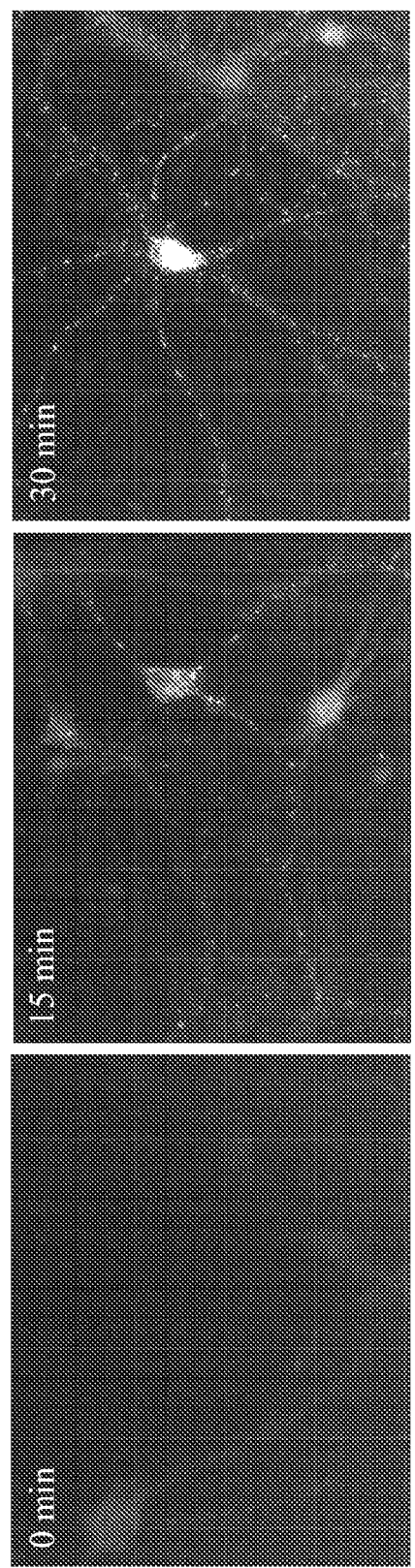
FIG. 6 shows ADDL assembly on neurons (22 days of in vitro culture) over time. Time periods of 0 min, 15 min and 30 min are indicated.

Hippocampal neurons were plated in 10 cm dishes at a density of 2.5 million cells and allowed to develop in vitro for twenty two days (DIV22). $A\beta_{1-42}$ samples were prepared from HFIP film and dissolved in anhydrous DMSO to a final concentration of 100 µM. All samples were further diluted with DMSO to 10 µM stock. The 10 µM DMSO stock was then diluted to either 0.1 nM or 10 nM $A\beta_{1-42}$ in neural basal media and then incubated with neuronal cells, in addition to respective DMSO vehicle controls for 30 min at 37° C. and 5% $CO_2$ to allow ADDL formation on cells. Immunofluorescent detection with 5 nM of an ADDL selective antibody show increased dendritic binding of ADDLs within 30 min of incubation (FIG. 6).

Figure 7:
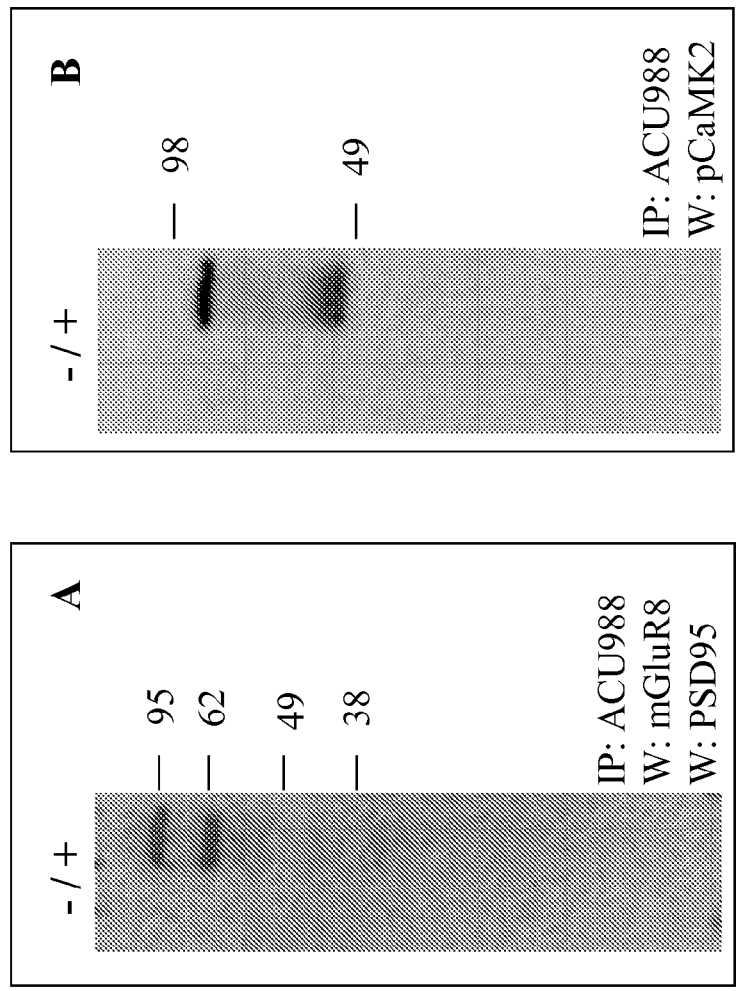
FIG. 7, panels A and B, show co-immunoprecipitation of proteins as part of the ADDL interacting receptor complex. (A) A novel mGluR8-immunoreactive protein at a size of approximately 62 kDa and the post synaptic density protein (PSD95) at 95 kDa are shown. (B) An unidentified phosphorylated protein of 95 kDa which is part of the ADDL interacting receptor complex and the phosphorylated CaM kinase II α subunit are shown.

The above cells were then briefly washed with warm phosphate buffered saline (PBS) and lysed using cell extraction buffer (Biosource, FNN001) containing a protease inhibitor cocktail (Sigma P2714) and a phosphatase inhibitor cocktail (Sigma,2850). The protein concentration of the treated cell-lysate was determined using Commassie Plus (Pierce 23236). A total of 600 µg of each cell-lysate was incubated with 6 µg of an anti-ADDL antibody (See, Lambert et al. (2007) J. Neurochem. 100(1):23-35 and Lambert et al. (2001) J. Neurochem. 79:595-605) overnight at 4° C. on a shaker. The following day, 50 µl of protein A/G agarose (Santa Cruz) was added for 2 h at 4° C. After brief centrifugation at 4° C. the pellet was washed three consecutive times with buffer (10 mM Tris, 0.1% SDS, 1 mM EDTA). All liquid was removed and the pellet was resuspended in 2× sample buffer (Invitrogen) and heated for 2 min at 92° C. All samples were spun down briefly prior to loading on a 4-12% Bis-Tris gel. Following electrophoresis, samples were transferred onto a PVDF membrane (Invitrogen) by incubation overnight in transfer buffer (Tris base 3.03 g glycine, 14.4 g methanol, and 200 ml 0.1% SDS per liter). The PVDF membrane was blocked with 2% Advance blocking reagent and incubated with the primary anti-mGluR8 antibody (Chemicon mGluR8 9451 lot 0701049511) for 3 h at room temperature. After washing the PVDF membrane several times with PBST (0.05% Tween-20), the secondary anti-rabbit HRP coupled antibody (1:2000) was added for 2 h at room temperature. The membrane was subsequently washed with PBST and incubated with an anti-PSD95 antibody (Abcam ab18258). Chemiluminescent detection of the co-immunopercipitated proteins and postsynaptic density-95 (PSD95) was done using Amersham Advance Kit (FIG. 7). The co-immunopercipitated protein which binds to ADDL proteins and binds to the anti-mGluR8 antibody is not the native mGluR8 receptor. The mGluR8 receptor is 101 kDa, while the novel protein identified herein migrates at approximately 62 kDa (FIG. 7A).

In addition, the above membrane was stripped using Restore™ Western Blot Stripping Buffer (Pierce#21059) and reprobed with anti-phospho CaM kinase II α subunit antibody (Chemicon 05-533). Chemiluminescent detection was conducted as described above. In addition to the phosphorylated CaM kinase II α subunit, a phosphorylated protein of 95 kDa is detectable as part of the ADDL interacting receptor complex (FIG. 7B).

Example 7

Generation of Antibodies Using Multiple Antigenic Peptides System

BALB/c mice were immunized using the Multiple Antigenic Peptides (MAPs) described in Table 6. The antigen was solubilized in phosphate buffered saline and mice were immunized with four standard prime immunizations or alternatively four rapid prime booster immunizations.

Standard Prime Immunization

Mice were initially immunized by intraperitoneal injections with 50 ug of antigen per mouse in Complete Freund's Adjuvant. Four subsequent boosts were administered as above, spaced at 3 week intervals, with Incomplete Freund's Adjuvant. When the serum titre had risen more than 10-fold from a pre-immune serum sample, as determined by ELISA, the highest responders were each boosted intravenously with 10 ug of antigen, in 100 ul of sterile PBS (pH 7.4.)

Rapid Prime Immunization

This technique uses the same steps as Standard Prime Immunization, but is completed in 18 days.

Figure 8:
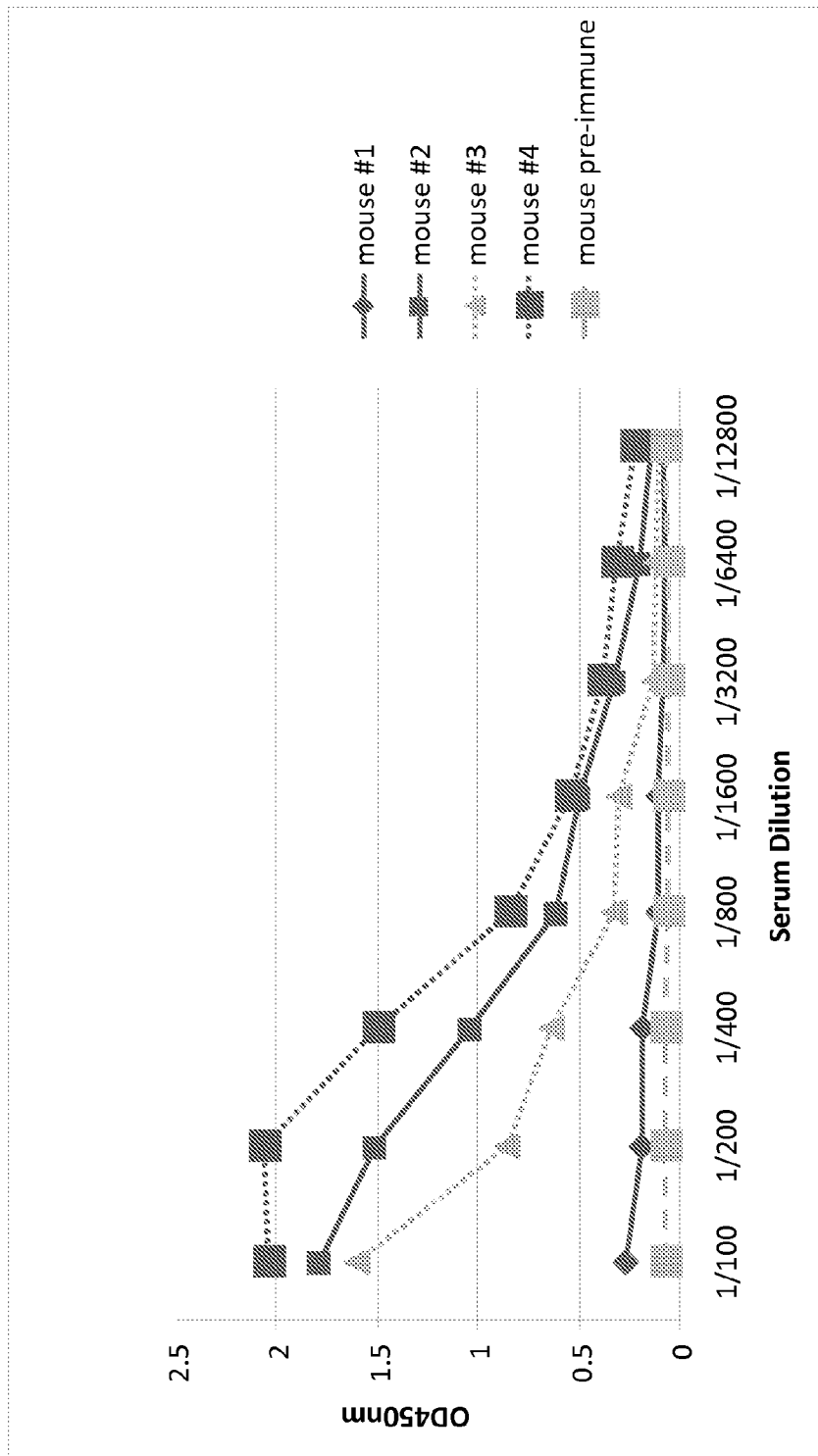
FIG. 8 shows the ELISA titration of mouse immunsera directed against Ac-FDQYFRSQTLGG-MAP8 (SEQ ID NO. 26). Four mice were immunized, each represented by a distinct figure legend: mouse #1=dark gray diamond with corresponding solid line; mouse #2=dark gray small square with corresponding solid line; mouse #3=light gray triangle with corresponding dotted line; and mouse #4=dark gray large square with corresponding dotted line. The negative control of a pre-immune mouse is represented by a large light gray square and corresponding dashed line. The X axis indicates the serum dilution, while the Y axis indicates the ELISA fluorescence detected at 450 nm.

Following the 4$^{th}$ booster immunization, the immunesera of each mouse was assayed against the antigen by ELISA (FIG. 8). One µg per well of antigen in carbonate coating buffer pH9.6 at 100 µL/well is incubated overnight at 4° C. Blocking was done with 3% skim milk powder in PBS pH 7.4 at 100 µL/well for 1 h at room temperature.

Primary Ab: Serum from test bleed after boost titrated in PBS-Tween pH 7.4 at 100 µL/well and incubated for 1 h at room temperature.

Secondary Ab: 1/10000 Goat anti-mouse IgG Fc-HRP (Pierce cat#31328) and Goat anti-mouse (H+L)-HRP (Pierce cat#31430) at 100 µL/well is incubated for 1 h at 37° C.

Substrate: TMB (BioFx cat#TMBW-1000-01) at 50 µL/well and stopped with an equal volume of 1 M HCl after 15 minutes. OD is read at 450 nm.

Fusion Method

Three days following immunization, the donor mice were sacrificed and the spleen cells were harvested and pooled. Fusion of the splenocytes with SP2/0 BALB/c parental myeloma cells was performed as previously described in Kohler et al. (1975) Nature 25:256-259, except that one-step selection and cloning of the hybridomas was performed using the Clone-EZ method (Immuno-Precise). This proprietary semi-solid medium allows HAT selection and cloning in a single step and eliminates the overgrowth of slower growing desirable clones by faster growing, perhaps undesirable, hybridomas. Clones were picked 11 days post fusion and resuspended in wells of 96-well tissue culture plates in 200 µl of D-MEM (Invitrogen) medium containing 1% hypoxanthine/thymidine, 20% fetal bovine serum, 2 mM GlutaMax I, 1 mM Sodium Pyruvate, 50 µg/ml Gentamycin, 1% OPI and 0.6 ng/ml IL-6. After 4 days, the supernatants were screened by ELISA for antibody activity on plates coated with 1 µg/well of purified ISAV antigen. Putative positive hybridomas were re-cloned by limited dilution cloning to ensure monoclonality and the antibodies were further characterized on Western blots of ISAV antigen.

Clone-EZ is a 1-step fusion and cloning medium, which has several advantages over standard hybridoma selection and cloning methods, including 1) selection and cloning of hybridomas are performed in one step thus minimizing time and materials required; 2) plating of initial fusion mixture and simultaneous cloning are performed in minutes as compared to hours when using conventional methods; 3) growth conditions have been optimized to give high plating efficiency ensuring maximum hybridoma yield; 4) large numbers of hybridomas can be selected and tested; 5) one to two thousand individual clones can be grown in twelve 60 mm petri dishes in a single step; 6) direct cloning eliminates overgrowth of some hybridomas thereby allowing the selection of valuable slow-growing colonies (this is not possible by any other method); 7) undesirable fibroblasts do not grow in this medium; 8) contamination of cultures is minimized because of fewer manipulations—little maintenance of cultures is required; 9) the amount of testing is decreased since multiple identical clones are not produced as in suspension cultures. The procedure results in estimated savings of 18-20 days and has allowed the isolation of rare hybridomas secreting antibodies to minor antigens in complex mixtures.

Unlike the standard limiting dilution technique for producing hybridomas, a special formulation of enriched semi-solid medium as used. The medium has been optimized for the growth of single cells, ensuring the development of valuable slow-growing clones. The significant advantage that this technology offers over standard techniques is that it allows the identification and isolation of every antigen specific hybridoma in the population. When screening hybridomas, one to two thousand individual clones are looked at (i.e. not a heterogeneous population as in the common method), thus allowing accurate identification and saving every antigen specific hybridoma cell line. This is not possible by any other method currently used to make monoclonal antibodies. As a result, it is possible to screen large numbers of hybridoma clones and choose the best clones that are suitable for commercial development.

Revival of Slow Growing Hybridoma Clones

Hybridoma cell lines that are growing slowly or appear unhealthy can typically be rescued by the addition of a rich growth media containing: D-MEM (Invitrogen) medium with 1% hypoxanthine/thymidine, 20% fetal bovine serum, 2 mM GlutaMax I, 1 mM Sodium Pyruvate, 50 µg/ml Gentamycin, 1% OPI, 20% conditioned EL-4 tissue culture supernatant and 0.6 ng/ml IL-6. EL-4 is a murine thymoma cell line, which when stimulated with phorbal 12-myristate 12-acetate (PMA, from Sigma, cat #P-8139) causes the cells to secrete interleukin 2 (IL-2), a B cell differentiating factor (EL-BCDF-nak), and two B cell growth factors (BSF-p1 and EL-BCGF-swa) and other additional lymphokines, which greatly enhance lymphocyte growth and differentiation as described in Ma et al. (1984) In vitro 20:739.

Antibody Testing on Primary Neuronal Cultures

Tissue culture supernatant of selected antibody secreting clones was collected and used for testing mAb blocking properties on differentiated primary hippocampal cultures from rat. Supernatants (50 µg/ml) were serially diluted in 37° C. Neurobasal media (Invitrogen). The neuronal media of the primary neuronal cultures was removed and replaced with mAb containing Neurobasal media. Neurons were incubated for 20 min at 37° C. and 5% $CO_2$ in the presence of blocking mAbs. Subsequently, ADDLs ($A\beta_{1-42}$ soluble oligomers) were added to the cells at a final concentration of 5 nM and allowed to bind for 20 min. Cells were washed briefly with warm phosphate buffered saline (PBS) and fixed with 4% paraformaldehyd in PBS. Unspecific binding sites were blocked with 5% BSA (bovine serum albumin) in PBS for 30 min and an ADDL selective mouse monoclonal antibody (ACU954, 0.2 µg/ml) was incubated overnight at 4° C. The following day, cells were washed three times with PBS and incubated with a goat anti-mouse secondary antibody conjugated to Alexa 647 fluorophore for 2 h at room temperature. Nuclear dye (Hoechst) was added at a concentration of 50 ng/ml. After washing three times with PBS the cells were mounted on glass coverslips and imaged at 63× on a Zeiss Z1 microscope.

Figure 9:
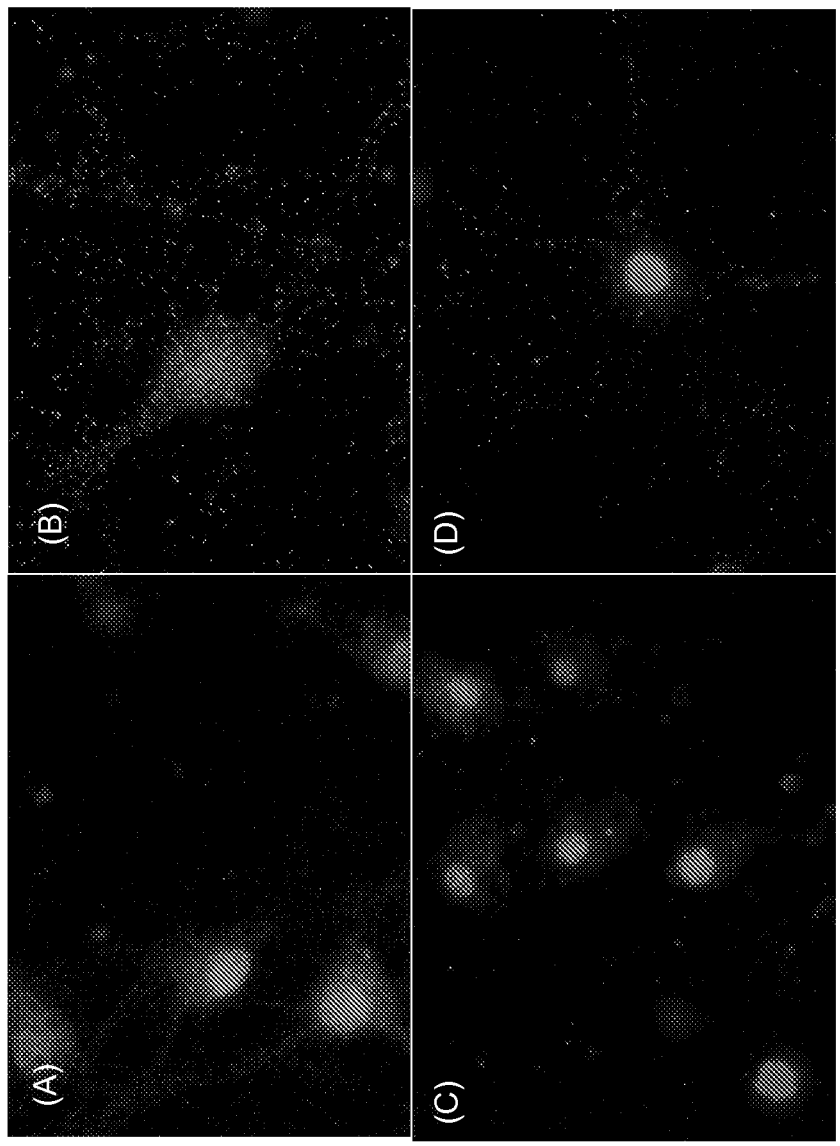
FIG. 9, panels A to D, shows the inhibition of ADDL binding to primary hippocampal neurons by hybridoma secreted antibodies. (A) Vehicle negative control with no dendritic spine labeling. (B) Positive control of ADDL binding to the dentritic spines of primary hippocampal neurons. Antibody inhibition of ADDL binding by antibodies secreted from hybridoma clones 1A8 (C) or 1C12 (D) at dilutions of 1:10.
Figure 10:
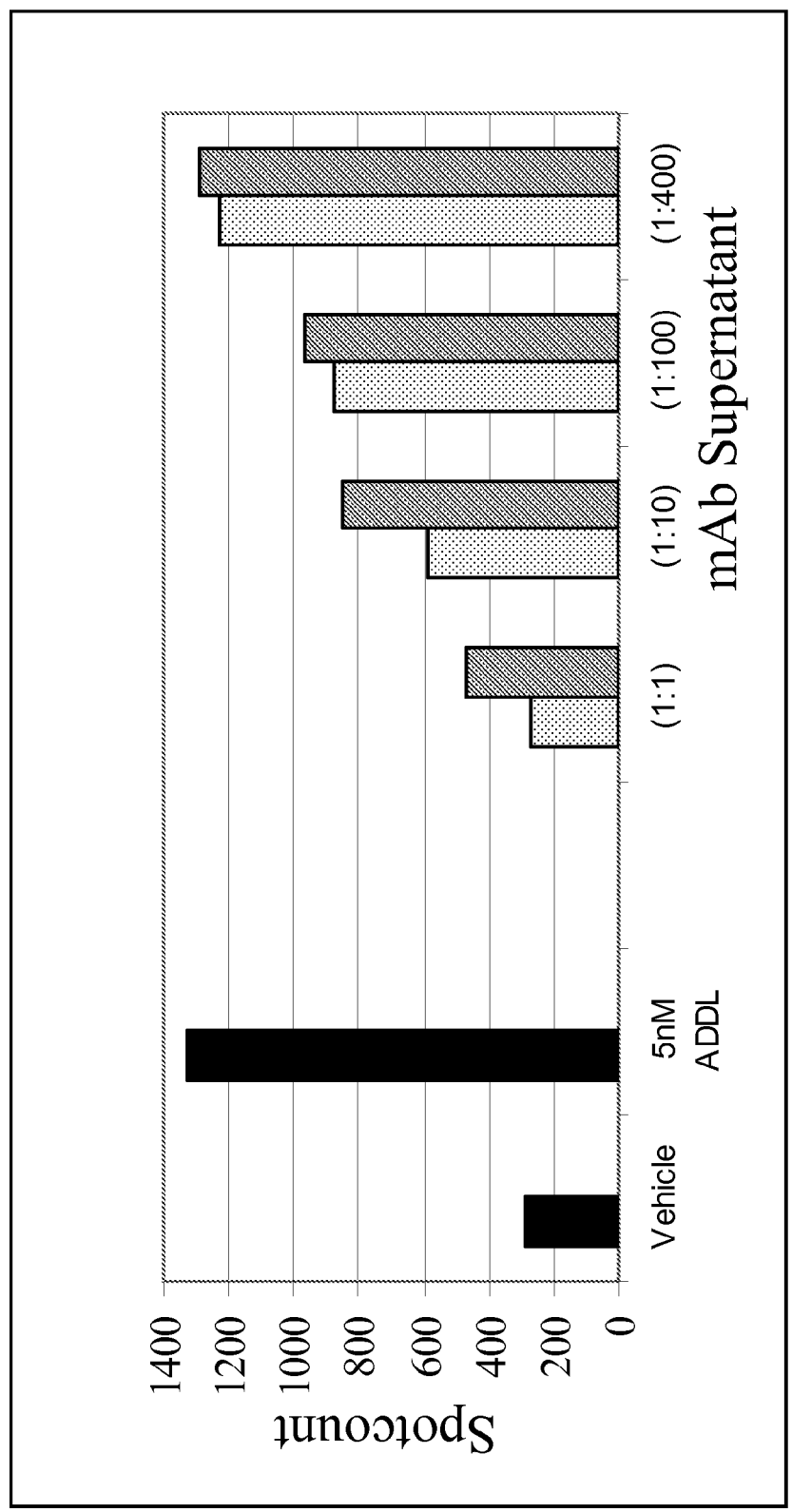
FIG. 10 shows the concentration dependent antibody inhibition of ADDL binding to primary hippocampal neurons. The X axis indicated the experimental condition tested, while the Y axis indicates the quantitative measurement of the ADDL binding as measured in Spotcounts. Light gray bars indicated antibodies secreted from hybridoma clone 1A8 while hybridoma clone 1C12 is indicated dark gray bars. Vehicle and control are shown in black bars.

Both hybridoma clones 1A8 and 1C12 secreted antibodies that inhibit binding of 5 nM ADDLs to the dendritic spines of the primary hippocampal neurons at a dilution of 1:10 as compared to the positive control of 5 nM ADDL alone (FIG. 9). Various dilutions of the clones 1A8 and 1C12 secreted antibodies were quantified for inhibition of ADDL binding. This quantification was done with Image J at 20× magnification using protocols described in Prodanov et al. (2006) J. Neurosci. Methods 151(2):168-177. Both clones show concentration dependent inhibition of ADDL binding between 1:1, 1:10, 1:100, and 1:400 dilutions (FIG. 10).

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. An antibody that binds an amyloid β-derived diffusible ligand receptor polypeptide, said polypeptide comprising amino acid sequences selected from the group consisting of:

```
(a)    CTENVPVTDFFVGPVCIIPK      (SEQ ID NO: 5)
       and
(b)    SSVWDERHDSHIPLEDCR        (SEQ ID NO: 6).
```

2. An antibody that binds two binding regions of an amyloid β-derived diffusible ligand receptor polypeptide, the two binding regions being non-contiguous
wherein the first binding region is selected from the group of amino acid sequences consisting of:

```
(a)    CTENVPVTDFFVGPVCIIPK;     (SEQ ID NO: 5)
(b)    SSVWDERHDSHIPLEDCR;       (SEQ ID NO: 6)
       and
(c)    HDSHIPLEDCR;              (SEQ ID NO: 7)
``` and wherein the second binding region is different from the first binding region and is selected from the group of amino acid sequences consisting of:

```
(d)    AVIMFANEDDIR;             (SEQ ID NO: 2)
(e)    ASIDGFDQYFRSQTLANNR;      (SEQ ID NO: 3)
(f)    ASIDGFDQYFR;              (SEQ ID NO: 4)
(g)    CTENVPVTDFFVGPVCIIPK;     (SEQ ID NO: 5)
(h)    SSVWDERHDSHIPLEDCR;       (SEQ ID NO: 6)
       and
(i)    HDSHIPLEDCR               (SEQ ID NO: 7).
```

3. An antibody that binds at least one amyloid β-derived diffusible ligand receptor polypeptide selected from the group consisting of:
(a) CTENVPVTDFFVGPVCIIPK (SEQ ID NO: 5);
(b) SSVWDERHDSHIPLEDCR (SEQ ID NO: 6); and
(c) HDSHIPLEDCR (SEQ ID NO: 7);
wherein the antibody optionally further binds to at least one polypeptide selected from the group consisting of AVIMFANEDDIR (SEQ ID NO: 2), ASIDGFDQYFRSQTLANNR (SEQ ID NO: 3) and ASIDGFDQYFR (SEQ ID NO: 4).

4. A biologically active fragment of the antibody of claim 1, 2 or 3.

5. The antibody of claim 4, wherein the antibody is a polyclonal antibody, a monoclonal antibody, a chimeric antibody or a humanized antibody.

6. A composition comprising the antibody of claim 1, 2 or 3 and a carrier.

7. A composition comprising the biologically active fragment of claim 4 and a carrier.

8. An isolated antibody-peptide complex comprising an antibody of any one of claim 1, 2 or 3 and a polypeptide that specifically binds to the antibody.

9. The isolated complex of claim 8, wherein the polypeptide is the polypeptide against which the antibody is raised.

10. The isolated complex of claim 8, wherein the antibody is a polyclonal antibody, a monoclonal antibody, a chimeric antibody or a humanized antibody.

11. An isolated antibody that inhibits binding of soluble amyloid β-derived diffusible ligand to a neural receptor and binds a polypeptide selected from the group consisting of:
(a) a polypeptide comprising amino acid sequence CTENVPVTDFFVGPVCIIPK (SEQ ID NO: 5) and SSVWDERHDSHIPLEDCR (SEQ ID NO: 6);
(b) a polypeptide comprising two non-contiguous binding regions, the binding regions comprising ASIDGFDQYFRSQTLANNR (SEQ ID NO: 3) and SSVWDERHDSHIPLEDCR (SEQ ID NO: 6); and
(c) a polypeptide comprising two non-contiguous binding regions, the binding regions comprising ASIDGFDQYFR (SEQ ID NO: 4) and HDSHIPLEDCR (SEQ ID NO: 7).

12. The antibody of claim 11, wherein the antibody binds two or more polypeptides of the group consisting of (a), (b) and (c).

13. A composition comprising an antibody of claim 11 or 12 and a carrier.

14. The composition of claim 13, wherein the carrier is a solid support.

15. The composition of claim 13, wherein the carrier is a pharmaceutically acceptable carrier.

16. An antibody that binds an amyloid β-derived diffusible ligand receptor polypeptide selected from the group consisting of:

```
(a)    CTENVPVTDFFVGPVCIIPK;     (SEQ ID NO: 5)
(b)    SSVWDERHDSHIPLEDCR;       (SEQ ID NO: 6)
       and
(c)    HDSHIPLEDCR               (SEQ ID NO: 7).
```

17. A biologically active fragment of the antibody of claim 16.

18. The antibody of claim 16, wherein the antibody is a polyclonal antibody, a monoclonal antibody, a chimeric antibody or a humanized antibody.

19. A composition comprising the antibody of claim 16 and a carrier.

20. A composition comprising the biologically active fragment of claim 17 and a carrier.

21. An isolated antibody-peptide complex comprising an antibody of claim 16 and a polypeptide that specifically binds to the antibody.

22. The isolated complex of claim 21, wherein the polypeptide is the polypeptide against which the antibody is raised.

23. The isolated complex of claim 21, wherein the antibody is a polyclonal antibody, a monoclonal antibody, a chimeric antibody or a humanized antibody.

24. An isolated antibody that inhibits binding of soluble amyloid β-derived diffusible ligand to a neural receptor and binds a polypeptide selected from the group consisting of:
- (a) a polypeptide comprising the amino acid sequence CTENVPVTDFFVGPVCIIPK (SEQ ID NO: 5);
- (b) a polypeptide comprising the amino acid sequence SSVWDERHDSHIPLEDCR (SEQ ID NO: 6); and
- (c) a polypeptide comprising the amino acid sequence HDSHIPLEDCR (SEQ ID NO: 7).

25. A composition comprising an antibody of claim 24 and a carrier.

26. The composition of claim 25, wherein the carrier is a solid support.

27. The composition of claim 25, wherein the carrier is a pharmaceutically acceptable carrier.

* * * * *

SEQUENCE LISTING

```
<160> NUMBER OF SEQ ID NOS: 39

<210> SEQ ID NO 1
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Arg Ala Val Ile Met Phe Ala Asn Glu Asp Asp Ile Arg Arg Ile
1               5                   10                  15

Leu Glu Ala Ala Lys Lys Leu Asn Gln Ser Gly His Phe Leu Trp Ile
            20                  25                  30

Gly Ser Asp Ser Trp Gly Ser Lys Ile Ala Pro Val Tyr Gln Gln Glu
        35                  40                  45

Glu Ile Ala Glu Gly Ala Val Thr Ile Leu Pro Lys Arg Ala Ser Ile
    50                  55                  60

Asp Gly Phe Asp Gln Tyr Phe Arg Ser Gln Thr Leu Ala Asn Asn Arg
65                  70                  75                  80

Arg Asn Val Trp Phe Ala Glu Phe Trp Glu Glu Asn Phe Gly Cys Lys
                85                  90                  95

Leu Gly Ser His Gly Lys Arg Asn Ser His Ile Lys Lys Cys Thr Glu
            100                 105                 110

Asn Val Pro Val Thr Asp Phe Phe Val Gly Pro Val Cys Ile Ile Pro
        115                 120                 125

Lys Thr Asp Thr Lys Pro Arg Ser Ser Val Trp Asp Glu Arg His Asp
    130                 135                 140

Ser His Ile Pro Leu Glu Asp Cys Arg Phe
145                 150

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 2

Ala Val Ile Met Phe Ala Asn Glu Asp Asp Ile Arg
1               5                   10

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Ile Asp Gly Phe Asp Gln Tyr Phe Arg Ser Gln Thr Leu Ala
1               5                   10                  15

Asn Asn Arg

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Ile Asp Gly Phe Asp Gln Tyr Phe Arg
1               5                   10

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Thr Glu Asn Val Pro Val Thr Asp Phe Phe Val Gly Pro Val Cys
1               5                   10                  15

Ile Ile Pro Lys
            20

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Val Trp Asp Glu Arg His Asp Ser His Ile Pro Leu Glu Asp
1               5                   10                  15

Cys Arg

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 7

His Asp Ser His Ile Pro Leu Glu Asp Cys Arg
1               5                   10

<210> SEQ ID NO 8
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Ile Asp Gly Phe Asp Gln Tyr Phe Arg Ser Gln Thr Leu Ala
1               5                   10                  15

Asn Asn Arg Arg Asn Val Trp Phe Ala Glu Phe Trp Glu Asn Phe
            20                  25                  30

Gly Cys Lys Leu Gly Ser His Gly Lys Arg Asn Ser His Ile Lys Lys
        35                  40                  45

Cys Thr Glu Asn Val Pro Val Thr Asp Phe Phe Val Gly Pro Val Cys
    50                  55                  60

Ile Ile Pro Lys Thr Asp Thr Lys Pro Arg Ser Ser Val Trp Asp Glu
65                  70                  75                  80

Arg His Asp Ser His Ile Pro Leu Glu Asp Cys Arg
                85                  90

<210> SEQ ID NO 9
<211> LENGTH: 462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gctcgagcag tgattatgtt tgccaatgag gatgacatca ggaggatatt ggaagcagca      60
aaaaaactaa accaaagtgg ccatttctc tggattggct cagatagttg gggatccaaa     120
atagcacctg tctatcagca agaggagatt gcagaagggg ctgtgacaat tttgcccaaa    180
cgagcatcaa ttgatggatt tgatcaatac tttagaagcc aaactcttgc caataatcga    240
agaaatgtgt ggtttgcaga attttgggag gagaattttg gctgcaagtt aggatcacat    300
gggaaaagga acagtcatat aaagaaatgc acagaaaatg tccctgtgac tgatttcttt    360
gtgggaccag tctgcatcat tcctaagact gacacaaagc cccgctcgag cgtgtgggat    420
gaacggcatg actcacacat tcccctggag gactgcaggt tt                       462

<210> SEQ ID NO 10
<211> LENGTH: 464
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base

```
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (51)..(51)
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other
<220> FEATURE:
<221> NAME/KEY: modified_base
<222> LOCATION: (60)..(60)
<223> OTHER INFORMATION: a, c, g, t, unknown or other
<220> FEATURE:
<221> NAME/KEY: modified_base
<222> LOCATION: (69)..(69)
<223> OTHER INFORMATION: a, c, g, t, unknown or other
<220> FEATURE:
<221> NAME/KEY: modified_base
<222> LOCATION: (78)..(78)
<223> OTHER INFORMATION: a, c, g, t, unknown or other
<220> FEATURE:
<221> NAME/KEY: modified_base
<222> LOCATION: (81)..(81)
<223> OTHER INFORMATION: a, c, g, t, unknown or other
<220> FEATURE:
<221> NAME/KEY: modified_base
<222> LOCATION: (90)..(90)
<223> OTHER INFORMATION: a, c, g, t, unknown or other
<220> FEATURE:
<221> NAME/KEY: modified_base
<222> LOCATION: (99)..(99)
<223> OTHER INFORMATION: a, c, g, t, unknown or other
<220> FEATURE:
<221> NAME/KEY: modified_base
<222> LOCATION: (102)..(102)
<223> OTHER INFORMATION: a, c, g, t, unknown or other
<220> FEATURE:
<221> NAME/KEY: modified_base
<222> LOCATION: (108)..(108)
<223> OTHER INFORMATION: a, c, g, t, unknown or other
<220> FEATURE:
<221> NAME/KEY: modified_base
<222> LOCATION: (114)..(114)
<223> OTHER INFORMATION: a, c, g, t, unknown or other
<220> FEATURE:
<221> NAME/KEY: modified_base
<222> LOCATION: (117)..(117)
<223> OTHER INFORMATION: a, c, g, t, unknown or other
<220> FEATURE:
<221> NAME/KEY: modified_base
<222> LOCATION: (126)..(126)
<223> OTHER INFORMATION: a, c, g, t, unknown or other
<220> FEATURE:
<221> NAME/KEY: modified_base
<222> LOCATION: (129)..(129)
<223> OTHER INFORMATION: a, c, g, t, unknown or other
<220> FEATURE:
<221> NAME/KEY: modified_base
<222> LOCATION: (132)..(132)
<223> OTHER INFORMATION: a, c, g, t, unknown or other
<220> FEATURE:
```

```
<221> NAME/KEY: modified_base
<222> LOCATION: (153)..(153)
<223> OTHER INFORMATION: a, c, g, t, unknown or other
<220> FEATURE:
<221> NAME/KEY: modified_base
<222> LOCATION: (159)..(159)
<223> OTHER INFORMATION: a, c, g, t, unknown or other
<220> FEATURE:
<221> NAME/KEY: modified_base
<222> LOCATION: (162)..(162)
<223> OTHER INFORMATION: a, c, g, t, unknown or other
<220> FEATURE:
<221> NAME/KEY: modified_base
<222> LOCATION: (165)..(165)
<223> OTHER INFORMATION: a, c, g, t, unknown or other
<220> FEATURE:
<221> NAME/KEY: modified_base
<222> LOCATION: (168)..(168)
<223> OTHER INFORMATION: a, c, g, t, unknown or other
<220> FEATURE:
<221> NAME/KEY: modified_base
<222> LOCATION: (174)..(174)
<223> OTHER INFORMATION: a, c, g, t, unknown or other
<220> FEATURE:
<221> NAME/KEY: modified_base
<222> LOCATION: (177)..(177)
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (186)..(186)
<223> OTHER INFORMATION: a, c, g, t, unknown or other
<220> FEATURE:
<221> NAME/KEY: modified_base
<222> LOCATION: (189)..(189)
<223> OTHER INFORMATION: a, c, g, t, unknown or other
<220> FEATURE:
<221> NAME/KEY: modified_base
<222> LOCATION: (198)..(198)
<223> OTHER INFORMATION: a, c, g, t, unknown or other
<220> FEATURE:
<221> NAME/KEY: modified_base
<222> LOCATION: (216)..(216)
<223> OTHER INFORMATION: a, c, g, t, unknown or other
<220> FEATURE:
<221> NAME/KEY: modified_base
<222> LOCATION: (219)..(219)
<223> OTHER INFORMATION: a, c, g, t, unknown or other
<220> FEATURE:
<221> NAME/KEY: modified_base
<222> LOCATION: (225)..(225)
<223> OTHER INFORMATION: a, c, g, t, unknown or other
<220> FEATURE:
<221> NAME/KEY: modified_base
<222> LOCATION: (228)..(228)
<223> OTHER INFORMATION: a, c, g, t, unknown or other
<220> FEATURE:
<221> NAME/KEY: modified_base
<222> LOCATION: (231)..(231)
<223> OTHER INFORMATION: a, c, g, t, unknown or other
<220> FEATURE:
<221> NAME/KEY: modified_base
<222> LOCATION: (240)..(240)
<223> OTHER INFORMATION: a, c, g, t, unknown or other
<220> FEATURE:
<221> NAME/KEY: modified_base
<222> LOCATION: (242)..(242)
<223> OTHER INFORMATION: a, c, g, t, unknown or other
<220> FEATURE:
<221> NAME/KEY: modified_base
<222> LOCATION: (244)..(244)
<223> OTHER INFORMATION: a, c, g, t, unknown or other
<220> FEATURE:
<221> NAME/KEY: modified_base
<222> LOCATION: (250)..(250)
<223> OTHER INFORMATION: a, c, g, t, unknown or other
```

-continued

```
<220> FEATURE:
<221> NAME/KEY: modified_base
<222> LOCATION: (259)..(259)
<223> OTHER INFORMATION: a, c, g, t, unknown or other
<220> FEATURE:
<221> NAME/KEY: modified_base
<222> LOCATION: (283)..(283)
<223> OTHER INFORMATION: a, c, g, t, unknown or other
<220> FEATURE:
<221> NAME/KEY: modified_base
<222> LOCATION: (292)..(292)
<223> OTHER INFORMATION: a, c, g, t, unknown or other
<220> FEATURE:
<221> NAME/KEY: modified_base
<222> LOCATION: (295)..(295)
<223> OTHER INFORMATION: a, c, g, t, unknown or other
<220> FEATURE:
<221> NAME/KEY: modified_base
<222> LOCATION: (298)..(298)
<223> OTHER INFORMATION: a, c, g, t, unknown or other
<220> FEATURE:
<221> NAME/KEY: modified_base
<222> LOCATION: (304)..(304)
<223> OTHER INFORMATION: a, c, g, t, unknown or other
<220> FEATURE:
<221> NAME/KEY: modified_base
<222> LOCATION: (310)..(310)
<223> OTHER INFORMATION: a, c, g, t, unknown or other
<220> FEATURE:
<221> NAME/KEY: modified_base
<222> LOCATION: (316)..(316)
<223> OTHER INFORMATION: a, c, g, t, unknown or other
<220> FEATURE:
<221> NAME/KEY: modified_base
<222> LOCATION: (334)..(334)
<223> OTHER INFORMATION: a, c, g, t, unknown or other
<220> FEATURE:
<221> NAME/KEY: modified_base
<222> LOCATION: (343)..(343)
<223> OTHER INFORMATION: a, c, g, t, unknown or other
<220> FEATURE:
<221> NAME/KEY: modified_base
<222> LOCATION: (346)..(346)
<223> OTHER INFORMATION: a, c, g, t, unknown or other
<220> FEATURE:
<221> NAME/KEY: modified_base
<222> LOCATION: (349)..(349)
<223> OTHER INFORMATION: a, c, g, t, unknown or other
<220> FEATURE:
<221> NAME/KEY: modified_base
<222> LOCATION: (352)..(352)
<223> OTHER INFORMATION: a, c, g, t, unknown or other
<220> FEATURE:
<221> NAME/KEY: modified_base
<222> LOCATION: (364)..(364)
<223> OTHER INFORMATION: a, c, g, t, unknown or other
<220> FEATURE:
<221> NAME/KEY: modified_base
<222> LOCATION: (367)..(367)
<223> OTHER INFORMATION: a, c, g, t, unknown or other
<220> FEATURE:
<221> NAME/KEY: modified_base
<222> LOCATION: (370)..(370)
<223> OTHER INFORMATION: a, c, g, t, unknown or other
<220> FEATURE:
<221> NAME/KEY: modified_base
<222> LOCATION: (373)..(373)
<223> OTHER INFORMATION: a, c, g, t, unknown or other
<220> FEATURE:
<221> NAME/KEY: modified_base
<222> LOCATION: (385)..(385)
<223> OTHER INFORMATION: a, c, g, t, unknown or other
<220> FEATURE:
<221> NAME/KEY: modified_base
<222> LOCATION: (391)..(391)
<223> OTHER INFORMATION: a, c, g, t, unknown or other
<220> FEATURE:
<221> NAME/KEY: modified_base
<222> LOCATION: (397)..(397)
```

<223> OTHER INFORMATION: a, c, g, t, unknown or other
<220> FEATURE:
<221> NAME/KEY: modified_base
<222> LOCATION: (403)..(403)
<223> OTHER INFORMATION: a, c, g, t, unknown or other
<220> FEATURE:
<221> NAME/KEY: modified_base
<222> LOCATION: (405)..(405)
<223> OTHER INFORMATION: a, c, g, t, unknown or other
<220> FEATURE:
<221> NAME/KEY: modified_base
<222> LOCATION: (407)..(407)
<223> OTHER INFORMATION: a, c, g, t, unknown or other
<220> FEATURE:
<221> NAME/KEY: modified_base
<222> LOCATION: (410)..(410)
<223> OTHER INFORMATION: a, c, g, t, unknown or other
<220> FEATURE:
<221> NAME/KEY: modified_base
<222> LOCATION: (413)..(413)
<223> OTHER INFORMATION: a, c, g, t, unknown or other
<220> FEATURE:
<221> NAME/KEY: modified_base
<222> LOCATION: (416)..(416)
<223> OTHER INFORMATION: a, c, g, t, unknown or other
<220> FEATURE:
<221> NAME/KEY: modified_base
<222> LOCATION: (428)..(428)
<223> OTHER INFORMATION: a, c, g, t, unknown or other
<220> FEATURE:
<221> NAME/KEY: modified_base
<222> LOCATION: (437)..(437)
<223> OTHER INFORMATION: a, c, g, t, unknown or other
<220> FEATURE:
<221> NAME/KEY: modified_base
<222> LOCATION: (446)..(446)
<223> OTHER INFORMATION: a, c, g, t, unknown or other
<220> FEATURE:
<221> NAME/KEY: modified_base
<222> LOCATION: (449)..(449)
<223> OTHER INFORMATION: a, c, g, t, unknown or other
<220> FEATURE:
<221> NAME/KEY: modified_base
<222> LOCATION: (461)..(461)
<223> OTHER INFORMATION: a, c, g, t, unknown or other

<400> SEQUENCE: 10

```
gcnmgngcng tnathatgtt ygcnaaygar gaygayathm gnmgnathyt ngargcngcn    60
aaraarytna aycarwsngg ncayttyytn tggathggnw sngaywsntg gggnwsnaar   120
athgcnccng tntaycarca rgargarath gcngarggng cngtnacnat hytnccnaar   180
mgngcnwsna thgayggntt ygaycartay ttymgnwsnc aracnytngc naayaaymgn   240
rngnaaygtn tggttygcng arttytggga rgaraaytty ggntgyaary tnggnwsnca   300
yggnaarmgn aaywsncaya thaaraartg yacngaraay gtnccngtna cngayttytt   360
ygtnggnccn gtntgyatha thccnaarac ngayacnaar ccnrngnwsn wsngtntggg   420
aygarmgnca ygaywsncay athccnytng argaytgymg ntty                    464
```

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
gcagtgatta tgtttgccaa tgaggatgac atcagg                              36
```

<210> SEQ ID NO 12

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other

<400> SEQUENCE: 12
gcngtnatha tgttygcnaa ygargaygay athmgn                              36

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcatcaattg atggatttga tcaatacttt agaagccaaa ctcttgccaa taatcga       57

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (48)..(48)
```

```
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other

<400> SEQUENCE: 14
gcnwsnathg ayggnttyga ycartaytty mgnwsncara cnytngcnaa yaaymgn      57

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcatcaattg atggatttga tcaatacttt aga                                33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other

<400> SEQUENCE: 16
gcnwsnathg ayggnttyga ycartaytty mgn                                33

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgcacagaaa atgtccctgt gactgatttc tttgtgggac cagtctgcat cattcctaag   60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
```

```
<222> LOCATION: (15)..(15)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other
<220> FEATURE:
<221> NAME/KEY: modified_base
<222> LOCATION: (39)..(39)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other

<400> SEQUENCE: 18
tgyacngara aygtnccngt nacngaytty ttygtnggnc cngtntgyat hathccnaar      60

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcgagcgtgt gggatgaacg gcatgactca cacattcccc tggaggactg cagg           54

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (30)..(30)
```

```
<223> OTHER INFORMATION: a, c, g, t, unknown or other
<220> FEATURE:
<221> NAME/KEY: modified_base
<222> LOCATION: (39)..(39)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (53)..(53)
<223> OTHER INFORMATION: a, c, g, t, unknown or other
<220> FEATURE:
<221> NAME/KEY: modified_base
<222> LOCATION: (55)..(55)
<223> OTHER INFORMATION: a, c, g, t, unknown or other

<400> SEQUENCE: 20
wsnwsngtnt gggaygarmg ncaygaywsn cayathccny tngargaytg yrngn         55

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
catgactcac acattcccct ggaggactgc agg                                33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (21)..(21)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other

<400> SEQUENCE: 22
caygaywsnc ayathccnyt ngargaytgy mgn                                33

<210> SEQ ID NO 23
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gcatcaattg atggatttga tcaatacttt agaagccaaa ctcttgccaa taatcgaaga    60
aatgtgtggt ttgcagaatt ttgggaggag aattttggct gcaagttagg atcacatggg   120
```

```
aaaaggaaca gtcatataaa gaaatgcaca gaaaatgtcc ctgtgactga tttctttgtg      180
ggaccagtct gcatcattcc taagactgac acaaagcccc gctcgagcgt gtgggatgaa      240
cggcatgact cacacattcc cctggaggac tgcagg                                276
```

```
<210> SEQ ID NO 24
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (33)..(33)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other
<220> FEATURE:
<221> NAME/KEY: modified_base
<222> LOCATION: (42)..(42)
<223> OTHER INFORMATION: a, c, g, t, unknown or other
<220> FEATURE:
<221> NAME/KEY: modified_base
<222> LOCATION: (45)..(45)
<223> OTHER INFORMATION: a, c, g, t, unknown or other
<220> FEATURE:
<221> NAME/KEY: modified_base
<222> LOCATION: (48)..(48)
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other
<220> FEATURE:
<221> NAME/KEY: modified_base
<222> LOCATION: (60)..(60)
<223> OTHER INFORMATION: a, c, g, t, unknown or other
<220> FEATURE:
<221> NAME/KEY: modified_base
<222> LOCATION: (66)..(66)
<223> OTHER INFORMATION: a, c, g, t, unknown or other
<220> FEATURE:
<221> NAME/KEY: modified_base
<222> LOCATION: (75)..(75)
<223> OTHER INFORMATION: a, c, g, t, unknown or other
<220> FEATURE:
<221> NAME/KEY: modified_base
<222> LOCATION: (99)..(99)
<223> OTHER INFORMATION: a, c, g, t, unknown or other
<220> FEATURE:
<221> NAME/KEY: modified_base
<222> LOCATION: (108)..(108)
<223> OTHER INFORMATION: a, c, g, t, unknown or other
<220> FEATURE:
<221> NAME/KEY: modified_base
<222> LOCATION: (111)..(111)
<223> OTHER INFORMATION: a, c, g, t, unknown or other
<220> FEATURE:
<221> NAME/KEY: modified_base
<222> LOCATION: (114)..(114)
<223> OTHER INFORMATION: a, c, g, t, unknown or other
<220> FEATURE:
```

```
<221> NAME/KEY: modified_base
<222> LOCATION: (120)..(120)
<223> OTHER INFORMATION: a, c, g, t, unknown or other
<220> FEATURE:
<221> NAME/KEY: modified_base
<222> LOCATION: (126)..(126)
<223> OTHER INFORMATION: a, c, g, t, unknown or other
<220> FEATURE:
<221> NAME/KEY: modified_base
<222> LOCATION: (132)..(132)
<223> OTHER INFORMATION: a, c, g, t, unknown or other
<220> FEATURE:
<221> NAME/KEY: modified_base
<222> LOCATION: (150)..(150)
<223> OTHER INFORMATION: a, c, g, t, unknown or other
<220> FEATURE:
<221> NAME/KEY: modified_base
<222> LOCATION: (159)..(159)
<223> OTHER INFORMATION: a, c, g, t, unknown or other
<220> FEATURE:
<221> NAME/KEY: modified_base
<222> LOCATION: (162)..(162)
<223> OTHER INFORMATION: a, c, g, t, unknown or other
<220> FEATURE:
<221> NAME/KEY: modified_base
<222> LOCATION: (165)..(165)
<223> OTHER INFORMATION: a, c, g, t, unknown or other
<220> FEATURE:
<221> NAME/KEY: modified_base
<222> LOCATION: (168)..(168)
<223> OTHER INFORMATION: a, c, g, t, unknown or other
<220> FEATURE:
<221> NAME/KEY: modified_base
<222> LOCATION: (180)..(180)
<223> OTHER INFORMATION: a, c, g, t, unknown or other
<220> FEATURE:
<221> NAME/KEY: modified_base
<222> LOCATION: (183)..(183)
<223> OTHER INFORMATION: a, c, g, t, unknown or other
<220> FEATURE:
<221> NAME/KEY: modified_base
<222> LOCATION: (186)..(186)
<223> OTHER INFORMATION: a, c, g, t, unknown or other
<220> FEATURE:
<221> NAME/KEY: modified_base
<222> LOCATION: (189)..(189)
<223> OTHER INFORMATION: a, c, g, t, unknown or other
<220> FEATURE:
<221> NAME/KEY: modified_base
<222> LOCATION: (201)..(201)
<223> OTHER INFORMATION: a, c, g, t, unknown or other
<220> FEATURE:
<221> NAME/KEY: modified_base
<222> LOCATION: (207)..(207)
<223> OTHER INFORMATION: a, c, g, t, unknown or other
<220> FEATURE:
<221> NAME/KEY: modified_base
<222> LOCATION: (213)..(213)
<223> OTHER INFORMATION: a, c, g, t, unknown or other
<220> FEATURE:
<221> NAME/KEY: modified_base
<222> LOCATION: (219)..(219)
<223> OTHER INFORMATION: a, c, g, t, unknown or other
<220> FEATURE:
<221> NAME/KEY: modified_base
<222> LOCATION: (222)..(222)
<223> OTHER INFORMATION: a, c, g, t, unknown or other
<220> FEATURE:
<221> NAME/KEY: modified_base
<222> LOCATION: (225)..(225)
<223> OTHER INFORMATION: a, c, g, t, unknown or other
<220> FEATURE:
<221> NAME/KEY: modified_base
<222> LOCATION: (228)..(228)
<223> OTHER INFORMATION: a, c, g, t, unknown or other
<220> FEATURE:
<221> NAME/KEY: modified_base
<222> LOCATION: (231)..(231)
<223> OTHER INFORMATION: a, c, g, t, unknown or other
```

-continued

<220> FEATURE:
<221> NAME/KEY: modified_base
<222> LOCATION: (243)..(243)
<223> OTHER INFORMATION: a, c, g, t, unknown or other
<220> FEATURE:
<221> NAME/KEY: modified_base
<222> LOCATION: (252)..(252)
<223> OTHER INFORMATION: a, c, g, t, unknown or other
<220> FEATURE:
<221> NAME/KEY: modified_base
<222> LOCATION: (261)..(261)
<223> OTHER INFORMATION: a, c, g, t, unknown or other
<220> FEATURE:
<221> NAME/KEY: modified_base
<222> LOCATION: (264)..(264)
<223> OTHER INFORMATION: a, c, g, t, unknown or other
<220> FEATURE:
<221> NAME/KEY: modified_base
<222> LOCATION: (276)..(276)
<223> OTHER INFORMATION: a, c, g, t, unknown or other

<400> SEQUENCE: 24
gcnwsnathg ayggnttyga ycartaytty mgnwsncara cnytngcnaa yaaymgnmgn 60
aaygtntggt tygcngartt ytgggargar aayttyggnt gyaarytngg nwsncayggn 120
aarmgnaayw sncayathaa raartgyacn garaaygtnc cngtnacnga yttyttygtn 180
ggnccngtnt gyathathcc naaracngay acnaarccnm gnwsnwsngt ntgggaygar 240
mgncaygayw sncayathcc nytngargay tgymgn 276

<210> SEQ ID NO 25
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Asp Ala Glu Phe Arg His Asp Ser Gly Tyr Glu Val His His Gln Lys
1 5 10 15

Leu Val Phe Phe Ala Glu Asp Val Gly Ser Asn Lys Gly Ala Ile Ile
20 25 30

Gly Leu Met Val Gly Gly Val Val Ile Ala
35 40

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Phe Asp Gln Tyr Phe Arg Ser Gln Thr Leu Gly Gly
1 5 10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

```
Phe Asp Arg Tyr Phe Arg Ser Arg Thr Leu Gly Gly
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Phe Asp Asp Tyr Phe Leu Lys Leu Arg Leu Gly Gly
1               5                   10
```

<210> SEQ ID NO 29
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Ala Arg Ala Val Ile Met Phe Ala Asn Glu Asp Ile Arg Arg Ile
1               5                   10                  15

Leu Glu Ala Ala Lys Lys Leu Asn Gln Ser Gly His Phe Leu Trp Ile
                20                  25                  30

Gly Ser Asp Ser Trp Gly Ser Lys Ile Ala Pro Val Tyr Gln Gln Glu
            35                  40                  45

Glu Ile Ala Glu Gly Ala Val Thr Ile Leu Pro Lys Arg Ala Ser Ile
    50                  55                  60

Asp Gly Phe Asp Arg Tyr Phe Arg Ser Arg Thr Leu Ala Asn Asn Arg
65                  70                  75                  80

Arg Asn Val Trp Phe Ala Glu Phe Trp Glu Glu Asn Phe Gly Cys Lys
                85                  90                  95

Leu Gly Ser His Gly Lys Arg Asn Ser His Ile Lys Lys Cys Thr Gly
            100                 105                 110

Leu Glu Arg Ile Ala Arg Asp Ser Ser Tyr Gln Glu Gly Lys Val
    115                 120                 125

Gln Phe Val Ile Asp Ala Val Tyr Ser Met Ala Tyr Ala Leu His Asn
    130                 135                 140

Met His Lys Glu Arg Cys Pro Gly Tyr Ile
145                 150
```

<210> SEQ ID NO 30
<211> LENGTH: 154
<212> TYPE: PRT
<213> ORGANISM: Homo sapiens

<400> SEQUENCE: 30

```
Ala Arg Ala Val Ile Met Phe Ala Asn Glu Asp Ile Arg Arg Ile
1               5                   10                  15

Leu Glu Ala Ala Lys Lys Leu Asn Gln Ser Gly His Phe Leu Trp Ile
                20                  25                  30

Gly Ser Asp Ser Trp Gly Ser Lys Ile Ala Pro Val Tyr Gln Gln Glu
            35                  40                  45

Glu Ile Ala Glu Gly Ala Val Thr Ile Leu Pro Lys Arg Ala Ser Ile
    50                  55                  60
```

Asp Gly Phe Asp Gln Tyr Phe Arg Ser Arg Thr Leu Ala Asn Asn Arg
65                  70                  75                  80

Arg Asn Val Trp Phe Ala Glu Phe Trp Glu Glu Asn Phe Gly Cys Lys
                85                  90                  95

Leu Gly Ser His Gly Lys Arg Asn Ser His Ile Lys Lys Cys Thr Gly
            100                 105                 110

Leu Glu Arg Ile Ala Arg Asp Ser Ser Tyr Glu Gln Glu Gly Lys Val
            115                 120                 125

Gln Phe Val Ile Asp Ala Val Tyr Ser Met Ala Tyr Ala Leu His Asn
        130                 135                 140

Met His Lys Asp Leu Cys Pro Gly Tyr Ile
145                 150

<210> SEQ ID NO 31
<211> LENGTH: 154
<212> TYPE: PRT
<213> ORGANISM: Homo sapiens

<400> SEQUENCE: 31

Ala Arg Ala Val Ile Met Phe Ala Asn Glu Asp Asp Ile Arg Arg Ile
1               5                   10                  15

Leu Glu Ala Ala Lys Lys Leu Asn Gln Ser Gly His Phe Leu Trp Ile
            20                  25                  30

Gly Ser Asp Ser Trp Gly Ser Lys Ile Ala Pro Val Tyr Gln Gln Glu
        35                  40                  45

Glu Ile Ala Glu Gly Ala Val Thr Ile Leu Pro Lys Arg Ala Ser Ile
    50                  55                  60

Asp Gly Phe Asp Arg Tyr Phe Arg Ser Arg Thr Leu Ala Asn Asn Arg
65                  70                  75                  80

Arg Asn Val Trp Phe Ala Glu Phe Trp Glu Glu Asn Phe Gly Cys Lys
                85                  90                  95

Leu Gly Ser His Gly Lys Arg Asn Ser His Ile Lys Lys Cys Thr Gly
            100                 105                 110

Leu Glu Arg Ile Ala Arg Asp Ser Ser Tyr Glu Gln Glu Gly Lys Val
            115                 120                 125

Gln Phe Val Ile Asp Ala Val Tyr Ser Met Ala Tyr Ala Leu His Asn
        130                 135                 140

Met His Lys Glu Arg Cys Pro Gly Tyr Ile
145                 150

<210> SEQ ID NO 32
<211> LENGTH: 154
<212> TYPE: PRT
<213> ORGANISM: Homo sapiens

<400> SEQUENCE: 32

Ala Arg Ala Val Ile Met Phe Ala Asn Glu Asp Asp Ile Arg Arg Ile
1               5                   10                  15

Leu Glu Ala Ala Lys Lys Leu Asn Gln Ser Gly His Phe Leu Trp Ile
            20                  25                  30

Gly Ser Asp Ser Trp Gly Ser Lys Ile Ala Pro Val Tyr Gln Gln Glu
        35                  40                  45

Glu Ile Ala Glu Gly Ala Val Thr Ile Leu Pro Lys Arg Ala Ser Ile
    50                  55                  60

Asp Gly Phe Asp Gln Tyr Phe Arg Ser Gln Thr Leu Ala Asn Asn Arg
65                  70                  75                  80

```
                        Arg Asn Val Trp Phe Ala Glu Phe Trp Glu Asn Phe Gly Cys Lys
                                        85                  90                  95

Leu Gly Ser His Gly Lys Arg Asn Ser His Ile Lys Lys Cys Thr Glu
                                    100                 105                 110

Asn Val Pro Val Thr Asp Phe Phe Val Gly Pro Val Cys Ile Ile Pro
                                    115                 120                 125

Lys Thr Asp Thr Lys Pro Arg Ser Ser Val Trp Asp Glu Arg His Asp
                        130                 135                 140

Ser His Ile Pro Leu Glu Asp Cys Arg Phe
                        145                 150

<210> SEQ ID NO 33
<211> LENGTH: 197
<212> TYPE: PRT
<213> ORGANISM: Rattus sp.

<400> SEQUENCE: 33

Gly Gly Val Cys Ile Ala Gln Ser Gln Lys Ile Pro Arg Glu Pro Arg
1               5                   10                  15

Pro Gly Glu Phe Glu Lys Ile Ile Lys Arg Leu Leu Glu Thr Pro Asn
            20                  25                  30

Ala Arg Ala Val Ile Met Phe Ala Asn Glu Asp Asp Ile Arg Arg Ile
        35                  40                  45

Leu Glu Ala Ala Lys Lys Leu Asn Gln Ser Gly His Phe Leu Trp Ile
50                  55                  60

Gly Ser Asp Ser Trp Gly Ser Lys Ile Ala Pro Val Tyr Gln Gln Glu
65                  70                  75                  80

Glu Ile Ala Glu Gly Ala Val Thr Ile Leu Pro Lys Arg Ala Ser Ile
                85                  90                  95

Asp Gly Phe Asp Arg Tyr Phe Arg Ser Arg Thr Leu Ala Asn Asn Arg
            100                 105                 110

Arg Asn Val Trp Phe Ala Glu Phe Trp Glu Glu Asn Phe Gly Cys Lys
        115                 120                 125

Leu Gly Ser His Gly Lys Arg Asn Ser His Ile Lys Lys Cys Thr Gly
130                 135                 140

Leu Glu Arg Ile Ala Arg Asp Ser Ser Tyr Glu Gln Glu Gly Lys Val
145                 150                 155                 160

Gln Phe Val Ile Asp Ala Val Tyr Ser Met Ala Tyr Ala Leu His Asn
                165                 170                 175

Met His Lys Glu Arg Cys Pro Gly Tyr Ile Gly Leu Cys Pro Arg Met
            180                 185                 190

Val Thr Ile Asp Gly
        195

<210> SEQ ID NO 34
<211> LENGTH: 187
<212> TYPE: PRT
<213> ORGANISM: Homo sapiens

<400> SEQUENCE: 34

Asp Gly Val Cys Ile Ala Gln Ser Gln Lys Ile Pro Arg Glu Pro Arg
1               5                   10                  15

Pro Gly Glu Phe Glu Lys Ile Ile Lys Cys Leu Leu Glu Thr Pro Asn
            20                  25                  30

Ala Arg Ala Val Ile Met Phe Ala Asn Glu Asp Asp Ile Arg Arg Ile
        35                  40                  45
```

```
Leu Glu Ala Ala Lys Lys Leu Asn Gln Ser Gly His Phe Leu Trp Ile
 50                  55                  60

Gly Ser Asp Ser Trp Gly Ser Lys Ile Ala Pro Val Tyr Gln Gln Glu
 65                  70                  75                  80

Glu Ile Ala Glu Gly Ala Val Thr Ile Leu Pro Lys Arg Ala Ser Ile
                 85                  90                  95

Asp Gly Phe Asp Gln Tyr Phe Arg Ser Gln Thr Leu Ala Asn Asn Arg
            100                 105                 110

Arg Asn Val Trp Phe Ala Glu Phe Trp Glu Asn Phe Gly Cys Lys
        115                 120                 125

Leu Gly Ser His Gly Lys Arg Asn Ser His Ile Lys Lys Cys Thr Glu
130                 135                 140

Asn Val Pro Val Thr Asp Phe Phe Val Gly Pro Val Cys Ile Ile Pro
145                 150                 155                 160

Lys Thr Asp Thr Lys Pro Arg Ser Ser Val Trp Asp Glu Arg His Asp
                165                 170                 175

Ser His Ile Pro Leu Glu Asp Cys Arg Phe Asp
                180                 185

<210> SEQ ID NO 35
<211> LENGTH: 198
<212> TYPE: PRT
<213> ORGANISM: Rattus sp.

<400> SEQUENCE: 35

Gly Gly Val Cys Ile Ala Gln Ser Ile Lys Ile Pro Arg Glu Pro Lys
 1               5                  10                  15

Pro Gly Glu Phe His Lys Val Ile Arg Arg Leu Met Glu Thr Pro Asn
                20                  25                  30

Ala Arg Gly Ile Ile Ile Phe Ala Asn Glu Asp Asp Ile Arg Arg Val
            35                  40                  45

Leu Glu Ala Thr Arg Gln Ala Asn Leu Thr Gly His Phe Leu Trp Val
 50                  55                  60

Gly Ser Asp Ser Trp Gly Ser Lys Ile Ser Pro Ile Leu Asn Leu Glu
 65                  70                  75                  80

Glu Glu Ala Val Gly Ala Ile Thr Ile Leu Pro Lys Arg Ala Ser Ile
                 85                  90                  95

Asp Gly Phe Asp Gln Tyr Phe Met Thr Arg Ser Leu Glu Asn Asn Arg
            100                 105                 110

Arg Asn Ile Trp Phe Ala Glu Phe Trp Glu Glu Asn Phe Asn Cys Lys
        115                 120                 125

Leu Thr Ser Ser Gly Gly Gln Ser Asp Asp Ser Thr Arg Lys Cys Thr
130                 135                 140

Gly Glu Glu Arg Ile Gly Gln Asp Ser Ala Tyr Glu Gln Glu Gly Lys
145                 150                 155                 160

Val Gln Phe Val Ile Asp Ala Val Tyr Ala Ile Ala His Ala Leu His
                165                 170                 175

Ser Met His Gln Ala Leu Cys Pro Gly His Thr Gly Leu Cys Pro Ala
            180                 185                 190

Met Glu Pro Thr Asp Gly
            195

<210> SEQ ID NO 36
<211> LENGTH: 200
<212> TYPE: PRT
<213> ORGANISM: Rattus sp.
```

<400> SEQUENCE: 36

```
Gly Gly Leu Cys Ile Ala Gln Ser Val Arg Ile Pro Gln Glu Arg Lys
1               5                   10                  15

Asp Arg Thr Ile Asp Phe Asp Arg Ile Ile Lys Gln Leu Leu Asp Thr
            20                  25                  30

Pro Asn Ser Arg Ala Val Val Ile Phe Ala Asn Asp Glu Asp Ile Lys
        35                  40                  45

Gln Ile Leu Ala Ala Ala Lys Arg Ala Asp Gln Val Gly His Phe Leu
    50                  55                  60

Trp Val Gly Ser Asp Ser Trp Gly Ser Lys Ile Asn Pro Leu His Gln
65                  70                  75                  80

His Glu Asp Ile Ala Glu Gly Ala Ile Thr Ile Gln Pro Lys Arg Ala
                85                  90                  95

Thr Val Glu Gly Phe Asp Ala Tyr Phe Thr Ser Arg Thr Leu Glu Asn
            100                 105                 110

Asn Arg Arg Asn Val Trp Phe Ala Glu Tyr Trp Glu Glu Asn Phe Asn
        115                 120                 125

Cys Lys Leu Thr Ile Ser Gly Ser Lys Lys Glu Asp Thr Asp Arg Lys
    130                 135                 140

Cys Thr Gly Gln Glu Arg Ile Gly Lys Asp Ser Asn Tyr Glu Gln Glu
145                 150                 155                 160

Gly Lys Val Gln Phe Val Ile Asp Ala Val Tyr Ala Met Ala His Ala
                165                 170                 175

Leu His His Met Asn Lys Asp Leu Cys Ala Asp Tyr Arg Gly Val Cys
            180                 185                 190

Pro Glu Met Glu Gln Ala Gly Gly
        195                 200
```

<210> SEQ ID NO 37
<211> LENGTH: 198
<212> TYPE: PRT
<213> ORGANISM: Rattus sp.

<400> SEQUENCE: 37

```
Gly Gly Val Cys Ile Ala Gln Ser Val Lys Ile Pro Arg Glu Pro Lys
1               5                   10                  15

Thr Gly Glu Phe Asp Lys Ile Ile Lys Arg Leu Leu Glu Thr Ser Asn
            20                  25                  30

Ala Arg Gly Ile Ile Ile Phe Ala Asn Glu Asp Asp Ile Arg Arg Val
        35                  40                  45

Leu Glu Ala Ala Arg Arg Ala Asn Gln Thr Gly His Phe Phe Trp Met
    50                  55                  60

Gly Ser Asp Ser Trp Gly Ser Lys Ser Ala Pro Val Leu Arg Leu Glu
65                  70                  75                  80

Glu Val Ala Glu Gly Ala Val Thr Ile Leu Pro Lys Arg Met Ser Val
                85                  90                  95

Arg Gly Phe Asp Arg Tyr Phe Ser Ser Arg Thr Leu Asp Asn Asn Arg
            100                 105                 110

Arg Asn Ile Trp Phe Ala Glu Phe Trp Glu Asp Asn Phe His Cys Lys
        115                 120                 125

Leu Ser Arg His Ala Leu Lys Lys Gly Ser His Ile Lys Lys Cys Thr
    130                 135                 140

Asn Arg Glu Arg Ile Gly Gln Asp Ser Ala Tyr Glu Gln Glu Gly Lys
145                 150                 155                 160
```

Val Gln Phe Val Ile Asp Ala Val Tyr Ala Met Gly His Ala Leu His
            165                 170                 175

Ala Met His Arg Asp Leu Cys Pro Gly Arg Val Gly Leu Cys Pro Arg
            180                 185                 190

Met Asp Pro Val Asp Gly
        195

<210> SEQ ID NO 38
<211> LENGTH: 154
<212> TYPE: PRT
<213> ORGANISM: Homo sapiens

<400> SEQUENCE: 38

Ala Arg Ala Val Ile Met Phe Ala Asn Glu Asp Asp Ile Arg Arg Ile
1               5                   10                  15

Leu Glu Ala Ala Lys Lys Leu Asn Gln Ser Gly His Phe Leu Trp Ile
            20                  25                  30

Gly Ser Asp Ser Trp Gly Ser Lys Ile Ala Pro Val Tyr Gln Gln Glu
        35                  40                  45

Glu Ile Ala Glu Gly Ala Val Thr Ile Leu Pro Lys Arg Ala Ser Ile
    50                  55                  60

Asp Gly Phe Asp Arg Tyr Phe Arg Ser Arg Thr Leu Ala Asn Asn Arg
65                  70                  75                  80

Arg Asn Val Trp Phe Ala Glu Phe Trp Glu Glu Asn Phe Gly Cys Lys
                85                  90                  95

Leu Gly Ser His Gly Lys Arg Asn Ser His Ile Lys Lys Cys Thr Gly
            100                 105                 110

Leu Glu Arg Ile Ala Arg Asp Ser Ser Tyr Glu Gln Glu Gly Lys Val
        115                 120                 125

Gln Phe Val Ile Asp Ala Val Tyr Ser Met Ala Tyr Ala Leu His Asn
    130                 135                 140

Met His Lys Asp Leu Cys Pro Gly Tyr Ile
145                 150

<210> SEQ ID NO 39
<211> LENGTH: 154
<212> TYPE: PRT
<213> ORGANISM: Rattus norvegicus

<400> SEQUENCE: 39

Ala Arg Ala Val Ile Met Phe Ala Asn Glu Asp Asp Ile Arg Arg Ile
1               5                   10                  15

Leu Glu Ala Ala Lys Lys Leu Asn Gln Ser Gly His Phe Leu Trp Ile
            20                  25                  30

Gly Ser Asp Ser Trp Gly Ser Lys Ile Ala Pro Val Tyr Gln Gln Glu
        35                  40                  45

Glu Ile Ala Glu Gly Ala Val Thr Ile Leu Pro Lys Arg Ala Ser Ile
    50                  55                  60

Asp Gly Phe Asp Arg Tyr Phe Arg Ser Arg Thr Leu Ala Asn Asn Arg
65                  70                  75                  80

Arg Asn Val Trp Phe Ala Glu Phe Trp Glu Glu Asn Phe Gly Cys Lys
                85                  90                  95

Leu Gly Ser His Gly Lys Arg Asn Ser His Ile Lys Lys Cys Thr Gly
            100                 105                 110

Leu Glu Arg Ile Ala Arg Asp Ser Ser Tyr Glu Gln Glu Gly Lys Val
        115                 120                 125

```
Gln Phe Val Ile Asp Ala Val Tyr Ser Met Ala Tyr Ala Leu His Asn
    130                 135                 140

Met His Lys Glu Leu Cys Pro Gly Tyr Ile
145                 150
```